US012577542B2

(12) United States Patent
Godaux et al.

(10) Patent No.: US 12,577,542 B2
(45) Date of Patent: Mar. 17, 2026

(54) MONOMER POLYPEPTIDE HAVING HYDROGENASE ACTIVITY, IN PARTICULAR RECOMBINANT MONOMER POLYPEPTIDE HAVING HYDROGENASE ACTIVITY

(71) Applicant: H2WIN S.A., Nivelles (BE)

(72) Inventors: Damien Godaux, Liege (BE); Philippe Lorge, Nivelles (BE); Bart Ghysels, Laeken (BE); Nathalie Job, Vaux-sous-Chevremont (BE); Fabrice Franck, Liege (BE); Giuseppe Caldarella, Ans (BE); Pierre Cardol, Verviers (BE); Claire Remacle, Vise (BE)

(73) Assignee: H2WIN S.A., Nivelles (BE)

( * ) Notice: Subject to any disclaimer, the term of this patent is extended or adjusted under 35 U.S.C. 154(b) by 814 days.

(21) Appl. No.: 17/775,649

(22) PCT Filed: Nov. 12, 2020

(86) PCT No.: PCT/EP2020/081931
§ 371 (c)(1),
(2) Date: May 10, 2022

(87) PCT Pub. No.: WO2021/094465
PCT Pub. Date: May 20, 2021

(65) Prior Publication Data
US 2023/0011570 A1 Jan. 12, 2023

(30) Foreign Application Priority Data

Nov. 13, 2019 (BE) .................................. 2019/5783
Nov. 13, 2019 (EP) .................................. 19208856

(51) Int. Cl.
| | |
|---|---|
| *C12N 9/02* | (2006.01) |
| *C12N 15/63* | (2006.01) |
| *C12P 3/00* | (2006.01) |
| *C12Q 1/00* | (2006.01) |

(52) U.S. Cl.
CPC .......... *C12N 9/0067* (2013.01); *C12N 15/63* (2013.01); *C12P 3/00* (2013.01); *C12Q 1/001* (2013.01); *Y02E 60/50* (2013.01)

(58) Field of Classification Search
None
See application file for complete search history.

(56) References Cited

FOREIGN PATENT DOCUMENTS

| JP | 2010535471 A | 11/2010 |
|---|---|---|
| WO | 2009019613 A2 | 2/2009 |
| WO | 2009075798 A2 | 6/2009 |

OTHER PUBLICATIONS

Pinske, Efficient electron transfer from hydrogen to benzyl viologen by the [NiFe]-hydrogenases of *Escherichia coli* is dependent on the coexpression of the iron-sulfur cluster-containing small subunit, Arch. Microbiol. 193, 2011, 893-903. (Year: 2011).*
Uniprot, Accession No. P22320, 2018, www.uniprot.org. (Year: 2020).*
Jugder et al., An analysis of the changes in soluble hydrogenase and global gene expression in Cupriavidus necator (*Ralstonia eutropha*) H16 grown in heterotrophic diauxic batch culture, Microbial Cell Factories 14, 2015, 42. (Year: 2015).*
Schneider et al., Purification and properties of soluble hydrogenase from Alcaligenes eutrophus H16, Biochim. Biophys. Acta 452, 1976, 66-80. (Year: 1976).*
Ballantine et al., "Nickel-Containing Hydrogenase Isoenzymes From Anaerobically Grown *Escherichia coli* K-12," J Bacteriol., 163(2):454-459, Aug. 1985.
Constanze Pinske et al., "Efficient Electron Transfer From Hydrogen to Benzyl Viologen by the [NiFe]-Hydrogenases of *Escherichia coli* Is Dependent on the Coexpression of the Ironsulfur Cluster-Containing Small Subunit," Arch Microbiol., 193(12):893-903, Dec. 2011.
Hartmann et al., "A Membrane-Bound [NiFe]-Hydrogenase Large Subunit Precursor Whose C-Terminal Extension Is Not Essential for Cofactor Incorporation but Guarantees Optimal Maturation," Microbiologyopen, 9(6):1197-1206, Jun. 2020.
Hornhardt et al., "Characterization of a Native Subunit of the NAD-Linked Hydrogenase Isolated From a Mutant of Alcaligenes eutrophus H16," Biochimie, 68(1):15-24, Jan. 1986.
International Search Report of the ISA/EP in PCT/EP2020/081931, dated Feb. 1, 2021, 4pgs.
Massanz et al., "Subforms and In Vitro Reconstitution of the NAD-Reducing Hydrogenase of Alcaligenes eutrophus," J Bacteriol., 180(5):1023-1029, Mar. 1998.
Moritz Senger et al., "Proteolytic Cleavage Orchestrates Cofactor Insertion and Protein Assembly in [NiFe]-Hydrogenase Biosynthesis," J. Biol. Chem., 292(28):11670-11681, May 2017.
Przybyla et al., "Structure-Function Relationships Among the Nickel-Containing Hydrogenases," FEMS Microbiol Rev., 8(2):109-135, Feb. 1992.
Wells et al., "Engineering a non-native hydrogen production pathway into *Escherichia coli* via a cyanobacterial [NiFe] hydrogenase", Metabolic Engineering 13 (Jan. 2011) pp. 445-453.
Albracht, Simon P.J., "Nickel hydrogenases: in search of the active site," Biochimica et Biophysica Acta., 1188, 167-204, Jun. 1994.
Appel et al., "The bidirectional hydrogenase of *Synechocystis* sp. PCC 6803 works as an electron valve during photosynthesis," Arch Microbiol., 173:333-338, Mar. 2000.
Carrieri et al., "The role of the bidirectional hydrogenase in cyanobacteria," Bioresource Technology., 102(18), 8368-8377, Apr. 2011.
Cassier-Chauvat et al., "Advances in the Function and Regulation of Hydrogenase in the Cyanobacterium Synechocystis PCC6803," Int. J. Mol. Sci., 15, 19938-19951, Oct. 2014.

(Continued)

*Primary Examiner* — Todd M Epstein
(74) *Attorney, Agent, or Firm* — Haukaas Fortius PLLC; Michael H. Haukaas

(57) ABSTRACT

The present invention relates to a monomeric polypeptide including a single subunit comprising the active site of a [NiFe]-hydrogenase-like protein, said monomeric polypeptide having hydrogenase activity.

20 Claims, 9 Drawing Sheets

Specification includes a Sequence Listing.

(56)                    References Cited

OTHER PUBLICATIONS

Dutheil et al., "The AbrB2 Autorepressor, Expressed from an Atypical Promoter, Represses the Hydrogenase Operon to Regulate Hydrogen Production in Synechocystis Strain PCC6803," Journal of Bacteriology., vol. 194, No. 19, 5423-5433, Oct. 2012.

Eckert et al., "Genetic Analysis of the Hox Hydrogenase in the Cyanobacterium synechocystis sp. PCC 6803 Reveals Subunit Roles in Association, Assembly, Maturation, and Function," Journal of Biological Chemistry., 287(52):43502-43515, Dec. 2012.

English et al., "Recombinant and in vitro expression systems for hydrogenases: new frontiers in basic and applied studies for biological and synthetic H2 production," Dalton Trans., 2009, 9970-9978, Oct. 2009.

GenBank., Hydrogenase large subunit [Synechocystis, GenBank: BAA18091.1, Oct. 7, 2016.

Germer et al., "Overexpression, Isolation, and Spectroscopic Characterization of the Bidirectional [NiFe] Hydrogenase from Synechocystis sp. PCC 6803," Journal of Biological Chemistry., 284(52):36462-36472, Sep. 2009.

Ghirardi et al., "Oxygen Sensitivity of Algal H2-Production," Applied Biochemistry and Biotechnology., vol. 63-65, Spring 1997.

Ghysels et al., "Function of the Chloroplast Hydrogenase in the Microalga Chlamydomonas: The Role of Hydrogenase and State Transitions during Photosynthetic Activation in Anaerobiosis," PLoS ONE., 8(5): e64161, May 2013.

Godaux et al., "Induction of Photosynthetic Carbon Fixation in Anoxia Relies on Hydrogenase Activity and Proton-Gradient Regulation-Like1-Mediated Cyclic Electron Flow in Chlamydomonas reinhardtii1," Plant Physiol., 168(2):648-658, Jun. 2015.

Happe et al., "Biological activition of hydrogen," Nature., 385(6612):126, Jan. 1997.

Hoffmann et al., "Mutagenesis of hydrogenase accessory genes of Synechocystis sp. PCC 6803," FEBS Journal., 273(19):4516-27, Oct. 2006.

Kim et al., "Production of biohydrogen by heterologous expression of oxygen-tolerant Hydrogenovibrio marinus [NiFe]-hydrogenase in Escherichia coli," Journal of Biotechnology., 155, 312-319, Jul. 2011.

King et al., "Functional Studies of [FeFe] Hydrogenase Maturation in an Escherichia coli Biosynthetic System," J Acteriol., 188(6):2163-72, Mar. 2006.

Kiss et al., "Transcriptional regulation of the bidirectional hydrogenase in the cyanobacterium Synechocystis 6803," J Biotechnol., 142(1):31-7, Jun. 2009.

Kuchenreuther et al., "Tyrosine, Cysteine, and S-Adenosyl Methionine Stimulate In Vitro [FeFe] Hydrogenase Activation," PLoS ONE., 4(10): e7565, Oct. 2009.

Maeda et al., "Inhibition of hydrogen uptake in Escherichia coli by expressing the hydrogenase from the Cyanobacterium synechocystis sp. PCC 6803," BMC Biotechnology., 7:25, May 2007.

Maier et al., "Identification, cloning and heterologous expression of active[ NiFe]-hydrogenase 2 from Citrobacter sp. SG in Escherichia coli," J. Biotechnol., 199:1-8, Apr. 2015.

Mcintosh et al., The [NiFe]-Hydrogenase of the Cyanobacterium synechocystis sp. PCC 6803 Works Bidirectionally with a Bias to H2 Production, J. Am. Chem. Soc., 133, 11308-11319, Jun. 2011.

Nicolet et al., "A novel FeS cluster in Fe-only hydrogenases," 25(3):138-43, Mar. 2000.

Nicolet et al., "Fe-only hydrogenases: structure, function and evolution," J Inorg Biochem., 91(1):1-8, Jul. 2002.

Oliveira et al., "Transcriptional regulation of the cyanobacterial bidirectional Hox-hydrogenase," Dalton Trans., (45):9990-6, Dec. 2009.

Pierik et al., Carbon Monoxide and Cyanide as Intrinsic Ligands to Iron in the Active Site of [NiFe]-Hydrogenases, vol. 274, No. 6, 3331-3337, Feb. 1999.

Pilak et al., "The Crystal Structure of the Apoenzyme of the Iron-Sulphur Cluster-free Hydrogenase," J. Mol. Biol., 358, 798-809, Mar. 2006.

Schiffels et al., "An Innovative Cloning Platform Enables Large-Scale Production and Maturation of an Oxygen-Tolerant [NiFe]-Hydrogenase from Cupriavidus necator in Escherichia coli," PLOS ONE., 8(7): e68812, Jul. 2013.

Schmitz et al., "HoxE—a subunit specific for the pentameric bidirectional hydrogenase complex (HoxEFUYH) of cyanobacteria," Biochimica et Biophysica Acta., 1554, 66-74, Apr. 2002.

Shima et al., "A Third Type of Hydrogenase Catalyzing H2 Activation," The Chemical Record., Chem Rec., 7(1):37-46, Dec. 2006.

Singh et al., "Protein recovery from inclusion bodies of Escherichia coli using mild solubilization process," Microbial Cell Factories., 14:41, Mar. 2015.

Sun et al., "Heterologous Expression and Maturation of an NADP-Dependent [NiFe]-Hydrogenase: A Key Enzyme in Biofuel Production," PLOS ONE., 5(5):e10526, May 2010.

Thauer, Rudolf K., "Biochemistry of methanogenesis : a tribute to Marjory Stephenson," Microbiology., 144, 2377-2406, Mar. 1998.

Van Der Linden et al., "The soluble [NiFe]-hydrogenase from Ralstonia eutropha contains four cyanides in its active site, one of which is responsible for the insensitivity towards oxygen," J Biol Inorg Chem., 9:616-626, May 2004.

Vignais et al., "Classification and phylogeny of hydrogenases," FEMS Micobiology Reviews., 25, 455-501, Jun. 2001.

Vignais et al., "Occurrence, Classification, and Biological Function of Hydrogenases: An Overview," Chem. Rev., 107, 4206-4272, Feb. 2007.

Volbeda et al., "Crystal structure of the nickel-iron hydrogenase from Desulfovibrio gigas," Nature., 373, 580-587, Feb. 1995.

Weyman et al., "Genetic analysis of the Alteromonas macleodii [NiFe]-hydrogenase," FEMS Microbiol Lett., 322, 180-187, Jul. 2011.

Yacoby et al., "Optimized Expression and Purification for High-Activity Preparations of Algal [FeFe]-Hydrogenase," PLoS ONE., 7(4): e35886, Apr. 2012.

* cited by examiner

MONOMER POLYPEPTIDE HAVING HYDROGENASE ACTIVITY, IN PARTICULAR RECOMBINANT MONOMER POLYPEPTIDE HAVING HYDROGENASE ACTIVITY

CROSS-REFERENCE TO RELATED APPLICATIONS

This application is a National Stage filing under 35 U.S.C. § 371 of International Application No. PCT/EP2020/081931 filed Nov. 12, 2020, which claims the benefit of European Patent Application No. 19208856.5 and Belgian Patent Application No. 2019/5783, both filed Nov. 13, 2019, which applications are incorporated herein by reference in their entirety.

SEQUENCE LISTING

The instant application contains a Sequence Listing which has been submitted electronically in ASCII format and is hereby incorporated by reference in its entirety. The ASCII copy, created on Oct. 24, 2019, is named Sequences_listing_ST25-EN.txt and is 4790 bytes in size.

The present invention relates to a monomeric polypeptide having hydrogenase activity, in particular to a recombinant monomeric polypeptide having hydrogenase activity, to a host cell including this monomeric polypeptide and to a host cell including a polynucleotide encoding this monomeric polypeptide. The present invention also relates to a method for obtaining a monomeric polypeptide having hydrogenase activity, in particular to a method for obtaining a recombinant monomeric polypeptide having hydrogenase activity and to the use of such a monomeric polypeptide, in particular to the use of such a recombinant monomeric polypeptide.

The decreasing availability of fossil energy sources and the fear of dramatic climate change have led to the emergence of clean and renewable technologies. Hydrogen ($H_2$) is considered as a promoter renewable energy carrier due to its high energy content and to the absence of greenhouse gas and nanoparticle when used in the fuel cells. The production of $H_2$ is currently carried out by chemical extraction of fossil hydrocarbons, electrolysis of water or pyrolysis of biomass. However, the lack of both non-polluting and commercially viable production systems is a major limitation. The use of methods for the biotechnological production of $H_2$, also called bio-hydrogen, could be a solution. The number of research on the bio-hydrogen production has increased considerably over the last decade. This includes the microbial production mainly through the process of fermentation in bacteria and of photosynthesis in microalgae, but also the enzymatic generation of hydrogen through "electro-enzymology". All of these methods rely on particular enzymes called hydrogenases.

Hydrogenases are metallo-enzymes that catalyze the chemical reaction: $2H^+ + 2e^- \leftrightarrow H_2$. This enzyme-dependent hydrogen production or consumption reaction is defined as hydrogenase activity. The reaction is reversible and its direction depends on the redox potential of the components capable of interacting with the enzyme. In the presence of $H_2$ and of an electron acceptor, a hydrogenase consumes hydrogen. In the presence of a low potential electron donor, a hydrogenase uses protons as electron acceptors and produces $H_2$. Hydrogenases are widespread among microorganisms because many of them use hydrogen as an energy carrier or source. These enzymes have many representatives in the field of bacteria and archaea, and are also present in some unicellular eukaryotic organisms. Despite their diversity in many respects (host, size, quaternary structure, electron donors or acceptors), hydrogenases are divided into three phylogenetically distinct classes: [Fe]-hydrogenases, [FeFe]-hydrogenases and [NiFe]-hydrogenases. Each class is characterized by a distinctive metallic composition of the active site. Physiologically, these enzymes have been shown to function as a valve for excess of electrons.

The catalytic center of [Fe]-hydrogenases does not contain any FeS or Ni center and has therefore been named "iron-sulfur center-free hydrogenase" or [Fe]-hydrogenases (Shima and Thauer. 2007. A third type of hydrogenase catalyzing H2 activation. Chem Rec 7:37-46). [Fe]-hydrogenases are limited to certain methanogenic microorganisms (Pilak et al. 2006. The crystal structure of the apoenzyme of the iron-sulphur cluster-free hydrogenase. J Mol Biol 358: 798-809) where they are essential for growth during a nickel deficiency (Thauer. 1998. Biochemistry of methanogenesis: a tribute to Marjory Stephenson. 1998 Marjory Stephenson Prize Lecture. Microbiology 144:2377-2406). Associated with a specific cofactor, these enzymes have very different catalytic properties from other types of hydrogenases. Indeed, they do not catalyze the reversible $H_2$ production reaction (Vignais and Billoud. 2007. Occurrence, classification, and biological function of hydrogenases: an overview. Chem Rev 107:4206-4272). For this reason, as well as their low distribution, this class of hydrogenases has been little studied. The vast majority of known hydrogenases belong to the other two classes.

[FeFe]-hydrogenases are monomeric enzymes of which the catalytic center is highly conserved. It is a bi-nuclear iron site bound to a [4Fe-4S] center by a cysteine bridge. The non-protein ligands, cyanide (CN) and carbon monoxide (CO), are bound to the iron atoms of the bi-nuclear center. Iron atoms also share two sulfur ligands (Nicolet et al. 2000. A novel FeS cluster in Fe-only hydrogenases. Trends Biochem Sci 25:138-143, Nicolet et al. 2002. Fe-only hydrogenases: structure, function and evolution J Inorg Biochem 91:1-8). Additional domains host multiple FeS centers and provide the electron transfer chain between the external electron source and the active site embedded in these monomeric proteins. In addition, a hydrophobic channel connects the surface to the active site and provides an access for protons and an exit for $H_2$ molecules. Three chaperone proteins named HydE, HydF and HydG are known to be necessary for the correct assembly of [FeFe]-hydrogenases (Vignais et al. 2001. Classification and phylogeny of hydrogenases. FEMS Microbiol Rev 25:455-501). These enzymes are present in anaerobic prokaryotes (genus *Clostridium* or *Desulfovibrio*), but also in some lower eukaryotes such as anaerobic fungi or unicellular microalgae (genus *Chlorella* or *Chlamydomonas*) (Vignais and Billoud. 2007. Occurrence, classification, and biological function of hydrogenases: an overview. Chem Rev 107:4206-4272). [FeFe]-hydrogenases thermodynamically promote the reoxidation of the cofactor (ferredoxin or NADH) and thus generate $H_2$. These enzymes are therefore generally involved in the elimination of an excess of reducing equivalents in the cell in order to avoid, for example, a stop of the fermentation. They are also able to interact with the photosynthetic chain of a restricted group of microalgae to oxidize the photosynthetic chain and thus activate the carbon fixation after an anoxic incubation (Ghysels et al. 2013. Function of the chloroplast hydrogenase in the microalga *Chlamydomonas*: the role of hydrogenase and state transitions during photosynthetic activation in anaerobiosis. PLoS One 8:e64161, Godaux et al. 2015. Induction of Photosynthetic Carbon Fixation in Anoxia Relies on Hydrogenase Activity and Proton-Gradient Regulation-Like1-Mediated Cyclic Electron Flow in *Chlamydomonas reinhardtii*. Plant Physiol 168:648-658).

[NiFe]-hydrogenases form globular hetero-multimers (Volbeda et al. 1995. Crystal structure of the nickel-iron hydrogenase from *Desulfovibrio gigas*. Nature 373:580-587). The bi-metallic [NiFe] active site is located in the large subunit where it is coordinated by four cysteines and three non-protein ligands, one CO molecule and two CNs, bound to the iron atom (Happe et al. 1997. Biological activation of hydrogen. Nature 385:126, Pierik et al. 1999. Carbon monoxide and cyanide as intrinsic ligands to iron in the active site of [NiFe]-hydrogenases. NiFe(CN)2CO, Biology's way to activate H2. J Biol Chem 274:3331-3337). The other subunits of the hetero-multimer contain several medial and distal FeS centers, which conduct electrons between the active site and the physiological electron donor or acceptor. The [4Fe-4S] group located near the active site is considered essential for the activity (Albracht. 1994. Nickel hydrogenases: in search of the active site. Biochim Biophys Acta 1188:167-204). In addition to structural genes, there are several accessory genes involved in the maturation and the insertion of Ni, Fe, CO and CN into the active site of these hetero-multimers. Indeed, the maturation of [NiFe]-hydrogenases follows a complex pathway involving at least seven auxiliary proteins (HypA-F and an endopeptidase) (Vignais and Billoud. 2007. Occurrence, classification, and biological function of hydrogenases: an overview. Chem Rev 107: 4206-4272). Another characteristic of the active site of [NiFe]-hydrogenases is the strong affinity for hydrogen. These enzymes therefore act mainly by consuming $H_2$ in the host microorganism, even if certain [NiFe]-hydrogenases have a good hydrogen production capacity. [NiFe]-hydrogenases are fairly widespread enzymes among prokaryotes with many representatives in bacteria and archaea. The classification of [NiFe]-hydrogenases is based on the amino acid sequence alignments of the different subunits and divides [NiFe]-hydrogenases into four groups. Remarkably, this classification is in good agreement with the groups derived from the physiological functions (Vignais and Billoud. 2007. Occurrence, classification, and biological function of hydrogenases: an overview. Chem Rev 107:4206-4272).

The extreme sensitivity of hydrogenases to oxygen both in vitro and in vivo is a problem when considering these enzymes for the hydrogen production on an industrial level. Oxygen binds as a ligand to the active site, accepts electrons and is reduced to reactive oxygen species (ROS) trapped in the enzyme. This can lead to permanent damage when ROS survives long enough to attack the vulnerable catalytic center. [FeFe]-hydrogenases have severe sensitivity to $O_2$ because the enzyme is irreversibly damaged after exposure to small concentrations of 02 (Ghirardi et al. 1997. Oxygen sensitivity of algal $H_2$– production. Appl Biochem Biotechnol 63-65:141-151). However, [NiFe]-hydrogenases are described as being more resistants than [FeFe]-hydrogenases to damages caused by oxygen. In addition, [NiFe]-hydrogenases are reversibly inactivated by $O_2$. Some microorganisms, such as *Ralstonia* sp., have even developed an oxygen-tolerant active site, and are capable to oxidize hydrogen even in the presence of air (Van der Linden et al. 2004. The soluble [NiFe]-hydrogenase from *Ralstonia eutropha* contains four cyanides in its active site, one of which is responsible for the insensitivity towards oxygen. J Biol Inorg Chem 9:616-626). These diverse characteristics make [NiFe]-hydrogenases better candidates for an industrially viable technological use.

HoxEFUYH is a well characterized [NiFe]-hydrogenase present in the cyanobacterium *Synechocystis* sp. PCC6803. HoxEFUYH is a pentameric and cytoplasmic [NiFe]-hydrogenase. HoxY and HoxH form the "hydrogenase" part while HoxE, HoxF and HoxU constitute the part in contact with the redox cofactor (Carrieri et al. 2011. The role of the bidirectional hydrogenase in cyanobacteria. Bioresour Technol 102:8368-8377). HoxH is the subunit responsible for the catalytic activity, that is to say the subunit comprising the active site of [NiFe]-hydrogenase. HoxH contains the conserved residues for the bonding of nickel and iron atoms. HoxY contains the proximal [4Fe-4S] group near the NiFe catalytic center. HoxF and HoxU are iron-sulfur type proteins responsible for the in vivo interaction with the substrate (NADH, flavodoxin or reduced ferredoxin). HoxFU contain the medial and distal FeS centers transporting electrons to HoxYH. The function of HoxE is unclear, but it may be a membrane-anchoring subunit. A mutational analysis of the maturation pathway has identified seven essential maturation factors, called HypA, HypB, HypC, HypD, HypE, HypF and HoxW (Hoffmann et al. 2006. Mutagenesis of hydrogenase accessory genes of *Synechocystis* sp. PCC 6803. Additional homologs of hypA and hypB are not active in hydrogenase maturation. FEBS J 273:4516-4527). A maturation model of HoxEFUYH has been proposed (Carrieri et al. 2011. The role of the bidirectional hydrogenase in cyanobacteria. Bioresour Technol 102:8368-8377, Cassier-Chauvat et al. 2014. Advances in the function and regulation of hydrogenase in the cyanobacterium *Synechocystis* PCC6803. Int J Mol Sci 15:19938-19951). The HoxH subunit is treated by the HoxW specific protease and the [Ni—Fe] site is added to the catalytic subunit by the HypABCDEF complex. The complete genome of *Synechocystis* sp. PCC6803 has been sequenced. The HoxEFUYH genes were identified as clustered in an octacistronic operon, unlike the hypABCDEF genes scattered in the *Synechocystis* chromosome. The promoter of the hoxEFUYH operon is not very active (Dutheil et al. 2012. The AbrB2 autorepressor, expressed from an atypical promoter, represses the hydrogenase operon to regulate hydrogen production in *Synechocystis* strain PCC6803. J Bacteriol 194:5423-5433). It is regulated by various environmental conditions, such as the availability of hydrogen, light, nitrate, nickel, oxygen or sulfur (Oliveira and Lindblad. 2009. Transcriptional regulation of the cyanobacterial bidirectional Hox-hydrogenase. Dalton Trans 9990-9996). It is important to note that the hox genes are constitutively expressed in the presence of oxygen (Kiss et al. 2009. Transcriptional regulation of the bidirectional hydrogenase in the cyanobacterium *Synechocystis* 6803. J Biotechnol 142:31-37), but that the enzyme, sensitive to oxygen, is therefore inactive under aerobic conditions. The precise physiological function is still debated, but HoxEFUYH would function as a safety valve that dissipates excess of electrons under unfavorable redox conditions, thus maintaining an adequate oxidation/reduction balance in the cell during the fermentation or the photosynthesis (Carrieri et al. 2011. The role of the bidirectional hydrogenase in cyanobacteria. Bioresour Technol 102:8368-8377).

There are a large number of studies on HoxEFUYH. Many characteristics make this enzyme a good candidate for the bio-hydrogen production. First, this [NiFe]-hydrogenase has a bias to the proton reduction (McIntosh et al. 2011. The [NiFe]-hydrogenase of the cyanobacterium *Synechocystis* sp. PCC 6803 works bidirectionally with a bias to $H_2$ production. J Am Chem Soc 133:11308-11319). The operon, and therefore the enzyme, are weakly expressed in *Synechocystis* sp. PCC6803 under aerobic condition (Kiss et al. 2009. Transcriptional regulation of the bidirectional hydrogenase in the cyanobacterium *Synechocystis* 6803. J Biotechnol 142:31-37). The inactivation of HoxEFUYH in the presence of oxygen is total and almost instantaneous. However, HoxEFUYH can be reactivated quickly (delays of the order of one minute) under redox condition (for example by reduction with hydrogen and/or by elimination of oxygen) (Appel et al. 2000. The bidirectional hydrogenase of *Synechocystis* sp. PCC 6803 works as an electron valve during photosynthesis. Arch Microbiol 173:333-338, Germer et al. 2009. Overexpression, isolation, and spectroscopic characterization of the bidirectional [NiFe] hydrogenase from *Synechocystis* sp. PCC 6803. J Biol Chem 284:36462-36472, McIntosh et al. 2011. The [NiFe]-hydrogenase of the cyanobacterium *Synechocystis* sp. PCC 6803 works bidirectionally with a bias to $H_2$ production. J Am Chem Soc 133:11308-11319). Several purification protocols (Schmitz et al. 2002. HoxE—a subunit specific for the petmeric bidirectional hydrogenase complex (HoxEFUYH) of cyanobacteria. Biochim Biophys Acta 1554:66-74, Germer et al. 2009. Overexpression, isolation, and spectroscopic characterization of the bidirectional [NiFe] hydrogenase from *Synechocystis* sp. PCC 6803. J Biol Chem 284: 36462-36472) and implementation in electrochemistry (McIntosh et al. 2011. The [NiFe]-hydrogenase of the cyanobacterium *Synechocystis* sp. PCC 6803 works bidirectionally with a bias to $H_2$ production. J Am Chem Soc 133:11308-11319) are available. The ability to efficiently catalyze the production of hydrogen, and with limited sensitivity to oxygen, allowed HoxEFUYH to be identified as a good candidate.

A common and efficient method for producing a large quantity of a protein of interest is the recombinant production of this protein within a heterologous host. This biotechnological process involves the introduction and the expression of genes of interest into the genome of the host organism in order to produce a large quantity of the protein of interest, with an excellent degree of purity. There are several recombinant production systems. The prokaryotic system remains the fastest and easiest system to produce a protein of interest, the eukaryotic system being slower and more complicated to implement. Each organism has its own advantages and disadvantages. There is not yet a universally applicable expression system. It is very difficult to predict which host will work best for a particular protein or for a particular end use. *Escherichia coli* (*E. coli*) is the reference organism for the recombinant production. Indeed, this bacterium is very well known from the point of view of genetic and physiological engineering, with for example: optimized cell (high productivity, use of codons, inhibition of endogenous proteases), optimized culture medium, short doubling time, low contamination, availability of many commercial vectors, industrial scale-up, high production yield.

The production and the engineering of recombinant hydrogenases, like metalloproteins in general, has had limited success. The literature provides examples of heterologously expressed [FeFe]-hydrogenases in *E. coli* (King et al. 2006. Functional studies of [FeFe] hydrogenase maturation in an *Escherichia coli* biosynthetic system. J Bacteriol 188:2163-2172, Yacoby et al. 2012. Optimized expression and purification for high-activity preparations of algal [FeFe]-hydrogenase PLoS One 7:e35886, Kuchenreuther et al. 2009. Tyrosine, cysteine, and S-adenosyl methionine stimulate in vitro [FeFe] hydrogenase activation. PLoS One 4:e7565). [FeFe]-hydrogenases are monomeric enzymes requiring a limited number of maturation factors.

The heterologous production of [NiFe]-hydrogenases is described as difficult (English et al. 2009. Recombinant and in vitro expression systems for hydrogenases: new frontiers in basic and applied studies for biological and synthetic $H_2$ production. Dalton Trans 9970-9978).

First, the difficulty stems from the complexity and the specificity of the [NiFe] active site assembly process, which theoretically requires at least seven maturation factors for a functional assembly.

Second, the correct folding of each of the subunits of the hetero-multimer is required, which is particularly difficult to control and ensure during a heterologous production.

Third, the correct assembly of each subunit in the hetero-multimeric complex is mandatory. A misfolding can lead to an aggregation phenomena and therefore to a decrease in the amount of active enzyme (Singh et al. 2015. Protein recovery from inclusion bodies of *Escherichia coli* using mild solubilization process. Microb Cell Fact 14:41). Obtaining a precise sequence is necessary to obtain an enzymatic activity, which may be difficult to control and ensure in a heterologous host.

All this explains why [NiFe]-hydrogenases are not always active when produced by heterologous recombination. However, there are several cases in the literature where an active [NiFe]-hydrogenase has been produced in *E. coli* (Kim et al. 2011. Production of biohydrogen by heterologous expression of oxygen-tolerant *Hydrogenovibrio marinus* [NiFe]-hydrogenase in *Escherichia coli* J Biotechnol 155:312-319, Maier et al. 2015. Identification, cloning and heterologous expression of active [NiFe]-hydrogenase 2 from *Citrobacter* sp. SG in *Escherichia coli*. J Biotechnol 199:1-8, Schiffels et al. 2013. An innovative cloning platform enables large-scale production and maturation of an oxygen-tolerant [NiFe]-hydrogenase from *Cupriavidus necator* in *Escherichia coli*. PLoS One 8:e68812, Weyman et al. 2011. Genetic analysis of the *Alteromonas macleodii* [NiFe]-hydrogenase. FEMS Microbiol Lett 322:180-187).

In particular, the work of Sun and these collaborators (Sun et al. 2010. Heterologous expression and maturation of an NADP-dependent [NiFe]-hydrogenase: a key enzyme in biofuel production. PLoS One 5:e10526) has enabled the expression of [NiFe]-hydrogenase from *Pyrococcus furiosus* in anoxia in *E. coli* through four expression vectors allowing the co-expression of 13 heterologous genes (four structural genes and nine maturation factors). More specifically, the work of Sun et al. allowed obtaining a tetrameric recombinant [NiFe]-hydrogenase-like enzyme comprising the four subunits called PF0891, PF0892, PF0893 and PF0894. After purification, this tetrameric recombinant enzyme was found to be functionally similar to the native enzyme purified from *P. furiosus*.

Since HoxEFUYH is a prokaryotic protein of the cyanobacterium *Synechocystis*, the *E. coli* system is suitable for its recombinant production. This production in *E. coli* has already been successfully carried out. In this sense, Maeda and his colleagues showed an in vivo increase in hydrogen production in the *E. coli* cells expressing, under anoxic condition, the cyanobacterial HoxEFUYH enzyme (Maeda et al. 2007. Inhibition of hydrogen uptake in *Escherichia coli* by expressing the hydrogenase from the cyanobacterium *Synechocystis* sp. PCC 6803. BMC Biotechnol 7:25). Such increased hydrogen production in the presence of HoxE-FUYH is due to the inhibition of the activity of the endogenous $H_2$-consuming hydrogenases 1 and 2 in *E. coli*.

We should also mention Wells and his collaborators who introduced the HoxEFUYH genes and these associated maturation factors in *E. coli* (Wells et al. 2011. Engineering a non-native hydrogen production pathway into *Escherichia coli* via a cyanobacterial [NiFe] hydrogenase. Metab Eng 13:445-453). This work demonstrated the production of hydrogen, in anoxia, both in vivo and in vitro via HoxE-FUYH in a null host for the endogenous hydrogenases. They indicate a coupling with host electron transfer systems like fermentation and show the potential of HoxEFUYH in the metabolic engineering to improve the hydrogen production yields.

In the state of the art, there is no disclosure of a monomeric polypeptide including a single subunit comprising the active site of a [NiFe]-hydrogenase-like protein, in particular of an isolated monomer derived from a [NiFe]-hydrogenase-like complex, having on its own hydrogenase activity, even though the documents D2 (Hornhardt et al. 1986. Characterization of a native subunit of the NAD-linked hydrogenase isolated from a mutant of *Alcaligenes eutrophus* $H_{16}$. Biochimie, Masson, Paris, FR, vol. 68(1), pages 15-24) and D3 (Przybyla et al. 1992. Structure-function relationships among the nickel-containing hydrogenases. FEMS Microbiol Rev 8:109-135) seem to believe to make it looks like.

Document D2 describes the characterization of a native subunit of [NiFe]-hydrogenase of *Alcaligenes eutrophus* $H_{16}$. This peptide represents the catalytic subunit of [NiFe]-hydrogenase and is described as completely inactive with NAD as a redox mediator, but having a very low residual activity with methylene blue, ferricyanide and cytochrome C.

Document D3 suggests the existence of [NiFe]-hydrogenase-like monomers having hydrogenase activity. As examples, document D3 mentions, citing document D2, [NiFe]-hydrogenase of *Alcaligenes eutrophus*, and also [NiFe]-hydrogenase-1 of *Escherishia coli*.

However, subsequently published studies, including the studies described in documents D1 (Massanz et al. 1998. Subforms and in vitro reconstitution of the NAD-reducing hydrogenase of *Alcaligenes eutrophus*. J Bacteriol 180: 1023-1029), D4 (Senger et al. 2017. Proteolytic cleavage orchestrates cofactor insertion and protein assembly in [NiFe]-hydrogenase biosynthesis. J Biol Chem 292:11670-11681) and D5 (Pinske et al. 2011. Efficient electron transfer from hydrogen to benzyl viologen by the [NiFe]-hydrogenases of *Escherichia coli* is dependent on the coexpression of the iron-sulfur cluster-containing small subunit. ArchMicrobiol 193:893-903), showed that the conclusions of the studies of documents D2 and D3 are erroneous.

The study described in document D1 demonstrated that the active-site containing subunit of [NiFe]-hydrogenase of *Alcaligenes eutrophus* $H_{16}$ alone had no hydrogenase-like activity with several redox mediators, in particular benzyl-viologen. Document D1 mentions that the smallest entity of [NiFe]-hydrogenase of *Alcaligenes eutrophus* likely to have hydrogenase activity consists of the large subunit containing the [NiFe] center and the small subunit with a minimum of a FeS center. Similarly, the studies presented in documents D4 and D5 contradict the teaching of document D3 by showing that the single catalytic subunit of [NiFe]-hydrogenase-1 of *Escherishia coli* has no hydrogenase activity The majority of the work carried out on this subject, including the studies of documents D1, D4 and D5 consider that the [4Fe-4S] center located in the small subunit is essential and indispensable for the hydrogenase activity of the large subunit of [NiFe]-hydrogenases (Albracht. 1994. Nickel hydrogenases: in search of the active site. Biochim Biophys Acta 1188:167-204). Furthermore, the structural analyzes of [NiFe]-hydrogenases have largely demonstrated the absence of a FeS center in the catalytic subunit containing the active site (Lubitz et al. 2014. Hydrogenases. Chem Rev 114:4081-4148), Thus, the results described previously in document D2 can only be explained by a contamination of the catalytic subunit by the small subunit, as evidenced by the highlight of FeS center in the preparations allowing the low hydrogenase activity measured.

In conclusion, all of the works carried out which constitute the state of the art considers that the reduction in the number of subunits is neither favorable to the activity nor to the stability of hydrogenases and that the NiFe-center containing subunit, isolated from the multimeric complexes of NiFe-like hydrogenases, has no hydrogenase activity on its own.

Unfortunately, as is apparent in particular from the state of the art mentioned above, there remain several drawbacks considerably hampering the use of [NiFe]-hydrogenases, and in particular the use of HoxEFUYH, for a bio-production of hydrogen commercially profitable.

To date, there is therefore a real need to overcome the obstacles hindering the use of [NiFe]-hydrogenases for a hydrogen production since, as indicated above, [NiFe]-hydrogenases undeniably have a high potential for the production of hydrogen.

To solve these problems, here is provided in accordance with the invention a monomeric polypeptide including a single subunit comprising the active site of a [NiFe]-hydrogenase-like protein, said monomeric polypeptide having an enzymatic activity, in particular a hydrogenase-like enzymatic activity, more particularly a catalytic activity, yet more particularly a hydrogenase-like catalytic activity.

Preferably, according to the invention, said monomeric polypeptide comprises a single subunit comprising the active site of a [NiFe]-hydrogenase-like protein.

Preferably, according to the invention, said monomeric polypeptide consists of a single subunit comprising the active site of a [NiFe]-hydrogenase-like protein.

Preferably, according to the invention, said monomeric polypeptide is made of a single subunit comprising the active site of a [NiFe]-hydrogenase-like protein.

In other words, preferentially, here is provided according to the invention, a monomeric polypeptide including a single subunit comprising only the active site of a [NiFe]-hydrogenase-like protein, said monomeric polypeptide having on its own an enzymatic activity, in particular a hydrogenase-like enzymatic activity, more particularly a catalytic activity, yet more particularly a hydrogenase-like catalytic activity.

In the context of the present invention, it has been highlighted that such a monomeric polypeptide including a single subunit comprising the active site of a [NiFe]-hydrogenase-like protein and having hydrogenase activity allows to set free, at least in part, of the obstacles hindering the use of [NiFe]-hydrogenases for a hydrogen production, this while guaranteeing a hydrogenase activity of at least 0.01 $\mu$mol $H_2 \cdot min^{-1} \cdot mg^{-1}$ of enzyme, preferably at least 0.05 $\mu$mol $H_2 \cdot min^{-1} \cdot mg^{-1}$ of enzyme.

Indeed, since it is according to the invention a monomeric polypeptide including a single subunit comprising the active site of a [NiFe]-hydrogenase-like protein, the difficulties encountered with [NiFe]-hydrogenases, in particular to ensure the assembly of the active site, to ensure an adequate folding of each of the involved subunits and to ensure a correct assembly of each subunit in a hetero-multimeric complex, are greatly reduced or even eliminated. This allows increasing the reproducibility during the process of obtaining [NiFe]-hydrogenase since only one subunit is involved. Indeed, the production of a single monomeric polypeptide greatly simplifies the complex process of folding in comparison with the dimeric, tetrameric and pentameric enzymes for which a correct assembly of the active site, of each of the subunits and finally of the entire enzyme is particularly difficult to control and to guarantee, which constitutes an obstacle to their use. According to the invention, the proper folding of a single subunit is necessary and no assembly between different subunits is required to form a hetero-multimeric complex.

Moreover, it has been highlighted that the method for manufacturing such a monomeric polypeptide according to the invention can be completely carried out under aerobic condition (no precaution required with respect to oxygen during the expression and purification steps), which avoids the problems encountered with the methods for manufacturing the recombinant dimeric, tetrameric and pentameric [NiFe]-hydrogenases encountered in the state of the art and for which the manufacturing methods are carried out in anoxia. As mentioned above, even if the accumulation of biomass is carried out in the presence of oxygen, the production phase of the recombinant hydrogenase is itself carried out in anoxia according to the methods known from the state of the art (Sun and al. 2010. Heterologous expression and maturation of an NADP-dependent [NiFe]-hydrogenase: a key enzyme in biofuel production. PLoS One 5:e10526, Wells et al. 2011. Engineering a non-native hydrogen production pathway into Escherichia coli via a cyanobacterial [NiFe] hydrogenase. Metab Eng 13:445-453). The absence of oxygen is also reported (anoxia box, sodium dithionite in the buffers) during the various chromatographic steps of the purification. Maintaining such a level of anoxia during the method obviously involves an increase in the costs associated with the recombinant production, which is solved by the present invention.

Advantageously in accordance with the invention, the size of the monomeric polypeptide according to the invention is clearly smaller in comparison with hetero-multimer, an increase in the mass activity of the enzyme (number of catalytically active entity per mg of total protein) being thus obtained.

A better integration and a densification of the enzymatic catalyst is also achievable, for example, during an electrochemical implementation of the monomeric polypeptide according to the invention, such as for example in a fuel cell.

In addition, the three-dimensional structure of a monomeric polypeptide according to the invention is easily modelable in particular to determine the residues exposed at the surface of the protein, for example to facilitate the orientation as well as the adsorption relative to an interface, for example relative to a carbon electrode. This characteristic advantageously allows, for example, improving the stability of the link between the interface and the enzymatic catalyst, but also optimizing the direct electron transfer between the interface and the active site. The energy efficiency is therefore improved in the absence of additional redox relays, which limits energy losses.

In the context of the present invention, it has also been demonstrated that the monomeric polypeptide is indeed active and suitable for the catalytic production of $H_2$ (for example via the standard in-vitro $H_2$ production test by the hydrogenases using the reduced methyl-viologen as redox mediator) as well as for the catalytic consumption of $H_2$ (for example via the standard in-vitro $H_2$ consumption test by the hydrogenases using oxidized benzyl viologen as redox mediator), without the presence of the proximal FeS center present in the small subunit and described as essential, nor for that matter any other redox relay. This is quite surprising since such a thorough simplification of the hetero-multimeric enzyme has never allowed the highlighting of hydrogenase activity in the state of the art.

All the more advantageously, whereas only a limited $H_2$ production is currently obtained with the known recombinant [NiFe]-hydrogenases (Sun et al. 2010. Heterologous expression and maturation of an NADP-dependent [NiFe]-hydrogenase: a key enzyme in biofuel production. PLoS One 5:e10526, Schiffels et al. 2013. An innovative cloning platform enables large-scale production and maturation of an oxygen-tolerant [NiFe]-hydrogenase from Cupriavidus necator in Escherichia coli. PLoS One 8:e68812, Maier et al. 2015. Identification, cloning and heterologous expression of active [NiFe]-hydrogenase 2 from Citrobacter sp. SG in Escherichia coli. J Biotechnol 199:1-8), it was shown that the monomeric polypeptide according to the invention has hydrogenase activity at least equivalent or even greater than those obtained with the known (recombinant) [NiFe]-hydrogenases.

According to one embodiment in accordance with the invention, the monomeric polypeptide is isolated from its natural environment, in particular isolated from a [NiFe]-hydrogenase-like natural protein.

By way of example, according to the invention, said monomeric polypeptide can be derived/isolated from a prokaryote. Examples include, but are not limited to a member of the genus Escherichia (such as for example Escherichia coli), a member of the genus Desulfovibrio (such as for example Desulfovibrio gigas), a member of the genus Hydrogenophilus (such as for example Hydrogenophilus thermoluteolus), a member of the genus Desulfomicrobium (such as for example Desulfomicrobium baculatum), Synechocystis (such as for example Synechocystis sp. PCC6803), a member of the genus Phormidium (such as for example Phormidium ambiguum) or a member of the genus Spirulina (such as for example Spirulina platensis). For example, said monomeric polypeptide can be derived from a cell or a microbe or can be produced in vitro or in vivo.

According to one embodiment in accordance with the invention, the monomeric polypeptide is recombinant or heterologous.

Advantageously, according to the invention, the monomeric polypeptide is purified.

Preferentially, according to the invention, the monomeric polypeptide has a truncated or non-truncated amino acid sequence having at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the amino acid sequence of SEQ ID NO:2 and/or with the amino acid sequence of SEQ ID NO:4.

Even more preferably, according to the invention, the monomeric polypeptide has a truncated or non-truncated amino acid sequence having at least 81% identity, at least 82% identity, at least 83% identity, at least 84% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, with the amino acid sequence of SEQ ID NO:2 and/or with the amino acid sequence of SEQ ID NO:4.

Advantageously, according to the invention, said monomeric polypeptide is characterized in that said subunit comprising the active site of a [NiFe]-hydrogenase-like protein is the HoxH subunit of HoxEFUYH [NiFe]-hydrogenase-like protein in/from *Synechocystis* sp. PCC6803.

Preferably, according to the invention, said monomeric polypeptide has hydrogenase activity of at least 0.01 μmol $H_2 \cdot min^{-1} \cdot mg^{-1}$ of enzyme, preferably at least 0.05 μmol $H_2 \cdot min^{-1} \cdot mg^{-1}$ of enzyme, preferentially at least 10 μmol $H_2 \cdot m^1 \cdot mg^{-1}$ of enzyme.

The present invention also relates to a host cell including a monomeric polypeptide according to the invention, said monomeric polypeptide including a single subunit comprising the active site of a [NiFe]-hydrogenase-like protein, said monomeric polypeptide having hydrogenase activity.

Preferentially, the present invention relates to a host cell including a monomeric polypeptide according to the invention the subunit of which comprising the active site of a [NiFe]-hydrogenase-like protein is the HoxH subunit of the HoxEFUYH [NiFe]-hydrogenase-like protein in/from *Synechocystis* sp. PCC6803.

By way of example, according to the invention, the host cell, in particular for the expression of said monomeric polypeptide, may be a host bacterial cell of the genus *Escherichia* (such as for example *Escherichia coli*), of the genus *Bacillus* (such as for example *Bacillus subtilis*), of the genus *Streptomyces* (such as for example *Streptomyces coelicolor*), of the genus *Synechocystis* (such as for example *Synechocystis* sp. PCC6803), of the genus *Synechococcus* (such as for example *Synechococcus* WH8102), or any other prokaryotic cell, an eukaryotic cell for example of the genus *Chlamydomonas* (such as for example *Chlamydomonas reinhardtii*), of the genus *Saccharomyces* (such as for example *Saccharomyces cerevisiae*), of the *Pichia* type (such as for example *Pichia pastoris*), or another type of eukaryotic cell.

According to the invention, said monomeric polypeptide included in said host cell may itself, but not necessarily, be derived from the expression of a gene included in an expression vector, for example in a plasmid inserted into said host cell.

Advantageously, according to the invention, said monomeric polypeptide included in said host cell has a truncated or non-truncated amino acid sequence having at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the amino acid sequence of SEQ ID NO:2 and/or with the amino acid sequence of SEQ ID NO:4.

Preferably, according to the invention, said host cell may include one or more maturation factors of said [NiFe]-hydrogenase-like protein, preferably one or more maturation factors of said [NiFe]-hydrogenase-like protein selected from the group consisting of the maturation factors HypA, HypB, HypC, HypD, HypE, HypF and HoxW a) the respective amino acid sequences of which each have at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, respectively with the amino acid sequences of SEQ ID NO:6, SEQ ID NO:8, SEQ ID NO:10, SEQ ID NO:12, SEQ ID NO:14, SEQ ID NO:16, SEQ ID NO:18; or b) encoded together by a concatenary nucleotide sequence having at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the nucleotide sequence of SEQ ID NO:19, which encodes all of these maturation factors.

According to the invention, said at least one maturation factor can be endogenous to the host cell and/or exogenous to the host cell.

Advantageously, for a host cell according to the invention, said monomeric polypeptide and/or said at least one maturation factor is/are derived from the expression of at least one gene included in an expression vector, said expression vector being included in said host cell.

The present invention also relates to a host cell including a polynucleotide encoding a monomeric polypeptide according to the invention including a single subunit comprising the active site of a [NiFe]-hydrogenase-like protein, said monomeric polypeptide having hydrogenase activity.

Preferentially, the present invention relates to a host cell including a polynucleotide encoding a monomeric polypeptide the subunit of which comprising the active site of a [NiFe]-hydrogenase-like protein is the HoxH subunit of the HoxEFUYH [NiFe]-hydrogenase-like protein in/from *Synechocystis* sp. PCC6803.

Preferably, according to the invention, said polynucleotide encoding a monomeric polypeptide has a nucleotide sequence having at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, respectively with the sequences, with the nucleotide sequences of SEQ ID NO:1 and/or SEQ ID NO:3.

By way of example, according to the invention, the host cell including a polynucleotide encoding a monomeric polypeptide according to the invention, and being used in particular for the expression of said monomeric polypeptide, can be a host bacterial cell of the genus *Escherichia* (such as for example *Escherichia coli*), of the genus *Bacillus* (such as for example *Bacillus subtilis*), of the genus *Streptomyces* (such as for example *Streptomyces coelicolor*), a photosynthetic bacterial cell of the genus *Synechocystis* (such as for example *Synechocystis* sp. PCC6803) or *Synechococcus* (such as for example *Synechococcus* WH8102) or any other prokaryotic cell, an eukaryotic cell for example of the genus *Chlamydomonas* (such as for example *Chlamydomonas reinhardtii*), of the genus *Saccharomyces* (such as for example *Saccharomyces cerevisiae*), of the *Pichia* type (such as for example *Pichia pastoris*), or another type of eukaryotic cell.

According to the invention, said polynucleotide included in said host cell may itself but not necessarily be included in an expression vector, for example in a plasmid, inserted into said host cell.

Advantageously, according to the invention, said monomeric polypeptide encoded by said polynucleotide included in said host cell has a truncated or non-truncated amino acid sequence having at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the amino acid sequence of SEQ ID NO:2 and/or with the amino acid sequence of SEQ ID NO:4.

Preferably, according to the invention, said host cell including a polynucleotide encoding a monomeric polypeptide can include one or more maturation factors of said [NiFe]-hydrogenase-like protein, preferably one or more maturation factors of said [NiFe]-hydrogenase-like protein selected from the group consisting of the maturation factors HypA, HypB, HypC, HypD, HypE, HypF and HoxW a) the respective amino acid sequences of which each have at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, respectively with the amino acid sequences of SEQ ID NO:6, SEQ ID NO:8, SEQ ID NO:10, SEQ ID NO:12, SEQ ID NO:14, SEQ ID NO:16, SEQ ID NO:18; or b) encoded together by a concatenary nucleotide sequence having at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the nucleotide sequence of SEQ ID NO:19, which encodes all of these maturation factors.

According to the invention, said at least one maturation factor can be endogenous to the host cell and/or exogenous to the host cell.

Advantageously, for a host cell according to the invention, said monomeric polypeptide and/or said at least one maturation factor is/are derived from the expression of at least one gene included in an expression vector, said expression vector being included in said host cell.

The present invention also relates to a method for obtaining, for example in a host cell (for example in *E. coli*), a monomeric polypeptide having a hydrogenase activity according to the invention, said method comprising the following steps:

modification of an expression vector, for example a plasmid, by including therein an exogenous polynucleotide at least part of which ecodes a monomeric polypeptide including a single subunit comprising the active site of a [NiFe]-hydrogenase-like protein; and incubation of said modified expression vector according to incubation conditions allowing sustaining an expression of said exogenous polynucleotide to produce a monomeric polypeptide including a single subunit comprising the active site of a [NiFe]-hydrogenase-like protein, said monomeric polypeptide having hydrogenase activity.

The method according to the invention allows realizing a production of a single subunit comprising the active site of a [NiFe]-hydrogenase-like protein.

The person skilled in the art is of course able to define the required and appropriate incubation conditions.

According to the invention, during the step of genetically modifying a host cell, the polynucleotide can itself but not necessarily be included in an expression vector, for example in a plasmid.

Advantageously, according to the invention, said step of modifying said expression vector consists of an inclusion in said expression vector of said exogenous polynucleotide at least part of which encodes said monomeric polypeptide the truncated or not-truncated amino acid sequence of which has at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the amino acid sequence of SEQ ID NO:2 and/or with the amino acid sequence of SEQ ID NO:4.

Preferably, according to the invention, said step of modifying said expression vector may comprise the inclusion in said expression vector of one or more maturation factors of said [NiFe]-hydrogenase-like protein, preferably of one or more maturation factors of said [NiFe]-hydrogenase-like protein selected from the group consisting of the maturation factors HypA, HypB, HypC, HypD, HypE, HypF and HoxW a) the respective amino acid sequences of which each have at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, respectively with the amino acid sequences of SEQ ID NO:6, SEQ ID NO:8, SEQ ID NO:10, SEQ ID NO:12, SEQ ID NO:14, SEQ ID NO:16, SEQ ID NO:18; or b) encoded together by a concatenary nucleotide sequence having at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the nucleotide sequence of SEQ ID NO:19, which encodes all of these maturation factors.

According to the invention, during the step of modifying said expression vector, a sequence encoding one or more maturation factors of said [NiFe]-hydrogenase-like protein can itself but not necessarily be included in an expression vector, for example in a plasmid.

Advantageously, the method according to the invention comprises a subsequent step of isolation and/or purification of said monomeric polypeptide.

In particular and preferably, the invention relates to a method for obtaining a monomeric polypeptide having hydrogenase activity according to the invention, said method comprising the following steps:

a step of genetic modification, carried out in-vivo or in-vitro, of an entity comprising a genetic material, for example of a host cell or of an expression vector, to obtain a genetically modified entity, for example a genetically modified host cell or a genetically modified expression vector;

a step of incubating said genetically modified entity, for example said genetically modified host cell or said genetic expression vector, to obtain a monomeric polypeptide including a single subunit comprising the active site of a [NiFe]-hydrogenase-like protein, said monomeric polypeptide having hydrogenase activity.

Preferentially, according to the invention, said step of genetic modification, carried out in-vivo or in-vitro, consists:

a) of a genetic modification of a host cell and/or of an expression vector by including therein an exogenous polynucleotide at least part of which encodes a monomeric polypeptide including a single subunit comprising the active site of a [NiFe]-hydrogenase-like protein, to obtain a genetically modified host cell and/or a genetically modified expression vector to be incubated during said incubation step carried out according to incubation conditions allowing sustaining an expression of said exogenous polynucleotide to produce said monomeric polypeptide; or b) of inducing at least one genetic mutation in the genetic material of a host cell to obtain a genetically modified host cell to be incubated during said incubation step carried out according to incubation conditions to produce said monomeric polypeptide.

The person skilled in the art is of course able to define the required and appropriate incubation conditions.

For example, according to the invention, said induction of at least one genetic mutation is performed by homologous recombination, a method well known to those skilled in the art.

Advantageously, according to the invention, said step of genetic modification of said host cell by inclusion of an exogenous polynucleotide consists of an inclusion in said host cell of an expression vector, in particular of a modified expression vector, including said exogenous polynucleotide.

Preferably, according to the invention, said step of genetic modification of said host cell consists of an inclusion in said host cell of said exogenous polynucleotide at least part of which encodes said monomeric polypeptide, the truncated or non-truncated amino acid sequence of which has at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the amino acid sequence of SEQ ID NO:2 and/or with the amino acid sequence of SEQ ID NO:4.

Advantageously, according to the invention, said step of genetic modification of said host cell further comprises the inclusion in said host cell of at least one maturation factor of said [NiFe]-hydrogenase-like protein, said at least one factor maturation being endogenous to the host cell and/or exogenous to the host cell, preferably the inclusion of at least one maturation factor of said [NiFe]-hydrogenase-like protein selected from the group consisting of maturation factors HypA, HypB, HypC, HypD, HypE, HypF and HoxW a) the respective amino acid sequences of which each have at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, respectively with the amino acid sequences of SEQ ID NO:6, SEQ ID NO:8, SEQ ID NO:10, SEQ ID NO:12, SEQ ID NO:14, SEQ ID NO:16, SEQ ID NO:18; ou b) encoded together by a concatenary nucleotide sequence having at least 15% identity, preferably at least 20% identity, more preferentially at least 40% identity, more preferentially still at least 60% identity, more preferentially still at least 80% identity, more preferentially still at least 90% identity, more preferentially still at least 95% identity, more preferentially still at least 99% identity, with the nucleotide sequence of SEQ ID NO:19, which encodes all of these maturation factors.

Preferably, according to the invention, said at least one maturation factor is derived from the expression of at least one gene included in an expression vector, said expression vector being included in said host cell.

Preferentially, the method for obtaining a monomeric polypeptide having hydrogenase activity according to the invention gives rise to the obtention of a monomeric polypeptide the subunit of which comprising the active site of a [NiFe]-hydrogenase-like protein is the HoxH subunit of the HoxEFUYH [NiFe]-hydrogenase-like protein in *Synechocystis* sp. PCC6803.

The present invention also relates to a use of a monomeric polypeptide in accordance with the invention including a single subunit comprising the active site of a [NiFe]-hydrogenase-like protein, said monomeric polypeptide having hydrogenase activity and being present or not in a cell, to produce or consume hydrogen by incubating said monomeric polypeptide according to incubation conditions allowing ensuring a production or consumption of hydrogen.

The present invention also relates to a use of a monomeric polypeptide in accordance with the invention or of a monomeric polypeptide obtained according to the method in accordance with the invention including a single subunit comprising the active site of a [NiFe]-hydrogenase-like protein, said monomeric polypeptide having hydrogenase activity and being present or not in a cell, for coating a surface, in particular for coating a surface of an electrical conductor, for example for coating a surface of an anode or a cathode.

Definitions

The term "polypeptide", refers, within the meaning of the present invention, to a single chain composed of a minimum of two amino acids linked together by a peptide bond between the carboxylic group of an amino acid and the amine group of the next amino acid. The term "polypeptide" also includes molecules which contain more than one polypeptide, these linked together, for example by disulfide bridges, or complexes of polypeptides, these linked together, for example non-covalently or covalently, and forming a multimer (for example dimer, trimer, quadrimer, pentamer). A polypeptide can also contain non-protein ligands, such as inorganic iron (Fe), nickel (Ni), iron-sulfur center (FeS), or other organic ligand such as carbon monoxide (CO), cyanide (CN) or flavin. The terms peptide, polypeptide, enzyme, subunit or protein are all included in the definition of the polypeptide and these terms may be interchangeable. The definition of "polypeptide" does not take into account the length of said polypeptide nor the way in which said polypeptide is produced.

The term "recombinant polypeptide" or "heterologous polypeptide", refers, within the meaning of the present invention, to a polypeptide which is not naturally present in the environment and/or which is not naturally present in the host cell used for its production, in particular in a host cell, and whose production is carried out by recombinant techniques, for example by adding genetic material to a host cell.

The terms "monomeric polypeptide", refer, within the meaning of the present invention, to a single chain composed of a minimum of two amino acids linked together by a peptide bond between the carboxylic group of an amino acid and the amine group of the next amino acid. As opposed to the term "polypeptide", the term "monomeric polypeptide" includes only molecules which contain only one polypeptide, that is to say without interaction with any other polypeptide. For example, it is in no way a multimer (for example dimer, trimer, quadrimer, pentamer, . . . ). A monomeric polypeptide can also contain non-protein ligands, such as inorganic iron (Fe), nickel (Ni), iron-sulfur centers (FeS), or other organic ligand such as carbon monoxide (CO), cyanide (CN) or flavin. The definition of "monomeric polypeptide" does not take into account the length of said polypeptide nor the way in which said polypeptide is produced.

The terms "recombinant monomeric polypeptide" or "heterologous monomeric polypeptide", mean, within the meaning of the present invention, that the monomeric polypeptide is not naturally present in the environment, in particular in a host cell, and whose production is carried out by recombinant techniques, for example by adding genetic material to a host cell.

The terms "monomeric polypeptide having hydrogenase activity" mean, within the meaning of the present invention, that the monomeric polypeptide is able to catalyze the reversible reaction $H_2 \leftrightarrow 2H^+ + 2e^-$. This definition of hydrogenase activity is not related to the experimental conditions but only to the production or consumption of hydrogen through the enzymatic activity of hydrogenase.

The terms "active site", refer, within the meaning of the present invention, to the part of polypeptide which, when the tertiary structure is formed, is responsible for the catalytic activity of said polypeptide, for example for the hydrogenase activity. The part of polypeptide can comprise, for example, several portions of the amino acid sequence and/or the binding with one or more non-protein ligands.

The term "polynucleotide", refers, within the meaning of the present invention, to a single chain composed of a minimum of two nucleotides linked together, for example by a covalent bond, regardless of whether they are ribonucleotides or deoxynucleotides. This therefore includes single-stranded or double-stranded RNAs and DNAs. The definition of "polynucleotide" does not take into account the length of said polynucleotide, nor the function, nor the shape, nor the way in which said polynucleotide is produced. A polynucleotide can be, for example, plasmid, part of plasmid, gene or gene fragment.

The terms "exogenous polynucleotide", refer, within the meaning of the present invention, to a polynucleotide which is not normally present in the host cell. For example, the exogenous polynucleotide can be a sequence encoding a polypeptide that is not naturally present in the host cell or a plasmid.

The term "concatenary", refers, within the meaning of the present invention, to a stretch of several sequences in order to form only one, for example of polynucleotide sequences or polypeptide sequences.

The term "plasmid", refers, within the meaning of the present invention, to a molecule of double-stranded DNA distinct from exogenous chromosomal DNA, capable of autonomous replication, thanks to its own origin of replication. The plasmid may also include other sequences of interest, such as a gene encoding a selection factor (resistance to an antibiotic, etc.), a multiple cloning site allows the addition of polynucleotide, and/or transcriptional regulation sequences. The terms "plasmid" or "expression vector" are interchangeable.

The term "host cell", refers, within the meaning of the present invention, to a cell which has undergone a modification. This modification can for example be the introduction of an exogenous polynucleotide into the cell, for example through a plasmid.

The terms "maturation factor", refer, within the meaning of the present invention, to any biological or non-biological molecule, which participates in the formation of the structure of another biological molecule, for example of protein.

The terms "endogenous maturation factor", refer, within the meaning of the present invention, to any biological or non-biological molecule, which participates in the formation of the structure of another biological molecule, for example of a protein, and which is naturally present in the host cell, that is to say without genetic modification of said host cell.

The terms "exogenous maturation factor", refer, within the meaning of the present invention, to any biological or non-biological molecule, which participates in the formation of the structure of another biological molecule, for example of a protein, and which is not naturally present in the host cell, that is to say that a genetic modification of said host cell is necessary to add said exogenous maturation factor thereto, for example by adding an expression vector.

The term "isolated", refers, within the meaning of the present invention, to any molecule which has been removed from its natural environment, for example which has been removed from a natural [NiFe]-hydrogenase.

The term "purified", refers, within the meaning of the present invention, to any molecule which has been secluded through biochemical techniques. This definition does not take into account the way in which the molecule is produced, for example naturally or by recombination, chemically or enzymatically synthesized, nor the biochemical techniques implemented for the purification, such as affinity chromatography or molecular sieve. For example, a polynucleotide, a polypeptide or $H_2$ can be purified. Preferentially, a substance is purified when it represents at least 60% relative to the other components associated therewith, preferentially 75% relative to the other components associated therewith, preferentially 90% relative to the other components associated therewith.

The term "apparent homogeneity", refers, within the meaning of the present invention, to any purified molecule representing at least 90% relative to the other components associated therewith.

The term "identity", refers, within the meaning of the present invention, to a structural similarity between two polynucleotides or two polypeptides. The structural similarity is determined by an alignment between the two sequences, alignment which optimizes the number of identical nucleotides or the number of identical amino acids along the sequence. The holes in one or both sequences are allowed in order to optimize the alignment and therefore the structural similarity. The sequences of the nucleotides or of the amino acids must however remain the same.

The terms "genetic material", refer, within the meaning of the present invention, to the genome of an entity and more precisely to all the nucleic acids of this entity, coding and non-coding sequences included.

The terms "genetic mutation", refer, within the meaning of the present invention, to an accidental or provoked modification of the genetic material of an entity, for example of a host cell or of an expression vector.

The terms "entity comprising genetic material", refer, within the meaning of the present invention, to an entity which comprises genetic material according to the definition given above, for example a host cell or an expression vector such as plasmid.

The terms "genetically modified entity", refer, within the meaning of the present invention, to an entity comprising genetic material according to the definition given above and which has undergone a modification of its genetic material, for example a genetic mutation or the introduction of an exogenous polynucleotide into the cell, such as through plasmid.

The terms "genetically modified host cell", refer, within the meaning of the present invention, to a host cell according to the definition given above and which has undergone a modification of its genetic material, for example a genetic mutation or the introduction of an exogenous polynucleotide into the cell, such as through plasmid.

The terms "genetically modified expression vector", refer, within the meaning of the present invention, to an expression vector or a plasmid according to the definition given above and which has undergone a modification of its genetic material, for example the addition of a sequence of interest, such as a gene encoding a particular polypeptide.

Other characteristics, details and advantages of the invention will emerge from the examples given below, not by way of limitation and with reference to the appended figures.

Figure 7:
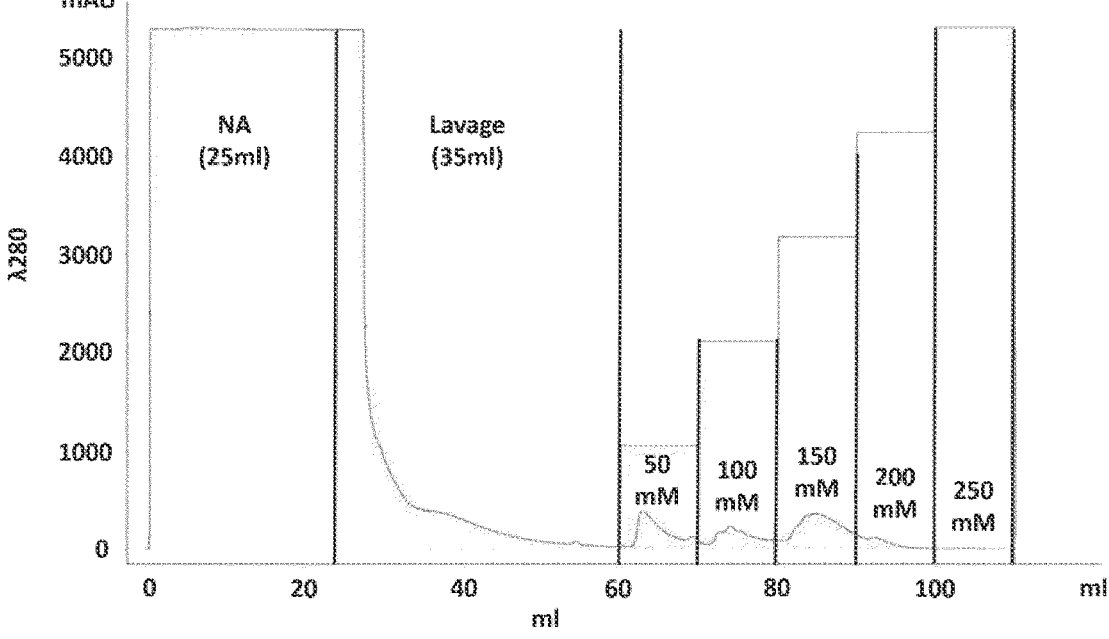

FIG. 7 illustrates the method of purification of the HoxH recombinant protein of interest. NA, sample not absorbed on the Ni-NTA affinity column. Wash, sample eluted with the wash buffer containing 10 mM Imidazole. 50 mM, sample eluted at a concentration of 50 mM imidazole. 100 mM, sample eluted at a concentration of 100 mM imidazole. 150 mM, sample eluted at a concentration 150 mM imidazole. 200 mM, sample eluted at a concentration of 200 mM imidazole. 250 mM, sample eluted at a concentration of 250 mM imidazole.

Figure 8:
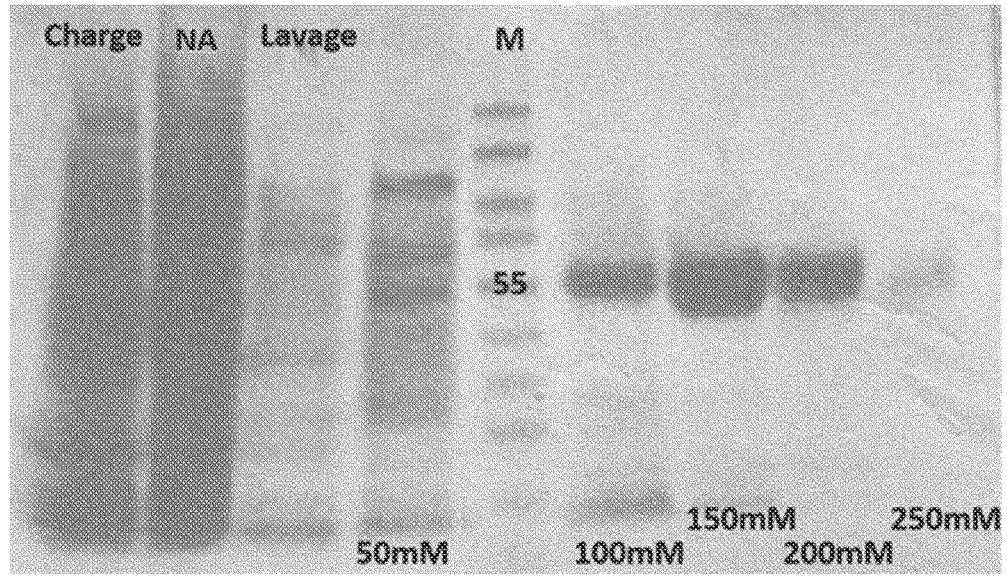

FIG. 8 illustrates the SDS-PAGE analysis of the protein composition of various fractions collected during the affinity chromatography. Load, supernatant applied to the Ni-NTA affinity column and derived from the lysis of the recombinant *E. coli* cells; NA, sample not absorbed on the Ni-NTA affinity column. Wash, sample eluted with the wash buffer containing 10 mM Imidazole. M, molecular weight marker. 50 mM, sample eluted at a concentration of 50 mM imidazole. 100 mM, sample eluted at a concentration of 100 mM imidazole. 150 mM, sample eluted at a concentration of 150 mM imidazole. 200 mM, sample eluted at a concentration of 200 mM imidazole. 250 mM, sample eluted at a concentration of 250 mM imidazole.

Figure 9:
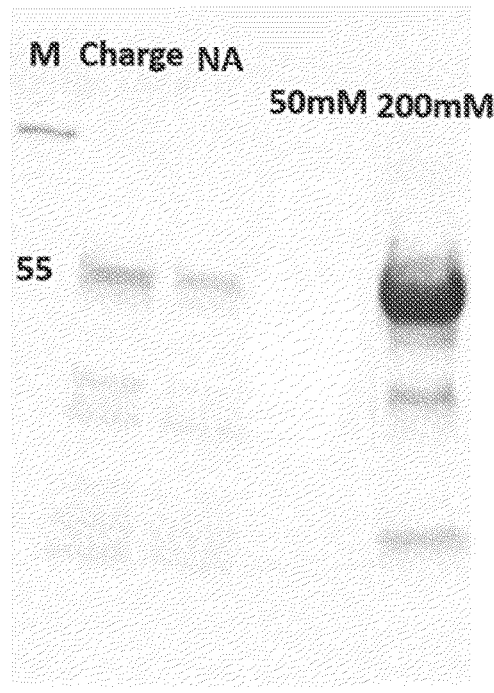

FIG. 9 illustrates the immuno-detection analysis (Western blot) of the presence of HoxH in various fractions collected during the affinity chromatography. M, molecular weight marker. Load, supernatant applied to the Ni-NTA affinity column and derived from the lysis of the recombinant *E. coli* cells. NA, sample not absorbed on the Ni-NTA affinity column; 50 mM, sample eluted at a concentration of 50 mM imidazole. 200 mM, sample eluted at a concentration of 200 mM imidazole.

Figure 10:
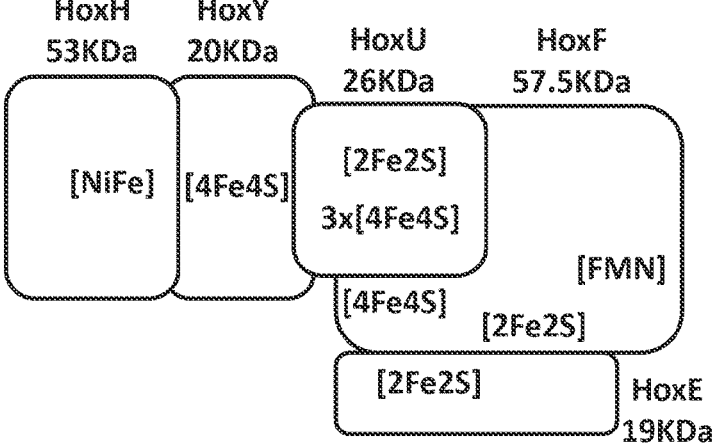

FIG. 10 is a schematic representation of the structure of HoxEFUYH, [NiFe]-hydrogenase from *Synechocystis* sp. PCC 6803. HoxE, 19 KDa and 1 FeS center; HoxF, 57.5 KDa, 2 FeS centers and a FMN center; HoxU, 26 KDa and 4 FeS centers; HoxY, 20 KDa and a FeS center; HoxH, 53 KDa and the active site.

Figure 11:
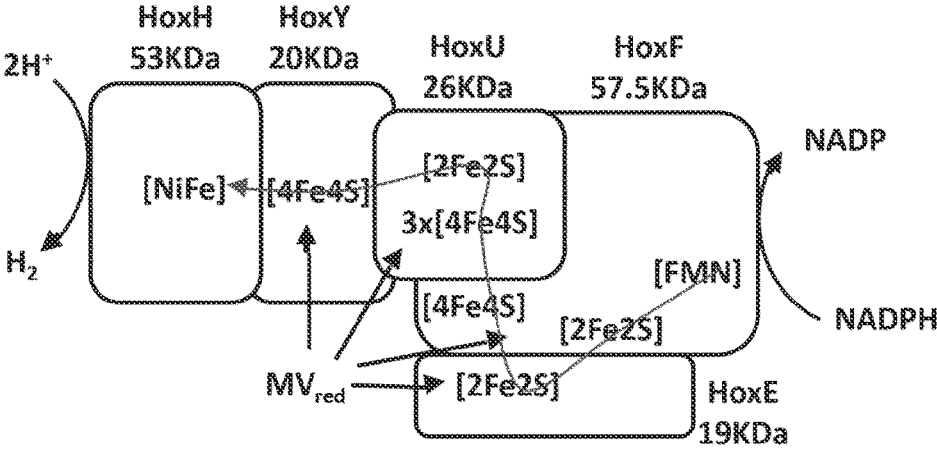

FIG. 11 is a schematic representation (shaded arrow) of the electron transfer and the expected interactions with NADPH and methyl-viologen (MV) in HoxEFUYH, [NiFe]-hydrogenase from *Synechocystis* sp. PCC 6803.

Figure 12:
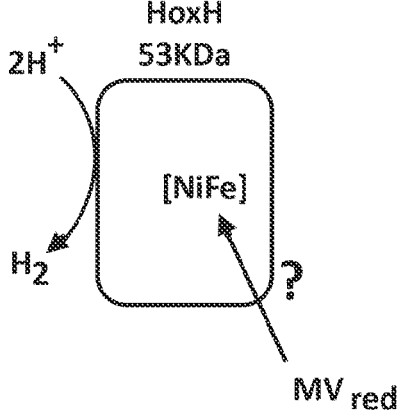

FIG. 12 is a schematic representation where the question mark raises the question whether or not the active site of the HoxH recombinant protein can accept electrons directly from MV and therefore produce hydrogen in the absence of additional redox relays.

Figure 13:
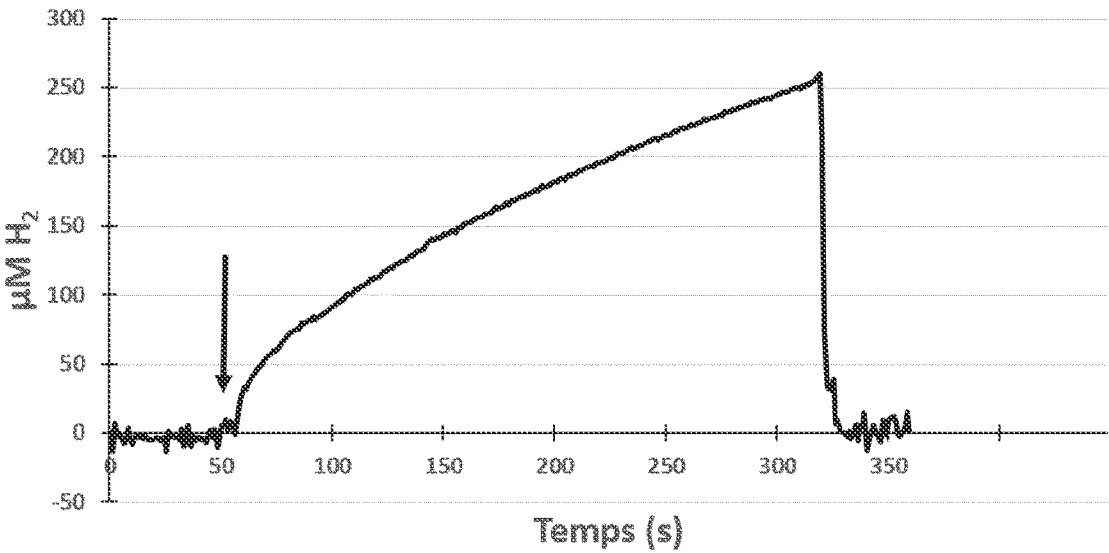

FIG. 13 illustrates the highlighting of the hydrogenase activity by the production of hydrogen which results from the addition of the HoxH recombinant protein to a reagent containing methyl-viologen previously reduced by sodium dithionite in the absence of oxygen. HoxH is able to take the electrons of the methyl-viologen previously reduced to combine them with protons (present in the buffer) in order to produce hydrogen according to the equation $H_2 \leftrightarrow 2H^+ + 2e^-$ which represents the hydrogenase-catalyzed reaction. The level of hydrogen dissolved in the reagent is continuously measured using a micro-sensor (Unisense®, Denmark). The arrow shows the moment when the addition of the HoxH recombinant protein is made, moment concomitant with the increase in the level of dissolved hydrogen detected by the micro-sensor.

Figure 14:
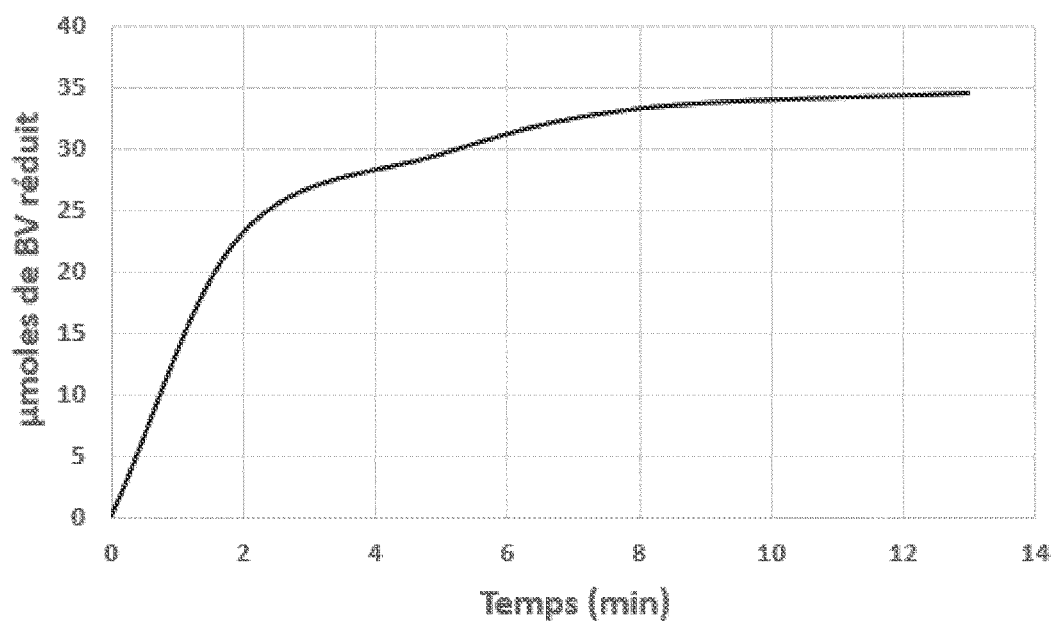

FIG. 14 illustrates the highlighting of the hydrogenase activity by the reduction of benzyl viologen which results from the addition of the HoxH recombinant protein to a reagent containing benzyl viologen (BV) in the presence of $H_2$. HoxH is able to take electrons from hydrogen to transfer them to a redox mediator, for example benzyl viologen, at the same time as the production of protons according to the equation $H_2 \leftrightarrow 2H^+ + 2e^-$ which represents the hydrogenase-catalyzed reaction. The level of hydrogen consumed is equivalent to the level of reduced benzyl viologen, a level that can be measured continuously by spectrophotometry at a wavelength of 578 nm.

Figure 15:
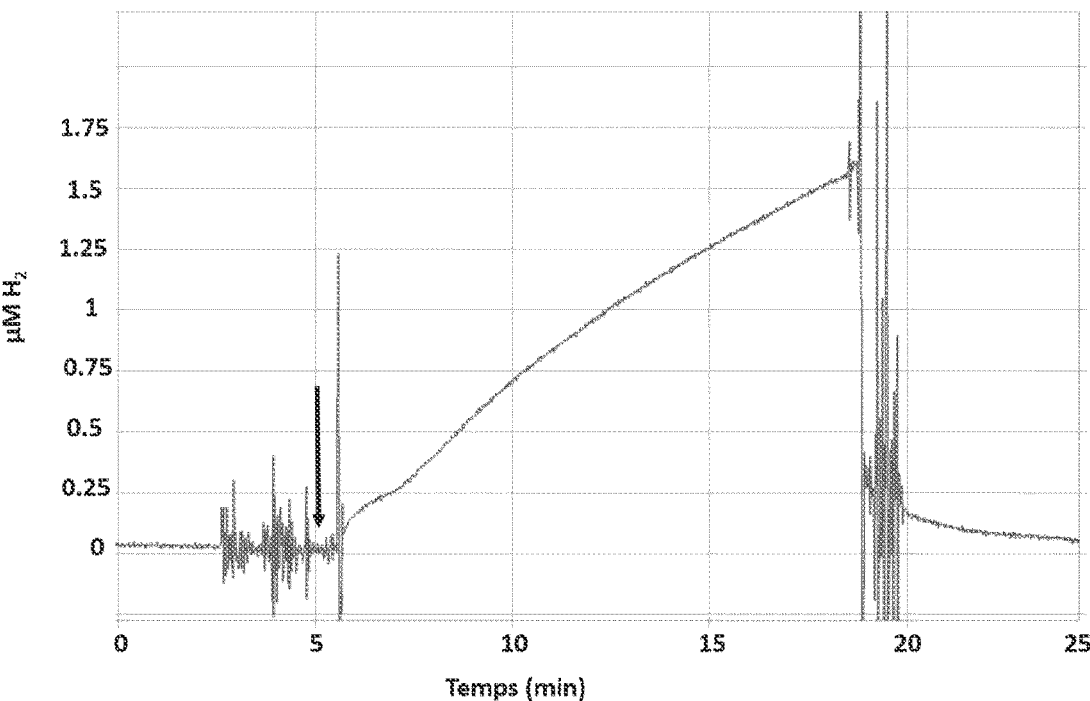

FIG. 15 illustrates the highlighting of the hydrogenase activity by the production of hydrogen which results from the addition of the HoxH recombinant protein, produced in the absence of the HupABCDEFHoxW maturation factors exogenous to *E. coli*, to a reagent containing methyl-viologen previously reduced by sodium dithionite in the absence of oxygen. HoxH is able to take electrons of the previously reduced methyl-viologen to combine them with protons (present in the buffer) in order to produce hydrogen according to the equation $H_2 \leftrightarrow 2H^+ + 2e^-$ which represents the hydrogenase-catalyzed reaction.

EXAMPLES

1. Construction of a HoxH Expression Vector
1.1. "Simple" Sequence of HoxH

HoxH corresponds to the large subunit comprising the active site of HoxEFUYH [NiFe]-hydrogenase in *Synechocystis* sp. PCC6803. The accession number of the protein in Genbank is BAA18091.1. The theoretical isoelectric point of HoxH is 5.86 for a theoretical molecular mass of 52996.53 Daltons. The nucleotide sequence (1425 bp) of HoxH is as follows and is named SEQ ID NO:1 in the context of the present invention:

atgtctaaaaccattgttatcgatcccgttacccggattgaaggccatgccaaaatctccattttcctcaa cgaccagggcaacgtagatgatgttcgtttccatgtggtggagtatcggggttttgaaaaattttgcgaa ggtcgtcccatgtgggaaatggctggtattaccgcccgtatttgcggcatttgtccggttagccatctgct ctgtgcggctaaaaccggggataagttactggcggtgcaaatccctccagccggggaaaaactgc gccgtttaatgaatttagggcaaattacccaatcccacgccctaagttttttccatctcagcagtcctgatt ttctgcttggttgggacagtgatcccgctactcgcaatgtgtttggtttaattgctgctgacccgatttagc tagggcaggtattcggttacggcaatttggccaaacggtaattgaacttttgggagctaaaaaaatcc actctgcttggtcagtgcccggtggagtccgatcgccgttgtcggaagaaggcagacaatggattgtg gaccgtttaccagaagcaaaagaaaccgtttatttagccttaaatttgtttaaaaatatgttggaccgctt ccaaacagaagtggcagaatttggcaaatttccctccctatttatgggcttagttgggaaaaataatga atgggaacattatggcggctccctgcggtttaccgacagtgaaggcaatattgtcgcggacaatctca gtgaagataattacgctgattttattggtgaatcggtggaaaaatggtcctatttaaaatttccctactaca aatctctgggttatcccgatggcatttatcgggttggtccccttgcccgccttaatgtttgtcatcacattgg cacccggaagcagaccaagaattagaagaatatcggcaacgggctggaggtgtggccacgtcc tctttcttttatcattacgcccgcttggtggaaattcttgcctgtttagaagccatcgaattgttaatggctga ccctgatattttgtccaaaaattgtcgagctaaggcagaaattaattgtaccgaagcggtgggagtga gcgaagcaccccgggggtactttattccaccattacaagatagatgaagatggtctaattaagaaagt gaatttgatcattgccacgggcaacaataacttagccatgaataaaaccgtggcccaaattgccaaa cactacattcgcaatcatgatgtgcaagaagggtttttaaaccgggtggaagcgggtattcgttgttatg atccctgccttagttgttctacccatgcagcgggacaaatgccattgatgatcgatttagttaaccctcag ggggaactaattaagtccatccagcgggattaa The amino acid sequence (474 aa) of HoxH is as follows and is named SEQ ID NO:2 in the context of the present invention:

MSKTIVIDPVTRIEGHAKISIFLNDQGNVDDVRFHVVEYRGFEKFCEGRP

MWEMAGITARICGICPVSHLLCAAKTGDKLLAVQIPPAGEKLRRLMNLG

QITQSHALSFFHLSSPDFLLGWDSDPATRNVFGLIAADPDLARAGIRLR

QFGQTVIELLGAKKIHSAWSVPGGVRSPLSEEGRQWIVDRLPEAKETV

YLALNLFKNMLDRFQTEVAEFGKFPSLFMGLVGKNNEWEHYGGSLRFT

DSEGNIVADNLSEDNYADFIGESVEKWSYLKFPYYKSLGYPDGIYRVGP

LARLNVCHHIGTPEADQELEEYRQRAGGVATSSFFYHYARLVEILACLE

AIELLMADPDILSKNCRAKAEINCTEAVGVSEAPRGTLFHHYKIDEDGLI

KKVNLIIATGNNNLAMNKTVAQIAKHYIRNHDVQEGFLNRVEAGIRCYDP

CLSCSTHAAGQMPLMIDLVNPQGELIKSIQRD

Figure 1:
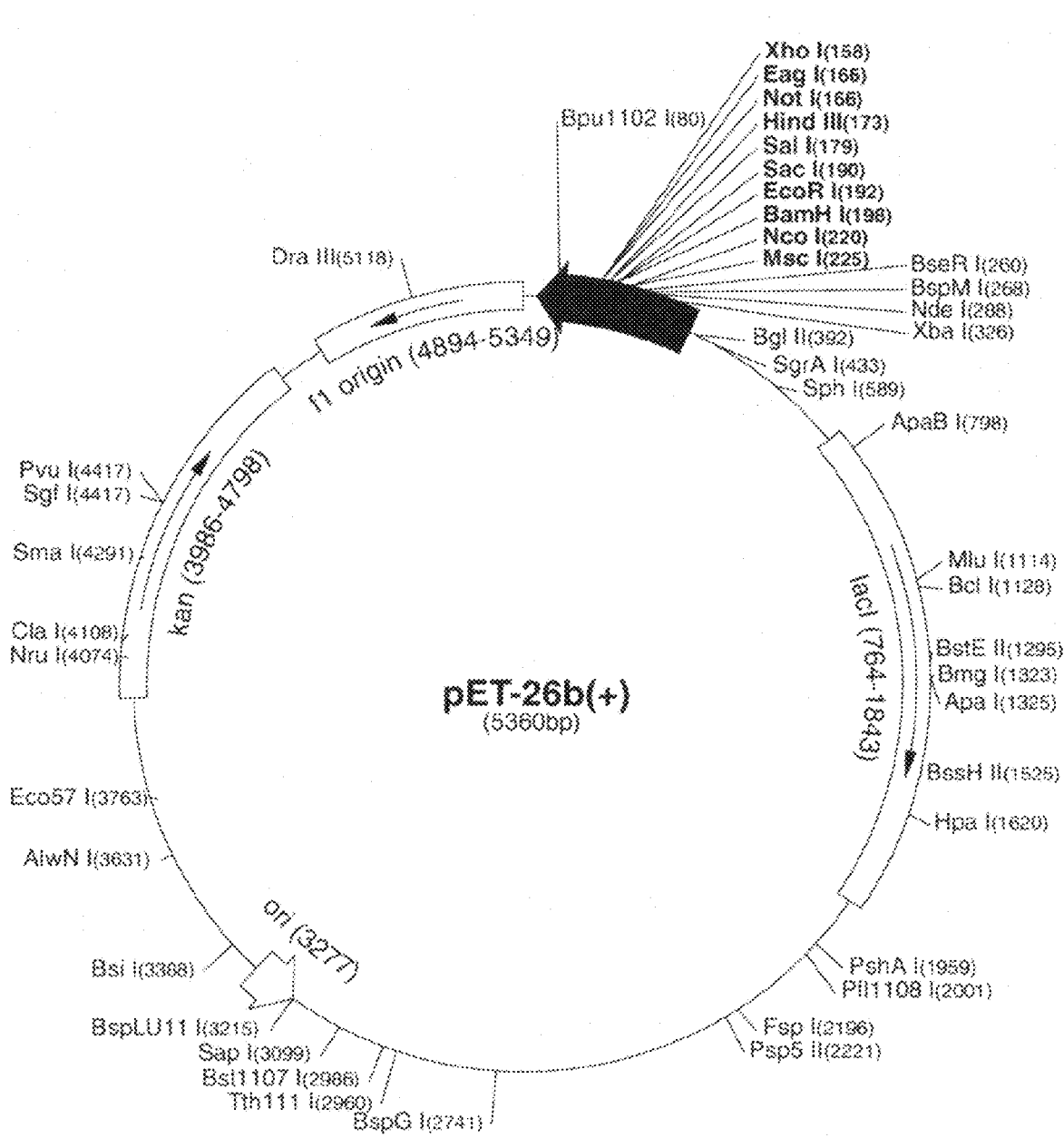
FIG. 1 illustrates the map of plasmid pET-26b(+) (5360 bp).

FIG. 1 shows the map of the plasmid pET26b(+) used to construct the HoxH expression vector by inserting SEQ ID NO:3 into pET26b(+). pET26b(+) is a 5360 bp plasmid possessing an origin of replication for *E. coli*, a kanamycin resistance gene, a multiple cloning site (MCS) containing numerous restriction sites, the T7 promoter and the T7 transcription terminator. It also contains the lacI gene encoding a transcription repressor. This repression of transcription can be lifted by adding IPTG.

1.2. "Optimized" Sequence of HoxH

Optionally, according to an embodiment of to the invention, the sequences SEQ ID NO:1 and SEQ ID NO:2 are optimized for codon usage in *E. coli*. In particular, the NdeI (catatg) and BlpI (gctnagc) restriction sites are added respectively at the beginning and at the end of the nucleotide sequence for cloning in the plasmid pET26b(+) and the sequence caccaccaccaccatcac (underlined below) is also added (sequence encoding the poly-histidine tag close to the N-terminal end of the protein).

The optimized nucleotide sequence (1453 bp) is as follows and is named SEQ ID NO:3 in the context of the present invention:

catatgagccaccaccaccaccatcacaaaaccatcgtcatcgacccagtcacccgcatcgaagg ccacgccaaaattagcattttttctgaacgaccagggcaacgtcgacgacgtccgctttcacgttgttga ataccgtggcttcgaaaaattttgtgaaggtcgtccgatgtgggaaatggccggtatcacggcacgta tttgtggaatttgtccggtgagccatctgctgtgtgccgcaaaaaccggagataaactgctggcagtgc agattccgccggcaggtgaaaaactgcgtcgtctgatgaatctgggtcagattacacagtcgcatgc -continued

```
actgtctttctttcatctgagtagcccagattttctgctggggtgggatagcgacccggcaacacgtaat gtgtttggtctgattgcggctgatccggatctggcgcgtgccggtattcgtctgcgtcagtttggtcagac agttattgagctgctgggggcgaaaaagattcatagtgcatggtctgtgccgggtggtgttcgtagtcc gctgagtgaagaaggtcgtcagtggattgttgatcgtctgccggaggcaaaagaaacggtctatctg gcactgaatctgtttaaaaatatgctggatcgtttccagacagaagttgcagaatttggaaaatttccgt cactgtttatgggtctggttggtaaaaataatgaatgggaacactatggtggtagcctgcgtttcacgga ctctgaaggtaatattgttgcggataatctgagcgaagacaattatgcagattttatcggtgaaagtgtg gaaaaatggagctatctgaaatttccgtattacaaaagcctgggctatccggatgggatctaccgtgtt ggaccgctggcacgtctgaacgtttgtcatcatattggtaccccggaagcagatcaggaactggaag aatatcgtcagcgtgcgggtggtgttgcgactagcagcttttttttatcattatgcacgtctggttgaaattct ggcctgtctggaggcaattgaactgctgatggcagatcctgatattctgtctaaaaattgtcgtgcaaa agcagaaattaactgtaccgaggcagttggtgttagtgaggcgccgcgtggtaccctgtttcatcacta taaaattgacgaagatggtctgattaaaaaggttaatctgattatcgcaaccggtaacaataatctggc aatgaataaaaccgttgcacagattgcaaaacactacattcgcaaccacgatgttcaggaagggttt ctgaatcgtgtagaagccggcattcgctgttatgatccgtgtctgagctgtagcacccatgcagcaggt cagatgcctctgatgattgacctggttaatccgcagggtgagctgattaaaagcattcagcgtgattaa gctgagc
```

The optimized amino acid sequence (480 aa) is as follows and is named SEQ ID NO:4 in the context of the present invention:

```
MSHHHHHHKTIVIDPVTRIEGHAKISIFLNDQGNVDDVRFHVVEYRGFEK

FCEGRPMWEMAGITARICGICPVSHLLCAAKTGDKLLAVQIPPAGEKLR

RLMNLGQITQSHALSFFHLSSPDFLLGWDSDPATRNVFGLIAADPDLAR

AGIRLRQFGQTVIELLGAKKIHSAWSVPGGVRSPLSEEGRQWIVDRLPE

AKETVYLALNLFKNMLDRFQTEVAEFGKFPSLFMGLVGKNNEWEHYG

GSLRFTDSEGNIVADNLSEDNYADFIGESVEKWSYLKFPYYKSLGYPDG

IYRVGPLARLNVCHHIGTPEADQELEEYRQRAGGVATSSFFYHYARLVE

ILACLEAIELLMADPDILSKNCRAKAEINCTEAVGVSEAPRGTLFHHYKI

DEDGLIKKVNLIIATGNNNLAMNKTVAQIAKHYIRNHDVQEGFLNRVEAG

IRCYDPCLSCSTHAAGQMPLMIDLVNPQGELIKSIQRD
```

Plasmid pET26b(+) is used to construct the HoxH expression vector by inserting SEQ ID NO:3 into pET26b(+).

Figure 2:
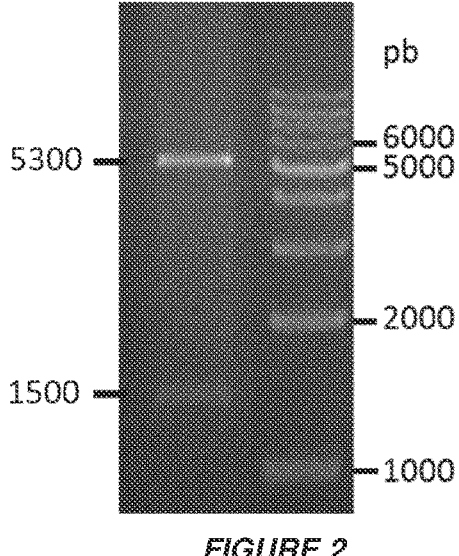
FIG. 2 illustrates the agarose gel analysis of the digestion of the expression vector pET26b(+)+HoxH by the NdeI and BlpI restriction enzymes.

FIG. 2 shows the analysis of the digestion of the expression vector pET26b(+)+HoxH (SEQ ID NO:3) by the NdeI and BlpI restriction enzymes. Two DNA fragments at around 5300 bp (linearized pET26b(+)) and at around 1500 bp (HoxH sequence excised from plasmid pET26b(+)) are highlighted. This confirms the presence of the HoxH sequence of interest in the expression vector pET26b(+).

2. Construction of the Expression Vector of at Least One Maturation Factor

At least the following maturation factors are considered in the context of the present invention: HypA, HypB, HypC, HypD, HypE, HypF and HoxW.

HypA is an expression/formation protein of HoxEFUYH [NiFe]-hydrogenase in *Synechocystis* sp. PCC6803. The accession number of the protein in Genbank is BAA18357.1. The theoretical isoelectric point of HypA is 4.94 for a theoretical molecular mass: 12773.47 Daltons. The nucleotide sequence (342 bp) of HypA is as follows and is named SEQ ID NO:5 in the context of the present invention:

```
atgcacgaagttagtctgatggagcaaactttggcgatcgccattgccc aggcggaagaccatggagccagccaaatccatcgtttaaccctgcgggt ggggcaacagtctggggtggtggccgatgccctacggtttgcgtttgaa gtggtgcgacaaaataccatggccgccgaggcgagattggaaattgaag aaattcccgttacctgtcgttgccaacactgccacgaaaattttcagcc agaggattggatttaccgctgtccccactgcgaccagattagccaaaca gtaatggatggcaaacagttggaactagcatccctagaactgagttga
```

The amino acid sequence (113 aa) of HypA is as follows and is named SEQ ID NO:6 in the context of the present invention:

```
MHEVSLMEQTLAIAIAQAEDHGASQIHRLTLRVGQQSGVADALRFAFE
VVRQNTMAAEARLEIEEIPVTCRCQHCHENFQPEDWIYRCPHCDQISQ
TVMDGKQLELASLELS
```

HypB is an expression/formation protein of HoxEFUYH [NiFe]-hydrogenase in *Synechocystis* sp. PCC6803. The accession number of the protein in Genbank is BAA18312.1. The theoretical isoelectric point of HyB is 5.75 for a theoretical molecular mass: 31242.97 Daltons. The nucleotide sequence (858 bp) of HypB is as follows and is named SEQ ID NO:7 in the context of the present invention:

atgtgccaaaactgcggttgtagtgcggtgggaaccgttgcccatagcc accatcaccatggcgatggaaattttgcccacagccatgatgaccatga ccagcaagaacatcatcaccaccatggcaactacagcaaaagtccaagt cagcagactgtgaccattgaacccgatcgccagtccattgccattggcc aaggcattctcagcaagaatgaccgcctagcggaaaggaatcggggcta tttccaggctaagggcttactggtgatgaatttcctctcttctcccgga gccggtaaaactgctctgatcgaaaaaatggtcggcgatcgacaaaaag accatcccaccgccgtcattgtgggggatttagccaccgataacgatgc ccaacgtctccgcagtgccgggcgatcgccattcaggtcaccacagga aatatttgccatctggaagcggaaatggtggccaaggcggcccaaaagt tagatttagacaatatcgatcaattgatcattgaaaatgttggtaattt ggtttgccccaccacctatgatctaggggaagatttacgggtcgtatta ttttccgtcacagaaggggaggataaacccctaaatatcccgccacct tcaaatcagcccaggttattttagtcaccaaacaggacattgccgccgc agtggattttgatgcagagctggcttggcaaaacctacggcaagtggcc ccccaagcccaaattttgcagtgtctgcccgcacggggaaaggattgc agtcctggtatgagtatttggatcaatggcaactccaacactattcgcc gttggttgatccagcattggcctaa The amino acid sequence (285 aa) of HypB is as follows and is named SEQ ID NO:8 in the context of the present invention:

MCQNCGCSAVGTVAHSHHHHGDGNFAHSHD-
    DHDQQEHHHHHGNYS

KSPSQQTVTIEPDRQSIAIGQGILSKNDRLAERNRGYFQAKGLLVMNFL

SSPGAGKTALIEKMVGDRQKDHPTAVIVGDLATDNDAQRLRSAGAIAIQ

VTTGNICHLEAEMVAKAAQKLDLDNIDQLIIENVGNLVCPTTYDLGEDLR

VVLFSVTEGEDKPLKYPATFKSAQVILVTKQDIAAAVDFDAELAWQNLR

QVAPQAQIFAVSARTGKGLQSWYEYLDQWQLQHYSPLVDPALA

HypC is an expression/formation protein of HoxEFUYH [NiFe]-hydrogenase in *Synechocystis* sp. PCC6803. The accession number of the protein in Genbank is BAA18180.1. The theoretical isoelectric point of HypC is 4.20 for a theoretical molecular mass: 7987.42 Daltons. The nucleotide sequence (231 bp) of HypC is as follows and is named SEQ ID NO:9 in the context of the present invention:

atgtgtctagccctacctggccaggttgtcagtttaatgcccaactccg atccctgttactgacgggaaaggttagctttgggggcatcattaaaac cattagccttgcctacgtacccgaggttaaggtgggggattacgtgatt gtccatgtgggctttgccattagcattgtggacgaagaggcggcccagg aaactttgatagacttggcagaaatgggagtttaa The amino acid sequence (76 aa) of HypC is as follows and is named SEQ ID NO: 10 in the context of the present invention:

MCLALPGQVVSLMPNSDPLLLTGKVSFGGIIKTISLAYVPEVKVGDYVIV

HVGFAISIVDEEAAQETLIDLAEMGV

HypD is an expression/formation protein of HoxEFUYH [NiFe]-hydrogenase in *Synechocystis* sp. PCC6803. The accession number of the protein in Genbank is BAA16622.1. The theoretical isoelectric point of HypD is 6.31 for a theoretical molecular mass of 40632.94 Daltons. The nucleotide sequence (1125 bp) of HypD is as follows and is named SEQ ID NO:11 in the context of the present invention:

atgaaatacgttgatgaatatcgggatgcccaggcggtggcccattacc gtcaggcgatcgccagggagataaccaaaccttggacgctgatggagat ttgcggcggccagacccacagcattgtcaaatatggcttggatgctttg ttgccgaagaatttgactctgatccatggtcccggctgtcctgtgtgcg tcactccgatggaattaattgaccaggctttgtggttagctaagcaacc ggagatcatttttttgttcctttggcgatatgttgcgggtgcccggcagt ggggcggatttgctgagcattaaagcccagggcggcgatgtgcgcattg tctattctcctttggattgtttggcgatcgccagggagaatcctaatcg ggaagtggtattttcggagtaggttttgaaactacagccctgccacg gccatgactctccaccaagctagggcccagggaattagcaatttcagtt tactttgcgcccatgtattggtgcccccggctatggaggctttattagg caatcccaattccctcgtgcagggcttttttggcggcagggcatgtctgt acggtgaccggggaaagggcctatcaacatatcgctgaaaaataccaag tacccattgtcatcactggctttgaacctgtggatattatgcagggcat cttttgcctgtgtgcgccaactggagtcgggacaattcacctgcaacaat caatatcggcgatcggtccaaccccagggcaatgcccatgctcagaaaa ttattgaccaagtgtttgagccagtcgatcgccattggcggggtttggg attaattccggccagcggtttgggtttaaggccagcatttgcccctgg gatgccgcagttaaattcgccaatttattgcaaaccatggccccaacga tgggagaaacagtgtgtattagcggggaaattttacagggacaacggaa gcccagcgattgtccagcctttggtactatctgcacccagaacaaccc ttgggggctcccatggtttcctcggaaggagcctgtgccgcctattacc gttatcgccaacaattaccggaaccagtgggagcggccagagtttag The amino acid sequence (374 aa) of HypD is as follows and is named SEQ ID NO:12 in the context of the present invention:

MKYVDEYRDAQAVAHYRQAIAREITKPWTLMEICGGQTHSIVKYGLDAL

LPKNLTLIHGPGCPVCVTPMELIDQALWLAKQPEIIFCSFGDMLRVPGS

GADLLSIKAQGGDVRIVYSPLDCLAIARENPNREVVFFGVGFETTAPATA

MTLHQARAQGISNFSLLCAHVLVPPAMEALLGNPNSLVQGFLAAGHVC

TVTGERAYQHIAEKYQVPIVITGFEPVDIMQGIFACVRQLESGQFTCNN

-continued
QYRRSVQPQGNAHAQKIIDQVFEPVDRHWRGLGLIPASGLGLRPAFAP

WDAAVKFANLLQTMAPTMGETVCISGEILQGQRKPSDCPAFGTICTPE

QPLGAPMVSSEGACAAYYRYRQQLPEPVGAARV

HypE is an expression/formation protein of HoxEFUYH [NiFe]-hydrogenase in *Synechocystis* sp. PCC6803. The accession number of the protein in Genbank is BAA17478.1. The theoretical isoelectric point of HypE is 4.93 for a theoretical molecular mass of 36425.60 Daltons. The nucleotide sequence (1038 bp) of HypE is as follows and is named SEQ ID NO:13 in the context of the present invention:

gtgaacttagtctgtcccgttcccttgatcgttatccccaggtactgt tagcccacggcggcggcggtaagttgagccaacaattacttaagcaaat tttttaccggcctttggcgcttctgaaacgggtagtcatgatgcggcg gtttttactgccaaccaaagttctttagctttcaccaccgactcctatg tgatcaatcccctcttttttcctgggggcgatattggttctttggcagt ccacggcaccgttaatgacctagccatggccggcgcaacccctcgctat atcagcgttggtttatcctcgaagaaggattgcccatggagaccctct ggcgggtggcccaatccctagggcaagcggcccaaaactgtggggtgga aattcttaccggtgataccaaagtggtggaccggggtaagggagacggc attttcatcaacaccagcggcattggttccctcgaccatcaacaaacta tccatcccaatcaggtacaggtaggcgatcgcctaattttgagcggtga tttgggacgtcatggcatggccattatggcagtgcgccaaggattagaa tttgaaaccaccattgaaagtgattcggccccggttcacagagaagtgc aggcattattgtcggcagggatcccaatccattgtctgcgggatttaac -continued
cagggggggattagccagtgcggttaatgaaattgcccaaacttccggg gtaaccatggctttacgagaaacgttaatcccggtggaggccgaagtac aagccgcctgtgaactgttgggttttgaccccctctatgtggccaatga gggaagattcctggccattgtgcccccggaagcagaacagaagaccgtg gaaatttttgcaaactttccatccccaagctacggcgatcggtacagtaa caggcaaaagtgcacaaaccttggggttagtcagtttggaaagttccat tggtgcccccccggttgctagacatgatcagtggggagcaattaccccgt atttgttag The amino acid sequence (345 aa) of HypE is as follows and is named SEQ ID NO:14 in the context of the present invention:

MNLVCPVPLDRYPQVLLAHGGGGKLSQQLLKQIFLPAFGASETGSHDA

AVFTANQSSLAFTTDSYVINPLFFPGGDIGSLAVHGTVNDLAMAGATPR

YISVGFILEEGLPMETLWRVAQSLGQAAQNCGVEILTGDTKVVDRGKG

DGIFINTSGIGSLDHQQTIHPNQVQVGDRLILSGDLGRHGMAIMAVRQG

LEFETTIESDSAPVHREVQALLSAGIPIHCLRDLTRGGLASAVNEIAQT

SGVTMALRETLIPVEAEVQAACELLGFDPLYVANEGRFLAIVPPEAEQK

TVEILQTFHPQATAIGTVTGKSAQTLGLVSLESSIGAPRLLDMISGEQL

PRIC

HypF is an expression/formation protein of HoxEFUYH [NiFe]-hydrogenase in *Synechocystis* sp. PCC6803. The accession number of the protein in Genbank is BAA10154.1. The theoretical isoelectric point of HypF is 8.19 for a theoretical molecular mass of 85358.25 Daltons. The nucleotide sequence (2304 bp) of HypF is as follows and is named SEQ ID NO: 15 in the context of the present invention:

atgttaaaaaccgttgccatacaggtccagggaagggtgcaaggagtgggttttcgtcccctttgtttata cccttgcccaggaaatgggactgaatggttgggtgaataattccactcaaggagctaccgttgtcatta ccgccgacgaaaaggcgatcgccgactttacggagagattaacgaagacattacctcccctggttt gattgaacaattagccgttgaacagttaccgctggaaagttttactaactttactatccgccccagtagt gatggccctaaaactgcgagtattttacccgatttatccacttgttccgcctgcttaacagaactatttgac cctagcgatcgccgttatctttacccctttattaactgtacccattgcggtccccgctacaccattattgaa gccctaccttacgaccgttgtcgtaccaccatggctaggtttcgccaatgtaccgactgtgaaaggga atataagcaaccaggcgatagacgcttccatgcccaacctaatgcctgtcctcgctgtggcccccaa ctggcttttggaaccgacaaggccaagtaattgcagaagcaaatgaagctttaaactttgctgtagat aatttaaaagtcggcaatattatcgctattaaaggcttaggtggcttccatttgtgttgtgatgccactgatt ttgaagctgtggaaaaattaagattaaggaaacatcgaccggataaaccttggcggtaatgtatggt aatcttggtcaaattgtggagcattaccaacctaataatctagaagttgaattgttacaaagtgccgcc gcccctattgtgttattaaacaaaaaaaaacaattaattttggtggaaaatattgccccaggcaacccc cgagtcggcgtaatgttagcctatactcctttgcatcacttattactaaaaaaattaaagaaacccatgg tagctaccagtggtaacttagctggggagcaaatttgcattgataatattgacgctttaacccggttaca aaatattgctgacggttttctcgttcatgatcgcccgattgtttgtccagtggatgattccgttgtccaaata -continued gtagctgggaagccattattttttgcgtcgagcccggggttacgctcctcaacccattactttaccaaagc ctactcaaaaaaaactattggcgatgggaggtcattataaaaatacagtggcgatcgccaaacaaa atcaagcttacgtcagccaacatttgggcgatttgaattctgctcccacctaccaaaattttgaagaag ccattgcccatttaagccagctatacgatttctctccccaggaaattgttgcagatttacaccctgattattt cagtcatcaatatgctgaaaaccaagctttgcctgtcacttttgtgcagcatcactatgctcatattttagc ggttatggcggaacatggagttatggaggagtccgtgttaggtattgcttgggatggcactggctacgg catggacggtactatttgggggggagaattttttaaaaatcacccaaggtacttggcagagaattgctc atctacaaccatttcatttattaggtaatcaacaagccattaaatatccccatcggattgctttggcgttgtt atggcccacttttggtgatgattttttctgctgattctttaggaaattggttgaatttcaataatgggtttaaaa acaagataaacagcaggttaaatcaggatctaaacaacaaaaatttacgtcaactttggcaacgag ggcaagcaccgctcacttcgagtatgggaagattatttgacggtattgcgacactgataggattgatta acgaagtaacttttgaaggtcaggcggccatagctctggaagctcagattatgccaaatttaactgag gagtattatcctttgactctaaacaacaaggaaaaaaaattagctgttgattggcgcccccttaattaaa gctataaccacagaagatagaagcaaaactaacctaatagccactaaattccacaacagtttagta aatttaattatcactattgcccaacagcagggaatcgaaaaagttgctctggggggaggttgctttcaa aattgttatttgcttgccagtaccattactgccctcaaaaaagctggttttttctcctttgtggcccagagaa ctaccgcccaacgacggtgccatttgcatgggtcaactgttagctaaaattcaggctcggcaatatatc tgttaa The amino acid sequence (767 aa) of HypF is as follows and is named SEQ ID NO: 16 in the context of the present invention:

mlktvaiqvqgrvqgvgfrpfvytlaqemglngwvnnstqgatvvitadekaiadfterltktlpppglie qlaveqlplesftnftirpssdgpktasilpdlstcsacltelfdpsdrrylypfincthcgprytiiealpydrc rttmarfrqctdcereykqpgdrrfhaqpnacprcgpqlafwnrqgqviaeanealnfavdnlkvgnii aikglggfhlccdatdfeaveklrlrkhrpdkplavmygnlgqivehyqpnnlevellqsaaapivllnk kkqlilveniapgnprvgvmlaytplhhlllkklkkpmvatsgnlageqicidnidaltrlqniadgflvhdr pivcpvddsvvqivagkplflrrargyapqpitlpkptqkkllamgghykntvaiakqnqayvsqhlgd lnsaptyqnfeeaiahlsqlydfspqeivadlhpdyfshqyaenqalpvtfvqhhyahilavmaehg vmeesvlgiawdgtgygmdgtiwggeflkitqgtwqriahlqpfhllgnqqaikyphrialallwptfgd dfsadslgnwlnfnngfknkinsrlnqdlnnknlrqlwqrgqapltssmgrlfdgiatliglinevtfegqa aialeaqimpnlteeyypltlnnkekklavdwrplikaittedrsktnliatkfhnslvnliitiaqqqgiekv algggcfqncyllastitalkkagfsplwprelppndgaicmgqllakiqarqyic HoxW is a hypothetical protein in *Synechocystis* sp. [55] PCC6803. The accession number of the protein in Genbank is BAA17680.1. The theoretical isoelectric point of HoxW is 4.93 for a theoretical molecular mass of 17129.53 Daltons. The nucleotide sequence (474 bp) of HoxW is as follows and is named SEQ ID NO:17 in the context of the present invention:

atgccaggccaatccaccaagtccactttaatcatcggttacggcaataccctgcggggggacgac ggcgtggggcgttacctagcggaagaaattgctcagcaaaactggccccattgtggagttatttccac -continued
```
ccatcaactcaccccagaattggccgaggcgatcgccgctgtggaccgggtaattttcattgatgccc aactgcaggaatcagcaaacgaaccatcggtggaagttgtggccttaaaaaccctggaacccaac gaactgtcaggggatttggggcaccggggtaatcccagggaactcttgaccctggctaaaattctcta cggcgttgaggtaaaggcttggtgggtgttgattccggccttcacctttgattatggagagaaattgtctc ccctgaccgcccgggcccaagccgaagccttagcccagatccgccccttggtattgggggagagat aa
```

The amino acid sequence (157 aa) of HoxW is as follows and is named SEQ ID NO: 18 in the context of the present invention:

```
MPGQSTKSTLIIGYGNTLRGDDGVGRYLAEEIAQQNWPHCGVISTHQLT

PELAEAIAAVDRVIFIDAQLQESANEPSVEVVALKTLEPNELSGDLGHRG

NPRELLTLAKILYGVEVKAWWVLIPAFTFDYGEKLSPLTARAQAEALAQI

RPLVLGER
```

Optionally, according to an embodiment in accordance with the invention, all of the maturation factors HypA, HypB, HypC, HypD, HypE, HypF and HoxW are assembled in the form of a concatenary nucleotide sequence (6515 bp). This nucleotide sequence comprises the NcoI restriction site (CCATGG) at the beginning of the sequence and the AvrII restriction site (CCTAGG) at the end of the sequence to carry out the cloning in the pACYCDuet-1 plasmid. This concatenary nucleotide sequence is as follows and is named SEQ ID NO: 19 in the context of the present invention:

```
ccatggcccacgaagttagcctgatggaacagacgctggccattgccattgcgcaggcggaagac cacggggcgagccaaattcaccgtttaacgctgcgcgttgggcagcagtcgggtgttgttgcagatg cattacgctttgcatttgaagttgttcgccagaacacaatggctgcagaagcacgtctggaaatcgag gaaattccggttacctgtcgttgtcagcattgtcatgaaaattttcagccggaggattggatatatagatg tccccattgtgaccagattagtcaaaccgttatggacggcaaacagctggagttagcaagcctggaa ctgagctaagcatggaaaggaggtcgttattatgtgccagaactgtgggtgtagcgcggttgggacc gttgcgcatagccaccatcaccacggggatggcaactttgcgcatagccatgacgaccacgacca gcaggagcaccaccaccaccacggtaactattcaaaatcaccatcacagcagaccgtaaccata gaaccagacagacaaagcatagcaattggccaaggaattctgagcaaaaacgatcgtctggcag aacgcaaccgcggctacttccaggccaaaggtctgttagtaatgaatttcctgagcagcccgggagc aggcaaaaccgcactgatcgaaaaaatggttggtgatcgtcagaaagatcatccgaccgcagttatt gttggtgatctggcaaccgataatgatgcacagcgtctgcgtagcgcaggtgcaattgcaattcaggtt accaccggtaatatttgtcatctggaagcagaaatggttgcaaaagcagcacagaaactggatctg gataatattgatcagctgattattgaaaatgttggtaatctggtttgtccgaccacctatgatctgggtgaa gatctgcgtgttgttctgtttagcgttaccgaaggtgaagataaaccgctgaaatatccggcaacctttta aaagcgcacaggttattctggttaccaaacaggatattgcagcagcagttgattttgatgcagaactg gcatggcagaatctgcgtcaggttgcaccgcaggcacagattttttgcagttagcgcacgtaccggta aaggtctgcagagctggtatgaatatctggatcagtggcagctgcagcattatagcccgctggttgatc cggcactggcataagagttgaaaggaggtttcctccatgtgcctggcgttaccggggcaggttgtttcg ttaatgccgaactcggatccgctgttattaaccgggaaagttagctttggtggtattattaaaaccattag cctggcgtatgttccggaagttaaagttggcgattatgttattgttcatgttggttttgctatcagtattgttgat gaagaagcagcacaggagacactgattgatctggccgagatgggcgtttaattcctaaaaggaggt tttagccatgaagtacgttgacgaataccgcgacgcgcaggcagttgcccactaccgccaggccatt gcccgtgaaattaccaaaccgtggacgctgatggaaatttgtggggggccagacccatagcatcgtta aatatggtctggatgcattattaccgaaaaacttaaccttaatccacggtccgggttgtccggtttgtgtta cgccgatggaactgattgatcaggcattatggctggcaaaacagccggagattatttttttgtagctttgg
```

-continued

```
tgatatgctgcgcgtgccgggtagtggtgcagatctgctgagcattaaagcacaggggggagacgtt cgtatagtttattctccgttagattgtctggcgattgcgcgtgaaaatccgaatcgtgaagttgtttttttttggt gtgggttttgaaactaccgccccggcaaccgcaatgacactgcatcaggcacgggcccagggtatt agcaattttagcttattatgtgcacacgtgttagttccgccggcgatggaagctctgctgggtaacccga atagcctggttcaagggttttttagcagcaggtcatgtttgtacggttaccggtgagcgggcgtatcagc atattgcagagaaatatcaggttccgatagttattaccggttttgaaccggttgatattatgcagggtatttt tgcatgtgttcgtcagctggagagcgggcagtttacatgtaataatcagtaccggcggtcggttcagcc gcagggtaacgcacatgcccagaaaattattgaccaggttttttgaaccggtggatcgtcattggcgtg gattaggtcttattccggcctcaggtttaggtttacgtccggcatttgcaccgtgggacgcagcagttaa attcgcaaatctgttacagacaatggctccgacaatgggtgaaaccgtttgtatttctggcgaaattttac agggtcagcgcaaacctagtgattgtcctgcatttggtaccatctgcaccccggaacaaccgctggg cgccctatggttagcagtgaaggcgcttgtgccgcctattatcgttatcgtcagcaattaccggaacc ggttggtgccgcacgtgtttaattttgcaaaggaggtcctgccaatgaacctggtgtgtccggtgccgct ggaccgctacccgcaggttttactggcacacggggggggggggaagctgagtcagcagctgttaa aacagattttttctgccggcgtttggtgcatcagaaaccggtagccatgatgcagcagtttttaccgcaa atcagagcagcttagcatttacaacagattcctatgttatcaatccgctgtttttttcctggtggtgatattggt agtcttgcagttcatggaaccgttaatgatttagcaatggcaggtgcaacaccgcgttatattagcgttg ggtttattctggaggagggtttaccgatggagacactttggcgtgttgcacaaagcctgggtcaggca gcacagaattgtggagttgaaatattaacaggtgataccaaagttgttgatcgtgggaagggagatg gtattttattaatacatcgggtatcggtagtttagatcaccagcaaaccattcatccgaatcaggttcag gttggtgatcgtctgattctgagtggggatttaggacggcatggtatggcaattatggcagttcgtcagg gcctggaatttgaaacaaccattgaaagcgatagcgcaccggttcatcgtgaggttcaggctctgctg agcgcagggattccgattcactgtctgcgtgacttaacacgtggtggtctggcaagcgccgtgaacg aaattgcacaaacctcaggtgttacaatggctctgcgtgaaaccttaattccggttgaggcggaagttc aagccgcctgtgaactgctgggttttgatcctttatatgttgcgaacgaaggccgtttcctggccattgttc cgccggaagccgaacagaaaaccgttgaaattctgcagacctttcacccgcaggcgaccgcaatt ggtaccgttaccggcaagagtgcacagaccttaggtctggttagcctggagagtagcataggtgccc cacgtctgttagatatgattagcggagaacaactgccacgtatttgttaagactccaaaggaggctag attaatgctgaaaaccgttgccattcaggttcaggggcgcgttcaggggggttggttttcggccgtttgttt acaccttagcccaggaaatgggtctgaatggctgggttaataactctacgcagggtgcaaccgttgtt attaccgcagatgagaaagcaattgcagattttaccgaacgtctgaccaaaacactgccgccaccg ggactgatcgaacaactggcagtggaacagctgccgctggaaagctttaccaactttaccattagac cgagtagcgatggtccgaaaaccgcaagcatcctgccagatctgagcacatgtagcgcctgtctga ccgaattatttgatcccagtgatcgtcgttatctgtacccttttattaattgtacccactgtggtcctcgctata ccattattgaagcactgccttatgaccgttgtcgtaccacaatggctcgttttcgtcagtgtacggattgtg aacgtgaatataagcagccggggggaccgccgttttcatgcacagccaaacgcgtgtccgcgttgtg gtccgcagctggcattctggaaccgtcagggtcaagttattgcagaagccaatgaagcactgaatttc gcagtagataatttaaaggtcggtaatattatcgcaatcaaaggtctgggtggttttcatttatgttgtgat gcaaccgattttgaagccgttgaaaaactgcgtttacgtaaacatcgcccggataagccgctggccg ttatgtacggtaatctgggtcagattgttgagcattatcagccgaataatttagaagttgagctgctgcag
```

-continued

```
agcgcagcagcacctattgttcttctgaataaaaagaaacagctgattctggttgaaaatattgcaccg ggcaatccgcgtgtgggtgttatgctggcatataccccgttacatcacctgttacttaaaaagttaaaga agccgatggttgcaacctccggtaacttagcaggcgaacagatttgtattgacaatattgacgcactg acccgtttacaaaatattgccgacggctttctggttcacgatcgtccgattgtttgtccggttgacgatagt gttgttcagattgtggcaggtaaaccgttattttttaagaagagcccgcggttatgcaccgcagccgatta cccttcctaaacccacccagaaaaagttattagcaatgggaggccattataaaaataccgttgcaatt gcaaagcagaatcaggcatatgtaagccagcatttaggtgatttaaacagcgcaccaacctaccaa aatttcgaagaggcgatagcccatttatcacagctgtatgactttagtccccaggaaattgtcgcagat ctgcatccggattactttagccatcagtacgcagaaaaccaagccctgccggtgacgtttgtacagca tcattatgcacatattctggcagttatggcagaacatggtgttatggaagaaagcgtttttaggcattgcat gggatggcaccggttatggtatggatggtaccatttggggtggtgaatttctgaaaattacgcaggggg acctggcaaagaattgcacatctgcagccgtttcatctgttagggaatcagcaggcaattaaatatcc gcaccggattgcacttgctctgctgtggccgacattcggggacgattttagcgccgatagtctgggtaa ttggttaaattttaacaacggtttcaagaacaagatcaacagccgtttaaaccaagacttaaataataa gaacctgagacaactgtggcagcgtgggcaggcaccgctgacctcgagcatgggcagattatttga tggtatcgcaacactgattggtctgatcaatgaagtaacctttgaaggccaggcagcaattgcattag aggcacaaattatgccgaatctgaccgaagaatactatccgcttaccctgaataacaaagaaaaaa aactggcagttgattggcgtccgctgattaaagcaattaccaccgaagatcgtagcaaaaccaatct gattgcaaccaaatttcataatagcctggttaatctgattattaccattgcacagcagcagggtattgaa aaagttgcactgggtggtggttgtttttcagaattgttatctgctggcaagcaccattaccgcactgaaaa aagcaggttttagcccgctgtggccgcgtgaactgccgccgaatgatggtgcaatttgtatgggtcag ctgctggcaaaaattcaggcacgtcagtatatttgttaactcaacaaaggaggagctggttatgccgg gtcagagcaccaaaagcaccctgattatcgggtacgggaacaccttacgtggggacgatggggtg gggcgctacctggcagaagaaatagcacagcagaactggccgcactgtggtgttattagcacacat cagctgacccccggaactggccgaagcaattgcagcagtggatagagtgattttttattgacgcccaac tgcaggaaagtgcaaatgaaccgtcagttgaagttgttgccctgaaaaccttagaacccaatgaatt aagtggagatctgggtcatcgtggtaatccgcgtgagctgctgacccttagccaaaatattatatggtgtt gaagtcaaagcgtggtgggttctgattccggcctttacctttgattatggtgagaaattatcgcccttaac agcacgtgctcaggccgaagcactggcacagattcgtccgctggttctgggggaacgttaacctag g
```

50

Figure 3:
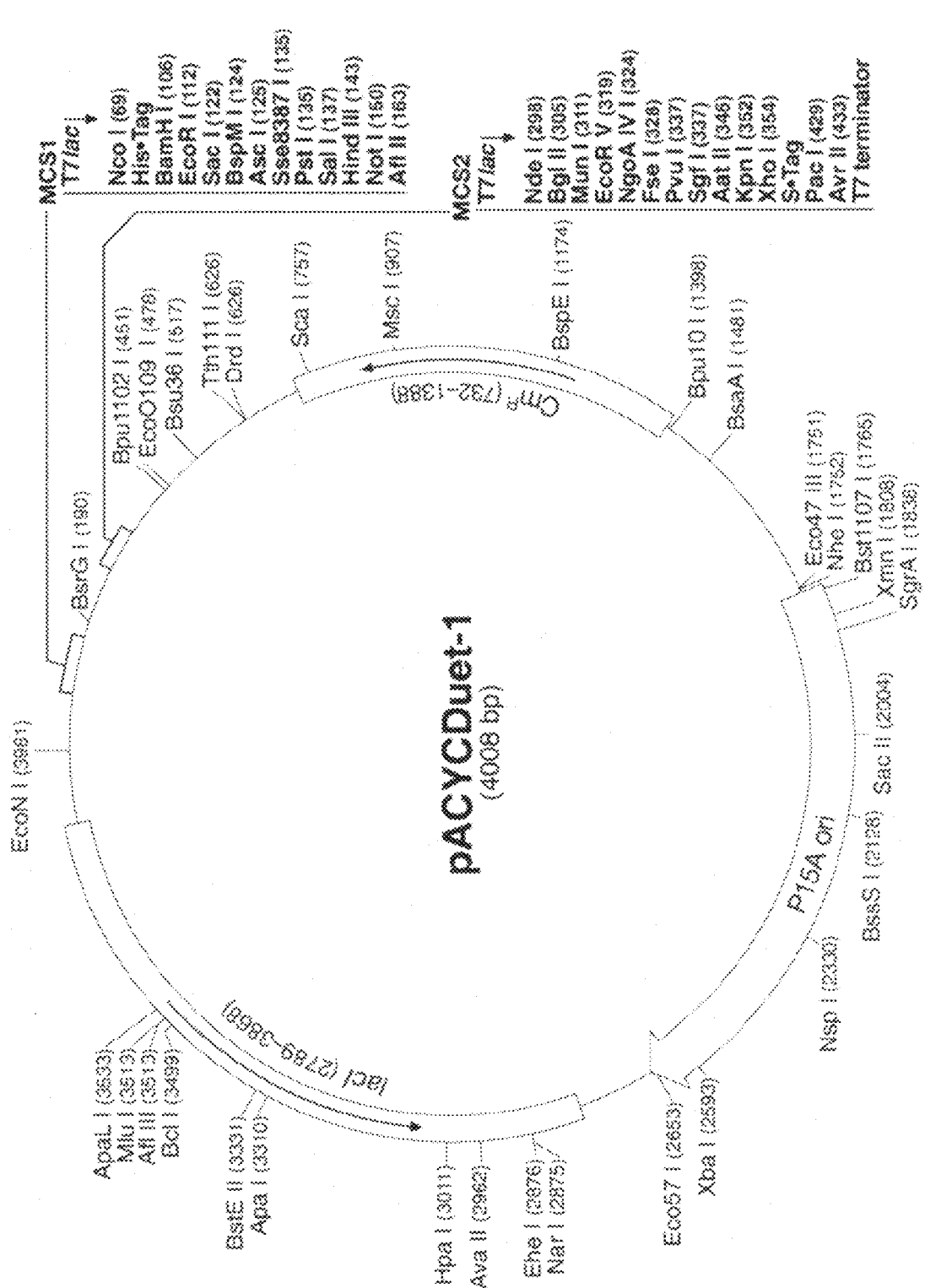
FIG. 3 illustrates the map of plasmid pACYCDuet-1 (4008 bp).

FIG. 3 represents the map of the pACYCDuet-1 plasmid used to construct the expression vector of at least one of the maturation factors HypA, HypB, HypC, HypD, HypE, HypF and HoxW by inserting SEQ ID NO:5 and/or SEQ ID NO:7 and/or SEQ ID NO:9 and/or SEQ ID NO:11 and/or SEQ ID NO:13 and/or SEQ ID NO:15 and/or SEQ ID NO:17 and/or SEQ ID NO:19 in pACYCDuet-1. pACYCDuet-1 is a 4008 bp plasmid, possessing an origin of replication for *E. coli*, a chloramphenicol resistance gene, two multiple cloning sites (MCS) containing numerous restriction sites, the T7 promoter and the T7 transcription terminator. It also contains the lacI gene encoding a transcription repressor. This repression of the transcription can be lifted by adding IPTG.

Figure 4:
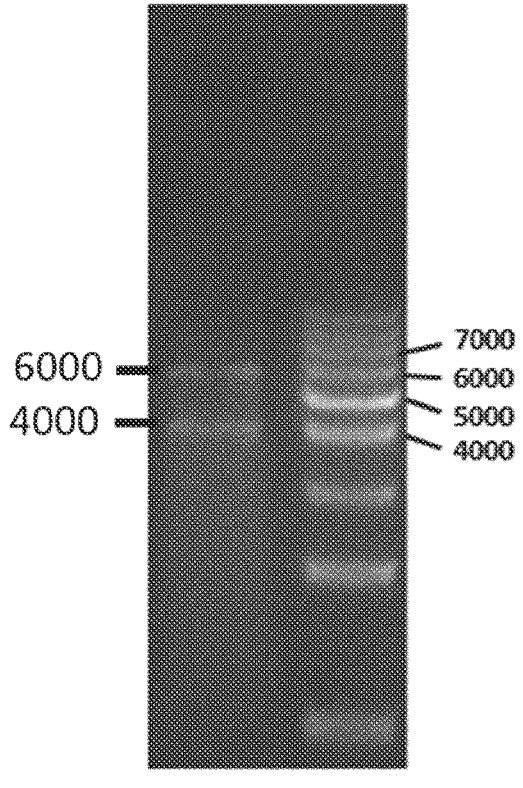
FIG. 4 illustrates the agarose gel analysis of the digestion of the expression vector pACYCDuet-1+HypABCDEF-HoxW by the NcoI and HindIII restriction enzymes.

FIG. 4 shows the analysis of the digestion of the expression vector pACYCDuet-1+HypABCDEFHoxW (concatenary sequence SEQ ID NO: 19) by the NcoI and HindIII restriction enzymes. Two DNA fragments at around 6000 bp and at around 4000 bp are highlighted, as expected for such an enzymatic digestion of the expression vector pACYC-Duet-1+HypABCDEFHoxW. This confirms the presence of the sequence HypABCDEFHoxW in the expression vector pACYCDuet-1.

3. Introduction of the Expression Vectors pET26b(+)+HoxH and pACYCDuet-1+HypABCDEFHoxW in *E. coli*.

The competent cells (DE3) BL21 of *E. coli* were used for the recombinant expression of the HoxH subunit of HoxE-FUYH [NiFe]-hydrogenase from *Synechocystis* sp. PCC6803. These cells are routinely used for the production of recombinant protein under the control of the T7 promoter.

The two expression vectors "pET26b(+)+HoxH" and "pACYCDuet-1+HypABCDEFHoxW" were introduced into these cells by co-transformation according to the traditional heat shock method well known to those skilled in the art. The transformants having double resistance to kanamycin (50 μg/ml) and to chloramphenicol (25 μg/ml) were stored on agar medium at 4° C.

4. Verification of the Presence of DNA Sequences of Interest in *E. coli*.

It is possible that some colonies possess the two plasmids allowing resistance to the selection markers used without however possessing the DNA sequences of interest, namely HoxH and HypABCDEFHoxW. Therefore, it is important to verify the presence of these DNA sequences of interest. An experiment, well known to those skilled in the art and consisting of an extraction of the plasmid DNA from the colony followed by an enzymatic digestion of this plasmid DNA by the restriction enzymes used during the insertion of the DNA sequences of interests in plasmids, has been carried out.

Thus, an extraction of plasmid DNA, according to a protocol well known to those skilled in the art, was carried out on a colony having the double resistance to kanamycin and to chloramphenicol.

Figure 5:
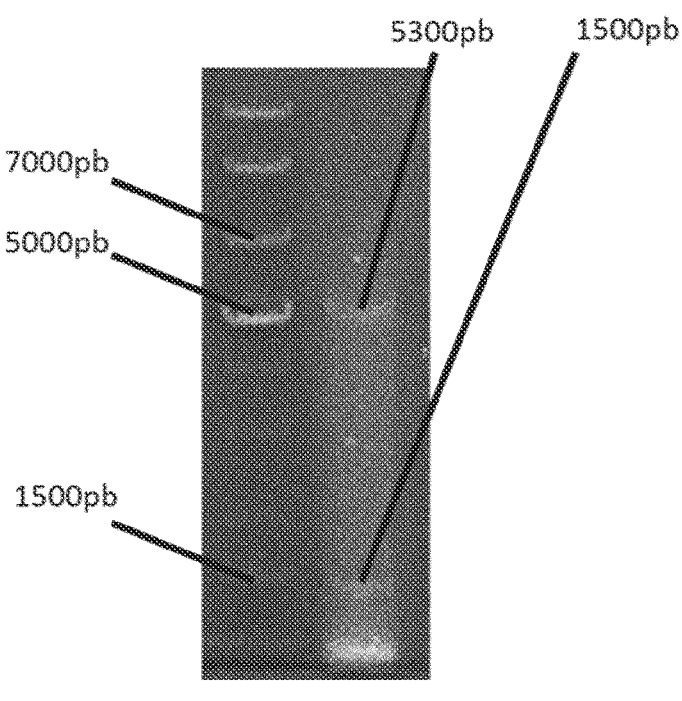
FIG. 5 illustrates the agarose gel analysis of the digestion of the expression vector pET26b(+)+HoxH, derived from the plasmid DNA of an *E. coli* colony, by the NdeI and BlpI restriction enzymes.
Figure 6:
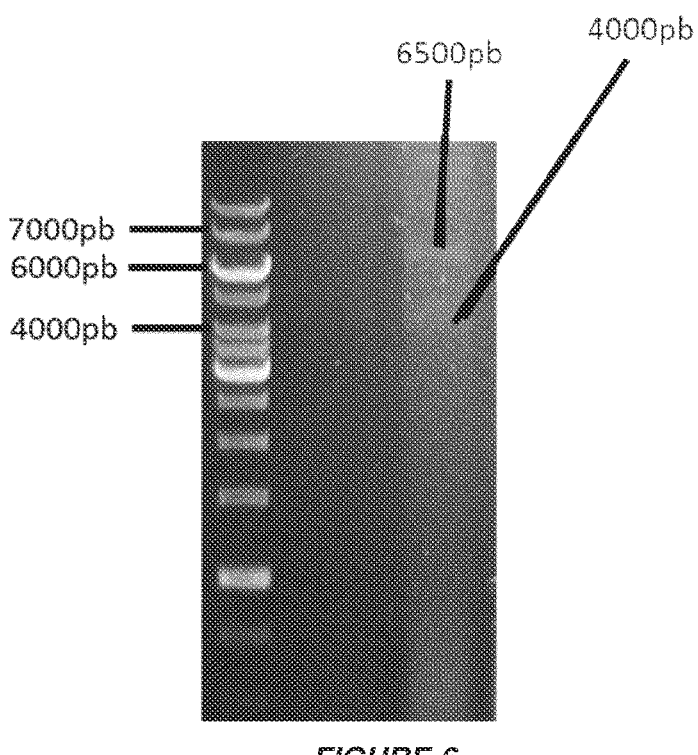
FIG. 6 illustrates the agarose gel analysis of the digestion of the expression vector pACYCDuet-1+HypABCDEF-HoxW, derived from the plasmid DNA of an *E. coli* colony, by the NcoI and HindIII restriction enzymes.

Enzymatic digestion was then carried out, according to a protocol well known to those skilled in the art. The digestion of the expression vector pET26b(+)+HoxH by the NdeI and BlpI restriction enzymes gives two DNA fragments, respectively the linearized plasmid pET26b(+) at 5300 bp and the HoxH DNA fragment of interest at 1500 bp (see FIG. 5). The digestion of the expression vector pACYCDuet-1+Hy-pABCDEFHoxW by the NcoI and HindII restriction enzymes gives two DNA fragments, respectively the linearized plasmid pACYCDuet-1 at 4000 bp and the HypABCDEFHoxW DNA fragment of interest at 6500 bp (see FIG. 6). This confirms the presence in the bacterial colony of the HoxH and HypABCDEFHoxW sequence, respectively in the expression vectors pET26b(+) and PACYCDuet-1.

5. Recombinant Production and Purification by Affinity Chromatography of HoxH in E. Coll.

To obtain the recombinant form of the HoxH subunit of HoxEFUYH [NiFe]-hydrogenase from *Synechocystis* sp. PCC6803, an *E. coli* colony containing the two expression vectors was used to inoculate 4 erlenmeyer flasks with a volume of 250 m each. The culture medium used is the 2XYT medium (16 g of tryptone, 10 g of yeast extract, 5 g of NaCl per litre) supplemented with 100 μM FeAmCi, 50 μM NiSO$_4$, 50 μM cysteine, 50 μg/ml kanamycin and 25 μg/ml chloramphenicol. At an optical density (DO 600 nm) of 1.2, 0.2 mM IPTG are added to the culture in order to induce the recombinant production of the HoxH subunit at 18° C. and under stirring (stirring speed) of 200 rpm. The production time is 20 h at 18° C. The cells are then collected by centrifugation (15 min at 4500 rpm) before starting the purification process.

A purification method was developed in order to confirm the production of the recombinant form of the HoxH subunit of HoxEFUYH [NiFe]-hydrogenase from *Synechocystis* sp. PCC6803. This method (see FIG. 7) purifies HoxH to apparent homogeneity in a single affinity chromatography step. The method involves immobilized metal affinity chromatography (IMAC). The chelating agent is nitrilotriacetic acid (NTA) which allows the binding between the immobile phase and the metal ion. The immobilized metal is nickel (Ni). This chromatography allows a very specific separation of proteins containing a poly-histidine tag. After 20 h of recombinant production of HoxH at 18° C., 1 liter of culture of *E. coli* is collected by centrifugation (15 min at 4500 rpm). The cells are re-suspended in 25 ml of lysis buffer (20 mM sodium phosphate buffer pH 7.5 300 mM KCl+2 μl benzonase+50 μl MgCl$_2$ 1M+1 pellet composed of a cocktail of proteases inhibitors without EDTA) and then lysed by the French press. The supernatant (25 ml) is recovered by centrifugation (15 min at 15000 rpm), filtered (0.45 μm) and applied to the Ni-NTA column (1 ml) previously equilibrated in the wash buffer (20 mM sodium phosphate buffer pH 7.5 300 mM KCl+10 mM imidazole). The column is then washed with 35 ml of wash buffer (20 mM sodium phosphate buffer pH 7.5 300 mM KCl+10 mM imidazole) until the absorbance at 280 nm (representative of the protein concentration) drops to zero. The elution is then carried out through 5 stages with increasing concentration of imidazole, respectively 50 mM, 100 mM, 150 mM, 200 mM and 250 mM) (see FIG. 7).

The SDS-PAGE analysis of the various fractions obtained during the chromatography shows a predominant band close to 54 kDa, which is the expected size for the HoxH subunit, in the fractions eluted at a concentration of 100 mM, 150 mM, 200 mM and 250 mM imidazole (see FIG. 8). HoxH also shows an excellent degree of purity since no additional band is viewable in the fractions eluted at concentrations of 150 mM, 200 mM and 250 mM imidazole. This allows us to conclude that HoxH has been purified to apparent homogeneity in a single affinity chromatography step.

In order to confirm that it is indeed the recombinant form of the HoxH subunit comprising the active site of HoxE-FUYH [NiFe]-hydrogenase from *Synechocystis* sp. PCC6803, an immuno-detection using a poly-histidine anti-tag antibody was carried out (see FIG. 9). A molecular weight marker containing a protein marked with a poly-histidine tag was added to serve as a positive control. The HoxH recombinant protein is well detected in the load, that is to say the supernatant derived from the lysis of the cells of *E. coli* and applied to the Ni-NTA affinity column. The HoxH recombinant protein is also present in the fraction not absorbed by the Ni-NTA column. This indicates that the loading capacity of the Ni-NTA column is exceeded and that a proportion of the HoxH recombinant protein could not bind to it. No signal appears in the "50 mM elution fraction". The HoxH recombinant protein remains attached to the Ni-NTA column at this low imidazole concentration. Finally, the presence of the HoxH recombinant protein is confirmed by immuno-detection in the 200 mM fraction at the expected size, that is to say close to 54 kDa. This unambiguously confirms the purification of the HoxH recombinant protein in a single affinity chromatography step. When the HoxH recombinant protein is highlighted by immuno-detection in a fraction, some bands of low intensity also appear at molecular weights below 54 kDa. It is probably the HoxH recombinant protein partially degraded at the C-terminal end. The proportion of degraded HoxH recombinant proteins seems minimal because the SDS-PAGE analysis does not show the presence of these bands. As a reminder, the immuno-detection is an extremely sensitive method highlighting very small quantities of protein.

6. Highlighting of Hydrogenase Activity in the HoxH Recombinant Protein

The ability to recombinantly express [NiFe]-hydrogenases allows a wide range of possibilities with a view to producing mutant forms with very different properties from the native enzyme. FIG. 10 shows the structure of HoxE-FUYH, [NiFe]-hydrogenase from *Synechocystis* sp. PCC 6803. NADPH is the cofactor of HoxEFUYH in vivo in *Synechocystis* sp. PCC 6803. Methyl-viologen (MV) is used as a redox mediator in the standard in vitro activity test of [NiFe]-hydrogenases. FIG. 11 is a schematic representation (shaded arrow) of the electron transfer and the expected interactions between HoxEFUYH and NADPH and/or MV.

It is generally acquired by those skilled in the art that MV can directly transmit electrons to one or more FeS centers by avoiding FMN. However, as shown in FIG. 12, it is currently not known whether the single HoxH subunit, containing the active site of HoxEFUYH [NiFe]-hydrogenases from *Synechocystis* sp. PCC 6803, can accept electrons directly from MV and therefore produce hydrogen in the absence of additional redox relay.

In the context of the present invention, to test this possibility, the standard in vitro activity test of [NiFe]-hydrogenases in the presence of the HoxH recombinant protein and MV previously reduced by sodium dithionite is implemented (see FIG. 13). HoxH is able to take electrons from the previously reduced methyl-viologen to combine them with protons present in the buffer in order to produce hydrogen according to the equation $H_2 \leftrightarrow 2H^+ + 2e^-$ which represents the hydrogenase-catalyzed reaction. This standard in vitro activity test of [NiFe]-hydrogenases, according to a protocol well known to those skilled in the art, includes the use of a 2 ml flask closed by an airtight and nitrogen degassed septum. 1 ml of reaction mixture, composed of 100 mM sodium dithionite and 10 mM MV dissolved in 10 mM phosphate buffer pH 6.8 and also nitrogen degassed, is added to the flask using a syringe. 200 μg of HoxH recombinant proteins are also added to the reaction mixture. The hydrogen production starts from the moment that the HoxH recombinant proteins are added (moment indicated by an arrow in FIG. 13). The protein content was determined by the Bradford method (Bradford. 1976. A rapid and sensitive method for the quantitation of microgram quantities of protein utilizing the principle of protein-dye binding. Anal Biochem 72:248-254). The hydrogen production is continuously monitored using a previously calibrated hydrogen micro-sensor (Unisense, Aarhus, Denmark).

The activity of the HoxH recombinant protein can therefore be calculated since the quantity of HoxH recombinant protein added (in $mg \cdot ml^{-1}$) is known, as is the speed of hydrogen evolution ($\mu mol\ H_2 \cdot min^{-1}$) for this specific quantity of recombinant protein added. This specific activity can, for example, be 0.1 $\mu mol\ H_2 \cdot min^{-1} \cdot mg^{-1}$ of enzyme.

Unexpectedly and surprisingly, the fact that the single catalytic HoxH subunit containing the active site of HoxE-FUYH [NiFe]-hydrogenase from *Synechocystis* sp. PCC6803 can catalyze the reduction of protons, accepting electrons from a redox mediator (for example, methyl-viologen) without the intermediary of additional FeS centers serving as redox relays, has been highlighted in the context of the present invention.

In the context of the present invention, the standard in vitro activity test of [NiFe]-hydrogenases in the presence of the HoxH recombinant protein, benzyl viologen and hydrogen has also been implemented (see FIG. 14). HoxH is able to take electrons from hydrogen to donate them to benzyl viologen, producing protons on the way according to the equation $H_2 \leftrightarrow 2H^+ + 2e^-$ which represents the hydrogenase-catalyzed reaction. This standard in vitro activity test of [NiFe]-hydrogenases, according to a protocol well known to those skilled in the art, includes the use of a 2 ml flask closed by an airtight and hydrogen gas saturated septum. 2 ml of reaction mixture, composed of 40 μmoles of benzyl viologen dissolved in 50 mM Tris buffer pH 7.6 and also hydrogen degassed, is added to the flask using a syringe. The experiment is carried out at 40° C. 340 μg of HoxH recombinant proteins are also added to the reaction mixture. The consumption of hydrogen and therefore the reduction of benzyl viologen starts from the moment that the HoxH recombinant proteins are added. The protein content was determined by the Bradford method (Bradford. 1976. A rapid and sensitive method for the quantitation of microgram quantities of protein utilizing the principle of protein-dye binding. Anal Biochem 72:248-254). The reduction of benzyl viologen is monitored by spectrophotometry at a wavelength of 578 nm. A molar extinction coefficient of 8,600 $M^{-1}\ cm^{-1}$ was taken into account.

The activity of the HoxH recombinant protein can therefore be calculated since the quantity of HoxH recombinant protein added (in $mg \cdot ml^{-1}$) is known, as is the speed of hydrogen consumption ($\mu mol\ H_2 \cdot min^{-1}$), equivalent to the speed of reduction of benzyl viologen for that specific quantity of recombinant protein added. This specific activity can, for example, be 0.1 $\mu mol\ H_2 \cdot min^{-1} \cdot mg^{-1}$ of enzyme.

Unexpectedly and surprisingly, the fact that the single catalytic HoxH subunit containing the active site of HoxE-FUYH [NiFe]-hydrogenase from *Synechocystis* sp. PCC6803 can catalyze the oxidation of hydrogen, producing protons and donating electrons to a redox mediator (for example, benzyl viologen) without the intermediary of additional FeS centers serving as redox relays, has been highlighted in the context of the present invention.

In the absence of the expression of the other subunits of the HoxEFUYH pentamer, the problems inherent in the prior art are solved at least in part: the HoxH recombinant protein is able on its own to catalyze the reduction of protons, accepting electrons from a redox mediator (for example methyl-viologen) without the intermediary of additional FeS centers serving as redox relays. The HoxH protein is also able on its own to catalyze the oxidation of $H_2$, reducing a redox mediator (for example benzyl viologen) without the intermediary of an additional FeS center serving as a redox relay. This exceptional characteristic demonstrates the great advantage of the present invention, in particular the recombinant production of a single subunit possessing the active site of [NiFe]-hydrogenase and being catalytically active.

7. Recombinant Production, Purification by Affinity Chromatography and Highlighting of Hydrogenase Activity in the HoxH Recombinant Protein Recombinantly Produced in *E. coli* in the Absence of Exogenous Maturation Factors In a manner similar to example 3 above, the expression vector pET26b(+)+HoxH is introduced into *E. coli* (competent cells BL21 (DE3)) by transformation according to the traditional method of heat shock well known to the skilled in the art, and this in the absence of the expression vector pACYCDUET-1+HypABCDEFHoxW. The transformants have resistance to kanamycin (50 μg/ml).

In a manner similar to example 4 above, the presence of the HoxH DNA sequence of interest was verified by the chain of experiments well known to those skilled in the art, which are the extraction of plasmid DNA and the enzymatic digestion.

In a manner similar to example 5 above, the HoxH protein was recombinantly produced in *E. coli*, but in the absence of the plasmid pACYCDUET-1+HupABCDEFHoxW encoding the exogenous maturation factors HupABCDEFHoxW. The HoxH protein was then purified by affinity chromatography, in a manner similar to example 5 above.

In a manner similar to example 6 above, the hydrogenase activity of the HoxH protein recombinantly produced in *E. coli* in the absence of exogenous maturation factors was highlighted according to the protocol involving MV and well known to those skilled in the art Thus, within the context of the present invention, the standard in vitro activity test of [NiFe]-hydrogenases in the presence of the HoxH recombinant protein and MV previously reduced by sodium dithionite was implemented (see FIG. 15). HoxH is able to take the electrons from the previously reduced methyl-viologen to combine them with protons present in the buffer in order to produce hydrogen according to the equation $H_2 \leftrightarrow 2H^+ + 2e^-$ which represents the hydrogenase-catalyzed reaction. This standard in vitro activity test of [NiFe]-hydrogenases, according to a protocol well known to those skilled in the art, includes the use of a 2 ml flask closed by an airtight and nitrogen degassed septum. 1 ml of reaction mixture, composed of 100 mM sodium dithionite and 10 mM MV dissolved in 10 mM phosphate buffer pH 6.8 and also nitrogen degassed, is added to the flask using a syringe. 750 μg of HoxH recombinant proteins are also added to the reaction mixture. The hydrogen production starts from the moment that the HoxH recombinant proteins are added (moment indicated by an arrow in FIG. 15). The protein content was determined by the Bradford method (Bradford. 1976. A rapid and sensitive method for the quantitation of microgram quantities of protein utilizing the principle of protein-dye binding. Anal Biochem 72:248-254). The hydrogen production is continuously monitored using a previously calibrated hydrogen micro-sensor (Unisense, Aarhus, Denmark).

The activity of the HoxH recombinant protein can therefore be calculated since the quantity of HoxH recombinant protein added (in mg·ml$^{-1}$) is known, as is the speed of hydrogen evolution (μmol H$_2$·min$^{-1}$) for this specific quantity of recombinant protein added. This specific activity can, for example, be 0.1 μmol H$_2$·min$^{-1}$·mg$^{-1}$ of enzyme.

It has been highlighted, in the context of the present invention, the fact that the single HoxH catalytic subunit containing the active site of the HoxEFUYH [NiFe]-hydrogenase from *Synechocystis* sp. PCC6803 can catalyze the reduction of protons, accepting electrons from a redox mediator (for example, methyl-viologen) without the intervention of maturation factors HupABCDEFHoxW exogenous to *E. coli*.

The present invention has been described in relation to the specific embodiments, which have a purely illustrative value and should not be considered as limitative. In general, it will appear obvious to the person skilled in the art that the present invention is not limited to the examples illustrated and/or described above.

The use of the verbs "comprise", "include", or any other variant, as well as the conjugations thereof, can in no way exclude the presence of elements other than those mentioned.

The use of the indefinite article "a", "an", or of the definite article "the", to introduce an element does not exclude the presence of a plurality of these elements.

The invention claimed is:

1. A monomeric polypeptide comprising a single subunit comprising an active site of a protein of a [NiFe]-hydrogenase protein, said monomeric polypeptide having hydrogenase activity, wherein said subunit is a HoxH subunit of a HoxEFUYH [NiFe]-hydrogenase protein, and wherein an amino acid sequence of said monomeric polypeptide has at least 80% identity with respect to the amino acid sequence of SEQ ID NO: 2 and/or with respect to the amino acid sequence of SEQ ID NO: 4.

2. The monomeric polypeptide according to claim 1, wherein the monomeric polypeptide is isolated from its natural environment.

3. The monomeric polypeptide according to claim 1, wherein the monomeric polypeptide is purified.

4. The monomeric polypeptide according to claim 1, wherein the monomeric peptide comprises an amino acid sequence having at least 90% identity with respect to the amino acid sequence of SEQ ID NO: 2 and/or with respect to the amino acid sequence of SEQ ID NO: 4.

5. The monomeric polypeptide according to claim 1, wherein the monomeric polypeptide has a hydrogenase activity of at least 0.01 $\mu$mol $H_2 \cdot min^{-1}$ $mg^{-1}$ of enzyme.

6. A host cell comprising the monomeric polypeptide according to claim 1.

7. The host cell according to claim 6, further comprising at least one maturation factor of said [NiFe]-hydrogenase protein, said at least one maturation factor being endogenous to the host cell and/or exogenous to the host cell.

8. The host cell according to claim 7, characterized in that said monomeric polypeptide and/or said at least one maturation factor is/are derived from the expression of at least one gene included in an expression vector, said expression vector being included in said host cell.

9. The host cell according to claim 7, wherein said at least one maturation factor of said [NiFe]-hydrogenase protein is selected from the group consisting of maturation factors HypA, HypB, HypC, HypD, HypE, HypF and HoxW, wherein the respective amino acid sequences of each have at least 80% identity with the amino acid sequences of SEQ ID NO: 6, SEQ ID NO: 8, SEQ ID NO: 10, SEQ ID NO: 12, SEQ ID NO: 14, SEQ ID NO: 16, SEQ ID NO: 18, respectively; or encoded together by a concatenated nucleotide sequence having at least 80% identity with respect to the nucleotide sequence SEQ ID NO: 19, which encodes all of these maturation factors.

10. The host cell comprising a polynucleotide encoding the monomeric polypeptide according to claim 1.

11. The host cell according to claim 10, further comprising at least one maturation factor of said [NiFe]-hydrogenase protein, said at least one maturation factor being endogenous to the host cell and/or exogenous to the host cell.

12. The host cell according to claim 11, wherein said at least one maturation factor of said [NiFe]-hydrogenase protein is selected from the group consisting of maturation factors HypA, HypB, HypC, HypD, HypE, HypF and HoxW, wherein the respective amino acid sequences of each have at least 80% identity with the amino acid sequences of SEQ ID NO: 6, SEQ ID NO: 8, SEQ ID NO: 10, SEQ ID NO: 12, SEQ ID NO: 14, SEQ ID NO: 16, SEQ ID NO: 18, respectively; or encoded together by a concatenated nucleotide sequence having at least 80% identity with respect to the nucleotide sequence SEQ ID NO: 19, which encodes all of these maturation factors.

13. The host cell according to claim 10, wherein said monomeric polypeptide and/or said at least one maturation factor is/are derived from expression of at least one gene included in an expression vector, said expression vector being included in said host cell.

14. A method for obtaining a monomeric polypeptide having hydrogenase activity according to claim 1, said method comprising:

a step of genetic modification, performed in-vivo or in-vitro, of an entity comprising genetic material wherein said step of genetic modification comprises:

a) a genetic modification of a host cell and/or an expression vector by including an exogenous polynucleotide of which at least a portion encodes a monomeric polypeptide comprising a single subunit comprising the active site of the [NiFe]-hydrogenase protein, to obtain a genetically modified host cell and/or a genetically modified expression vector to be incubated in an incubation step performed according to incubation conditions for ensuring expression of said exogenous polynucleotide to produce said monomeric polypeptide; or b) inducing at least one genetic mutation of a host cell to obtain a genetically modified host cell to be incubated in an incubation step performed according to incubation conditions to produce said monomeric polypeptide.

15. The method for obtaining a monomeric polypeptide having hydrogenase activity according to claim 14, wherein said step of genetic modification of said host cell further comprises including in said host cell at least one maturation factor of said [NiFe]-hydrogenase protein, said at least one maturation factor being endogenous to the host cell and/or exogenous to the host cell.

16. The monomeric polypeptide according to claim 1, wherein the monomeric peptide comprises an amino acid sequence having at least 95% identity with respect to the amino acid sequence of SEQ ID NO: 2 and/or with respect to the amino acid sequence of SEQ ID NO: 4.

17. The monomeric polypeptide according to claim 1, wherein the monomeric peptide comprises an amino acid sequence having at least 99% identity with respect to the amino acid sequence of SEQ ID NO: 2 and/or with respect to the amino acid sequence of SEQ ID NO: 4.

18. A method for producing or consuming hydrogen, comprising the following steps:

providing a monomeric polypeptide according to claim 1; and incubating said monomeric polypeptide according to incubation conditions allowing production or consumption of hydrogen.

19. A method to coat a surface, comprising the following steps:

providing a monomeric polypeptide according to claim 1;

providing a surface;

coating said surface with said monomeric polypeptide; and obtaining a coated surface with said monomeric polypeptide.

20. The method to coat a surface according to claim 19, wherein said surface is an electrical conductor.

* * * * *

SEQUENCE LISTING

<160> NUMBER OF SEQ ID NOS: 19

<210> SEQ ID NO 1
<211> LENGTH: 1425
<212> TYPE: DNA
<213> ORGANISM: Synechocystis PCC6803

<400> SEQUENCE: 1

```
atgtctaaaa ccattgttat cgatcccgtt acccggattg aaggccatgc caaaatctcc      60
attttcctca acgaccaggg caacgtagat gatgttcgtt tccatgtggt ggagtatcgg     120
ggttttgaaa aattttgcga aggtcgtccc atgtgggaaa tggctggtat taccgcccgt     180
atttgcggca tttgtccggt tagccatctg ctctgtgcgg ctaaaaccgg ggataagtta     240
ctggcggtgc aaatccctcc agccggggaa aaactgcgcc gtttaatgaa tttagggcaa     300
attacccaat cccacgccct aagttttttc catctcagca gtcctgattt tctgcttggt     360
tgggacagtg atcccgctac tcgcaatgtg tttggtttaa ttgctgctga ccccgattta     420
gctagggcag gtattcggtt acggcaattt ggccaaacgg taattgaact tttgggagct     480
aaaaaaatcc actctgcttg gtcagtgccc ggtggagtcc gatcgccgtt gtcggaagaa     540
ggcagacaat ggattgtgga ccgtttacca gaagcaaaag aaaccgttta tttagcctta     600
aatttgttta aaaatatgtt ggaccgcttc caaacagaag tggcagaatt tggcaaattt     660
ccctccctat ttatgggctt agttgggaaa aataatgaat gggaacatta tggcggctcc     720
ctgcggttta ccgacagtga aggcaatatt gtcgcggaca atctcagtga agataattac     780
gctgatttta ttggtgaatc ggtggaaaaa tggtcctatt taaaatttcc ctactacaaa     840
tctctgggtt atcccgatgg catttatcgg gttggtcccc ttgcccgcct taatgtttgt     900
catcacattg gcaccccgga agcagaccaa gaattagaag aatatcggca acgggctgga     960
ggtgtggcca cgtcctcttt cttttatcat tacgcccgct tggtggaaat tcttgcctgt    1020
ttagaagcca tcgaattgtt aatggctgac cctgatattt tgtccaaaaa ttgtcgagct    1080
aaggcagaaa ttaattgtac cgaagcggtg ggagtgagcg aagcaccccg gggtactta     1140
```

-continued

```
ttccaccatt acaagataga tgaagatggt ctaattaaga aagtgaattt gatcattgcc      1200
acgggcaaca ataacttagc catgaataaa accgtggccc aaattgccaa acactacatt      1260
cgcaatcatg atgtgcaaga agggttttta aaccgggtgg aagcgggtat tcgttgttat      1320
gatccctgcc ttagttgttc tacccatgca gcgggacaaa tgccattgat gatcgattta      1380
gttaaccctc aggggaact aattaagtcc atccagcggg attaa                       1425
```

<210> SEQ ID NO 2
<211> LENGTH: 474
<212> TYPE: PRT
<213> ORGANISM: Synechocystis PCC6803

<400> SEQUENCE: 2

```
Met Ser Lys Thr Ile Val Ile Asp Pro Val Thr Arg Ile Glu Gly His
1               5                   10                  15

Ala Lys Ile Ser Ile Phe Leu Asn Asp Gln Gly Asn Val Asp Asp Val
                20                  25                  30

Arg Phe His Val Val Glu Tyr Arg Gly Phe Glu Lys Phe Cys Glu Gly
            35                  40                  45

Arg Pro Met Trp Glu Met Ala Gly Ile Thr Ala Arg Ile Cys Gly Ile
        50                  55                  60

Cys Pro Val Ser His Leu Leu Cys Ala Ala Lys Thr Gly Asp Lys Leu
65                  70                  75                  80

Leu Ala Val Gln Ile Pro Pro Ala Gly Glu Lys Leu Arg Arg Leu Met
                85                  90                  95

Asn Leu Gly Gln Ile Thr Gln Ser His Ala Leu Ser Phe Phe His Leu
            100                 105                 110

Ser Ser Pro Asp Phe Leu Leu Gly Trp Asp Ser Asp Pro Ala Thr Arg
        115                 120                 125

Asn Val Phe Gly Leu Ile Ala Ala Asp Pro Asp Leu Ala Arg Ala Gly
    130                 135                 140

Ile Arg Leu Arg Gln Phe Gly Gln Thr Val Ile Glu Leu Leu Gly Ala
145                 150                 155                 160

Lys Lys Ile His Ser Ala Trp Ser Val Pro Gly Gly Val Arg Ser Pro
                165                 170                 175

Leu Ser Glu Glu Gly Arg Gln Trp Ile Val Asp Arg Leu Pro Glu Ala
            180                 185                 190

Lys Glu Thr Val Tyr Leu Ala Leu Asn Leu Phe Lys Asn Met Leu Asp
        195                 200                 205

Arg Phe Gln Thr Glu Val Ala Glu Phe Gly Lys Phe Pro Ser Leu Phe
    210                 215                 220

Met Gly Leu Val Gly Lys Asn Asn Glu Trp Glu His Tyr Gly Gly Ser
225                 230                 235                 240

Leu Arg Phe Thr Asp Ser Glu Gly Asn Ile Val Ala Asp Asn Leu Ser
            245                 250                 255

Glu Asp Asn Tyr Ala Asp Phe Ile Gly Glu Ser Val Glu Lys Trp Ser
        260                 265                 270

Tyr Leu Lys Phe Pro Tyr Tyr Lys Ser Leu Gly Tyr Pro Asp Gly Ile
        275                 280                 285

Tyr Arg Val Gly Pro Leu Ala Arg Leu Asn Val Cys His His Ile Gly
    290                 295                 300

Thr Pro Glu Ala Asp Gln Glu Leu Glu Glu Tyr Arg Gln Arg Ala Gly
305                 310                 315                 320
```

-continued

```
Gly Val Ala Thr Ser Ser Phe Phe Tyr His Tyr Ala Arg Leu Val Glu
            325                 330                 335

Ile Leu Ala Cys Leu Glu Ala Ile Glu Leu Leu Met Ala Asp Pro Asp
            340                 345                 350

Ile Leu Ser Lys Asn Cys Arg Ala Lys Ala Glu Ile Asn Cys Thr Glu
            355                 360                 365

Ala Val Gly Val Ser Glu Ala Pro Arg Gly Thr Leu Phe His His Tyr
        370                 375                 380

Lys Ile Asp Glu Asp Gly Leu Ile Lys Lys Val Asn Leu Ile Ile Ala
385                 390                 395                 400

Thr Gly Asn Asn Asn Leu Ala Met Asn Lys Thr Val Ala Gln Ile Ala
                405                 410                 415

Lys His Tyr Ile Arg Asn His Asp Val Gln Glu Gly Phe Leu Asn Arg
                420                 425                 430

Val Glu Ala Gly Ile Arg Cys Tyr Asp Pro Cys Leu Ser Cys Ser Thr
            435                 440                 445

His Ala Ala Gly Gln Met Pro Leu Met Ile Asp Leu Val Asn Pro Gln
        450                 455                 460

Gly Glu Leu Ile Lys Ser Ile Gln Arg Asp
465                 470
```

```
<210> SEQ ID NO 3
<211> LENGTH: 1453
<212> TYPE: DNA
<213> ORGANISM: Artificial Sequence
<220> FEATURE:
<223> OTHER INFORMATION: Optimized NiFe-hydrogenase HoxEFUYH
<220> FEATURE:
<221> NAME/KEY: misc_feature
<222> LOCATION: (1)..(6)
<223> OTHER INFORMATION: NdeI restriction site
<220> FEATURE:
<221> NAME/KEY: misc_feature
<222> LOCATION: (10)..(27)
<223> OTHER INFORMATION: Poly-histidine tag
<220> FEATURE:
<221> NAME/KEY: misc_feature
<222> LOCATION: (1447)..(1453)
<223> OTHER INFORMATION: BlpI restriction site

<400> SEQUENCE: 3
catatgagcc accaccacca ccatcacaaa accatcgtca tcgacccagt cacccgcatc      60
gaaggccacg ccaaaattag catttttctg aacgaccagg gcaacgtcga cgacgtccgc     120
tttcacgttg ttgaataccg tggcttcgaa aaatttttgtg aaggtcgtcc gatgtgggaa    180
atggccggta tcacggcacg tatttgtgga atttgtccgg tgagccatct gctgtgtgcc    240
gcaaaaaccg gagataaact gctggcagtg cagattccgc cggcaggtga aaaactgcgt    300
cgtctgatga atctgggtca gattacacag tcgcatgcac tgtctttctt tcatctgagt    360
agcccagatt ttctgctggg gtgggatagc gacccggcaa cacgtaatgt gtttggtctg    420
attgcggctg atccggatct ggcgcgtgcc ggtattcgtc tgcgtcagtt tggtcagaca    480
gttattgagc tgctgggggc gaaaaagatt catagtgcat ggtctgtgcc gggtggtgtt    540
cgtagtccgc tgagtgaaga aggtcgtcag tggattgttg atcgtctgcc ggaggcaaaa    600
gaaacggtct atctggcact gaatctgttt aaaaatatgc tggatcgttt ccagacagaa    660
gttgcagaat ttggaaaatt tccgtcactg tttatgggtc tggttggtaa aaataatgaa    720
tgggaacact atggtggtag cctgcgtttc acggactctg aaggtaatat tgttgcggat    780
aatctgagcg aagacaatta tgcagatttt atcggtgaaa gtgtggaaaa atggagctat    840
```

-continued

```
ctgaaatttc cgtattacaa aagcctgggc tatccggatg ggatctaccg tgttggaccg      900
ctggcacgtc tgaacgtttg tcatcatatt ggtaccccgg aagcagatca ggaactggaa      960
gaatatcgtc agcgtgcggg tggtgttgcg actagcagct ttttttatca ttatgcacgt     1020
ctggttgaaa ttctggcctg tctggaggca attgaactgc tgatggcaga tcctgatatt     1080
ctgtctaaaa attgtcgtgc aaaagcagaa attaactgta ccgaggcagt tggtgttagt     1140
gaggcgccgc gtggtaccct gtttcatcac tataaaattg acgaagatgg tctgattaaa     1200
aaggttaatc tgattatcgc aaccggtaac aataatctgg caatgaataa aaccgttgca     1260
cagattgcaa aacactacat tcgcaaccac gatgttcagg aagggtttct gaatcgtgta     1320
gaagccggca ttcgctgtta tgatccgtgt ctgagctgta gcacccatgc agcaggtcag     1380
atgcctctga tgattgacct ggttaatccg cagggtgagc tgattaaaag cattcagcgt     1440
gattaagctg agc                                                        1453
```

<210> SEQ ID NO 4
<211> LENGTH: 462
<212> TYPE: PRT
<213> ORGANISM: Artificial Sequence
<220> FEATURE:
<223> OTHER INFORMATION: 480 aa

<400> SEQUENCE: 4

```
Met Ser His His His His His His Lys Thr Ile Val Ile Asp Pro Val
1               5                   10                  15

Thr Arg Ile Glu Gly His Ala Lys Ile Ser Ile Phe Leu Asn Asp Gln
                20                  25                  30

Gly Asn Val Asp Asp Val Arg Phe His Val Val Glu Tyr Arg Gly Phe
            35                  40                  45

Glu Lys Phe Cys Glu Gly Arg Pro Met Trp Glu Met Ala Gly Ile Thr
        50                  55                  60

Ala Arg Ile Cys Gly Ile Cys Pro Val Ser His Leu Leu Cys Ala Ala
65                  70                  75                  80

Lys Thr Gly Asp Lys Leu Leu Ala Val Gln Ile Pro Pro Ala Gly Glu
                85                  90                  95

Lys Leu Arg Arg Leu Met Asn Leu Gly Gln Ile Thr Gln Ser His Ala
            100                 105                 110

Leu Ser Phe Phe His Leu Ser Ser Pro Asp Phe Leu Leu Gly Trp Asp
        115                 120                 125

Ser Asp Pro Ala Thr Arg Asn Val Phe Gly Leu Ile Ala Ala Asp Pro
    130                 135                 140

Asp Leu Ala Arg Ala Gly Ile Arg Leu Arg Gln Phe Gly Gln Thr Val
145                 150                 155                 160

Ile Glu Leu Leu Gly Ala Lys Lys Ile His Ser Ala Trp Ser Val Pro
                165                 170                 175

Gly Gly Val Arg Ser Pro Leu Ser Glu Glu Gly Arg Gln Trp Ile Val
            180                 185                 190

Asp Arg Leu Pro Glu Ala Lys Glu Thr Val Tyr Leu Ala Leu Asn Leu
        195                 200                 205

Phe Lys Asn Met Leu Asp Arg Phe Gln Thr Glu Val Ala Glu Phe Gly
        210                 215                 220

Lys Phe Pro Ser Leu Phe Met Gly Leu Val Gly Lys Asn Asn Glu Trp
225                 230                 235                 240

Glu His Tyr Gly Gly Ser Leu Arg Phe Thr Asp Ser Glu Gly Asn Ile
```

-continued

```
                    245                 250                 255

Val Ala Asp Asn Leu Ser Glu Asp Asn Tyr Ala Asp Phe Ile Gly Glu
                260                 265                 270

Ser Val Glu Lys Trp Ser Tyr Leu Lys Phe Pro Tyr Tyr Lys Ser Leu
                275                 280                 285

Gly Tyr Pro Asp Gly Ile Tyr Arg Val Gly Pro Leu Ala Arg Leu Asn
        290                 295                 300

Val Cys His His Ile Gly Thr Pro Glu Ala Asp Gln Glu Leu Glu Glu
305                 310                 315                 320

Tyr Arg Gln Arg Ala Gly Gly Val Ala Thr Ser Ser Phe Phe Tyr His
                325                 330                 335

Tyr Ala Arg Leu Val Glu Ile Leu Ala Cys Leu Glu Ala Ile Glu Leu
                340                 345                 350

Leu Met Ala Asp Pro Asp Ile Leu Ser Lys Asn Cys Arg Ala Lys Ala
                355                 360                 365

Glu Ile Asn Cys Thr Glu Ala Val Gly Val Ser Glu Ala Pro Arg Gly
        370                 375                 380

Thr Leu Phe His His Tyr Lys Ile Asp Glu Asp Gly Leu Ile Lys Lys
385                 390                 395                 400

Val Asn Leu Ile Ile Ala Thr Gly Asn Asn Asn Leu Ala Met Asn Lys
                405                 410                 415

Thr Val Ala Gln Ile Ala Lys His Tyr Ile Arg Asn His Asp Val Gln
                420                 425                 430

Glu Gly Phe Leu Asn Arg Val Glu Ala Gly Ile Arg Cys Tyr Asp Pro
        435                 440                 445

Cys Leu Ser Cys Ser Thr His Ala Ala Gly Gln Met Pro Leu
        450                 455                 460
```

```
<210> SEQ ID NO 5
<211> LENGTH: 342
<212> TYPE: DNA
<213> ORGANISM: Synechocystis PCC6803

<400> SEQUENCE: 5
atgcacgaag ttagtctgat ggagcaaact ttggcgatcg ccattgccca ggcggaagac      60
catggagcca gccaaatcca tcgtttaacc ctgcgggtgg ggcaacagtc tggggtggtg     120
gccgatgccc tacggtttgc gtttgaagtg gtgcgacaaa ataccatggc cgccgaggcg     180
agattggaaa ttgaagaaat tcccgttacc tgtcgttgcc aacactgcca cgaaaatttt     240
cagccagagg attggattta ccgctgtccc cactgcgacc agattagcca aacagtaatg     300
gatggcaaac agttggaact agcatcccta gaactgagtt ga                        342
```

```
<210> SEQ ID NO 6
<211> LENGTH: 113
<212> TYPE: PRT
<213> ORGANISM: Synechocystis PCC6803

<400> SEQUENCE: 6

Met His Glu Val Ser Leu Met Glu Gln Thr Leu Ala Ile Ala Ile Ala
1               5                   10                  15

Gln Ala Glu Asp His Gly Ala Ser Gln Ile His Arg Leu Thr Leu Arg
                20                  25                  30

Val Gly Gln Gln Ser Gly Val Val Ala Asp Ala Leu Arg Phe Ala Phe
        35                  40                  45

Glu Val Val Arg Gln Asn Thr Met Ala Ala Glu Ala Arg Leu Glu Ile
```

```
      50              55              60

Glu Glu Ile Pro Val Thr Cys Arg Cys Gln His Cys His Glu Asn Phe
65                  70              75              80

Gln Pro Glu Asp Trp Ile Tyr Arg Cys Pro His Cys Asp Gln Ile Ser
                85              90              95

Gln Thr Val Met Asp Gly Lys Gln Leu Glu Leu Ala Ser Leu Glu Leu
            100             105             110

Ser
```

```
<210> SEQ ID NO 7
<211> LENGTH: 858
<212> TYPE: DNA
<213> ORGANISM: Synechocystis PCC6803

<400> SEQUENCE: 7
atgtgccaaa actgcggttg tagtgcggtg ggaaccgttg cccatagcca ccatcaccat      60
ggcgatggaa attttgccca cagccatgat gaccatgacc agcaagaaca tcatcaccac     120
catggcaact acagcaaaag tccaagtcag cagactgtga ccattgaacc cgatcgccag     180
tccattgcca ttggccaagg cattctcagc aagaatgacc gcctagcgga aaggaatcgg     240
ggctatttcc aggctaaggg cttactggtg atgaatttcc tctcttctcc cggagccggt     300
aaaactgctc tgatcgaaaa aatggtcggc gatcgacaaa aagaccatcc caccgccgtc     360
attgtggggg atttagccac cgataacgat gcccaacgtc tccgcagtgc cggggcgatc     420
gccattcagg tcaccacagg aaatatttgc catctggaag cggaaatggt ggccaaggcg     480
gcccaaaagt tagatttaga caatatcgat caattgatca ttgaaaatgt tggtaatttg     540
gtttgcccca ccacctatga tctaggggaa gatttacggg tcgtattatt ttccgtcaca     600
gaaggggagg ataaacccct taaatatccc gccaccttca aatcagccca ggttatttta     660
gtcaccaaac aggacattgc cgccgcagtg gattttgatg cagagctggc ttggcaaaac     720
ctacggcaag tggcccccca gcccaaatt tttgcagtgt ctgcccgcac ggggaaagga     780
ttgcagtcct ggtatgagta tttggatcaa tggcaactcc aacactattc gccgttggtt     840
gatccagcat tggcctaa                                                     858
```

```
<210> SEQ ID NO 8
<211> LENGTH: 285
<212> TYPE: PRT
<213> ORGANISM: Synechocystis PCC6803

<400> SEQUENCE: 8

Met Cys Gln Asn Cys Gly Cys Ser Ala Val Gly Thr Val Ala His Ser
1               5               10              15

His His His His Gly Asp Gly Asn Phe Ala His Ser His Asp Asp His
            20              25              30

Asp Gln Gln Glu His His His His Gly Asn Tyr Ser Lys Ser Pro
        35              40              45

Ser Gln Gln Thr Val Thr Ile Glu Pro Asp Arg Gln Ser Ile Ala Ile
    50              55              60

Gly Gln Gly Ile Leu Ser Lys Asn Asp Arg Leu Ala Glu Arg Asn Arg
65              70              75              80

Gly Tyr Phe Gln Ala Lys Gly Leu Leu Val Met Asn Phe Leu Ser Ser
                85              90              95

Pro Gly Ala Gly Lys Thr Ala Leu Ile Glu Lys Met Val Gly Asp Arg
            100             105             110
```

```
Gln Lys Asp His Pro Thr Ala Val Ile Val Gly Asp Leu Ala Thr Asp
    115                 120                 125

Asn Asp Ala Gln Arg Leu Arg Ser Ala Gly Ala Ile Ala Ile Gln Val
    130                 135                 140

Thr Thr Gly Asn Ile Cys His Leu Glu Ala Glu Met Val Ala Lys Ala
145                 150                 155                 160

Ala Gln Lys Leu Asp Leu Asp Asn Ile Asp Gln Leu Ile Ile Glu Asn
                165                 170                 175

Val Gly Asn Leu Val Cys Pro Thr Thr Tyr Asp Leu Gly Glu Asp Leu
                180                 185                 190

Arg Val Val Leu Phe Ser Val Thr Glu Gly Glu Asp Lys Pro Leu Lys
                195                 200                 205

Tyr Pro Ala Thr Phe Lys Ser Ala Gln Val Ile Leu Val Thr Lys Gln
    210                 215                 220

Asp Ile Ala Ala Ala Val Asp Phe Asp Ala Glu Leu Ala Trp Gln Asn
225                 230                 235                 240

Leu Arg Gln Val Ala Pro Gln Ala Gln Ile Phe Ala Val Ser Ala Arg
                245                 250                 255

Thr Gly Lys Gly Leu Gln Ser Trp Tyr Glu Tyr Leu Asp Gln Trp Gln
                260                 265                 270

Leu Gln His Tyr Ser Pro Leu Val Asp Pro Ala Leu Ala
    275                 280                 285
```

<210> SEQ ID NO 9
<211> LENGTH: 231
<212> TYPE: DNA
<213> ORGANISM: Synechocystis PCC6803

<400> SEQUENCE: 9

```
atgtgtctag ccctacctgg ccaggttgtc agtttaatgc ccaactccga tcccctgtta      60
ctgacgggaa aggttagctt tgggggcatc attaaaacca ttagccttgc ctacgtaccc     120
gaggttaagg tgggggatta cgtgattgtc catgtgggct ttgccattag cattgtggac     180
gaagaggcgg cccaggaaac tttgatagac ttggcagaaa tgggagttta a              231
```

<210> SEQ ID NO 10
<211> LENGTH: 76
<212> TYPE: PRT
<213> ORGANISM: Synechocystis PCC6803

<400> SEQUENCE: 10

```
Met Cys Leu Ala Leu Pro Gly Gln Val Val Ser Leu Met Pro Asn Ser
1               5                   10                  15

Asp Pro Leu Leu Leu Thr Gly Lys Val Ser Phe Gly Gly Ile Ile Lys
                20                  25                  30

Thr Ile Ser Leu Ala Tyr Val Pro Glu Val Lys Val Gly Asp Tyr Val
        35                  40                  45

Ile Val His Val Gly Phe Ala Ile Ser Ile Val Asp Glu Glu Ala Ala
    50                  55                  60

Gln Glu Thr Leu Ile Asp Leu Ala Glu Met Gly Val
65                  70                  75
```

<210> SEQ ID NO 11
<211> LENGTH: 1125
<212> TYPE: DNA
<213> ORGANISM: Synechocystis PCC6803

-continued

```
<400> SEQUENCE: 11
atgaaatacg ttgatgaata tcgggatgcc caggcggtgg cccattaccg tcaggcgatc     60
gccagggaga taaccaaacc ttggacgctg atggagattt gcggcggcca gacccacagc    120
attgtcaaat atggcttgga tgctttgttg ccgaagaatt tgactctgat ccatggtccc    180
ggctgtcctg tgtgcgtcac tccgatggaa ttaattgacc aggctttgtg gttagctaag    240
caaccggaga tcattttttg ttcctttggc gatatgttgc gggtgcccgg cagtggggcg    300
gatttgctga gcattaaagc ccagggcggc gatgtgcgca ttgtctattc tcctttggat    360
tgtttggcga tcgccaggga gaatcctaat cgggaagtgg tattttttcgg agtaggtttt    420 gaaactacag cccctgccac ggccatgact ctccaccaag ctagggccca gggaattagc    480
aatttcagtt tactttgcgc ccatgtattg gtgcccccgg ctatggaggc tttattaggc    540
aatcccaatt ccctcgtgca gggcttttg gcggcaggc atgtctgtac ggtgaccggg      600
gaaagggcct atcaacatat cgctgaaaaa taccaagtac ccattgtcat cactggcttt    660
gaacctgtgg atattatgca gggcatcttt gcctgtgtgc ccaactgga gtcgggacaa      720 ttcacctgca acaatcaata tcggcgatcg gtccaacccc agggcaatgc catgctcag      780 aaaattattg accaagtgtt tgagccagtc gatcgccatt ggcggggttt gggattaatt    840
ccggccagcg gtttgggttt aaggccagca tttgccccct gggatgccgc agttaaattc    900
gccaatttat tgcaaaccat ggccccaacg atgggagaaa cagtgtgtat tagcgggggaa   960 attttacagg gacaacggaa gcccagcgat tgtccagcct ttggtactat ctgcacccca   1020
gaacaaccct tggggggctcc catggtttcc tcggaaggag cctgtgccgc ctattaccgt   1080
tatcgccaac aattaccgga accagtggga gcggccagag tttag                    1125

<210> SEQ ID NO 12
<211> LENGTH: 374
<212> TYPE: PRT
<213> ORGANISM: Synechocystis PCC6803

<400> SEQUENCE: 12

Met Lys Tyr Val Asp Glu Tyr Arg Asp Ala Gln Ala Val Ala His Tyr
1               5                   10                  15

Arg Gln Ala Ile Ala Arg Glu Ile Thr Lys Pro Trp Thr Leu Met Glu
                20                  25                  30

Ile Cys Gly Gly Gln Thr His Ser Ile Val Lys Tyr Gly Leu Asp Ala
            35                  40                  45

Leu Leu Pro Lys Asn Leu Thr Leu Ile His Gly Pro Gly Cys Pro Val
        50                  55                  60

Cys Val Thr Pro Met Glu Leu Ile Asp Gln Ala Leu Trp Leu Ala Lys
65                  70                  75                  80

Gln Pro Glu Ile Ile Phe Cys Ser Phe Gly Asp Met Leu Arg Val Pro
                85                  90                  95

Gly Ser Gly Ala Asp Leu Leu Ser Ile Lys Ala Gln Gly Gly Asp Val
                100                 105                 110

Arg Ile Val Tyr Ser Pro Leu Asp Cys Leu Ala Ile Ala Arg Glu Asn
            115                 120                 125

Pro Asn Arg Glu Val Val Phe Phe Gly Val Gly Phe Glu Thr Thr Ala
        130                 135                 140

Pro Ala Thr Ala Met Thr Leu His Gln Ala Arg Ala Gln Gly Ile Ser
145                 150                 155                 160

Asn Phe Ser Leu Leu Cys Ala His Val Leu Val Pro Pro Ala Met Glu
```

```
              165                    170                    175
Ala Leu Leu Gly Asn Pro Asn Ser Leu Val Gln Gly Phe Leu Ala Ala
              180                    185                    190

Gly His Val Cys Thr Val Thr Gly Glu Arg Ala Tyr Gln His Ile Ala
              195                    200                    205

Glu Lys Tyr Gln Val Pro Ile Val Ile Thr Gly Phe Glu Pro Val Asp
              210                    215                    220

Ile Met Gln Gly Ile Phe Ala Cys Val Arg Gln Leu Glu Ser Gly Gln
225                    230                    235                    240

Phe Thr Cys Asn Asn Gln Tyr Arg Arg Ser Val Gln Pro Gln Gly Asn
                       245                    250                    255

Ala His Ala Gln Lys Ile Ile Asp Gln Val Phe Glu Pro Val Asp Arg
                       260                    265                    270

His Trp Arg Gly Leu Gly Leu Ile Pro Ala Ser Gly Leu Gly Leu Arg
                       275                    280                    285

Pro Ala Phe Ala Pro Trp Asp Ala Ala Val Lys Phe Ala Asn Leu Leu
              290                    295                    300

Gln Thr Met Ala Pro Thr Met Gly Glu Thr Val Cys Ile Ser Gly Glu
305                    310                    315                    320

Ile Leu Gln Gly Gln Arg Lys Pro Ser Asp Cys Pro Ala Phe Gly Thr
                       325                    330                    335

Ile Cys Thr Pro Glu Gln Pro Leu Gly Ala Pro Met Val Ser Ser Glu
                       340                    345                    350

Gly Ala Cys Ala Ala Tyr Tyr Arg Tyr Arg Gln Gln Leu Pro Glu Pro
              355                    360                    365

Val Gly Ala Ala Arg Val
              370
```

<210> SEQ ID NO 13
<211> LENGTH: 1038
<212> TYPE: DNA
<213> ORGANISM: Synechocystis PCC6803

<400> SEQUENCE: 13

```
gtgaacttag tctgtcccgt tccccttgat cgttatcccc aggtactgtt agcccacggc      60
ggcggcggta agttgagcca acaattactt aagcaaattt ttttaccggc ctttggcgct     120
tctgaaacgg gtagtcatga tgcggcggtt tttactgcca accaaagttc tttagctttc     180
accaccgact cctatgtgat caatcccctc ttttttcctg ggggcgatat tggttctttg     240
gcagtccacg gcaccgttaa tgacctagcc atggccggcg caacccctcg ctatatcagc     300
gttggtttta tcctcgaaga aggattgccc atggagaccc tctggcgggt ggcccaatcc     360
ctagggcaag cggcccaaaa ctgtgggggtg gaaattctta ccggtgatac caaagtggtg     420
gaccggggta agggagacgg cattttcatc aacaccagcg gcattggttc cctcgaccat     480
caacaaacta tccatcccaa tcaggtacag gtaggcgatc gcctaatttt gagcggtgat     540
ttgggacgtc atggcatggc cattatggca gtgcgccaag gattagaatt tgaaaccacc     600
attgaaagtg attcggcccc ggttcacaga gaagtgcagg cattattgtc ggcagggatc     660
ccaatccatt gtctgcggga tttaaccagg gggggattag ccagtgcggt taatgaaatt     720
gcccaaactt ccggggtaac catggcttta cgagaaacgt taatcccggt ggaggccgaa     780
gtacaagccg cctgtgaact gttgggtttt gaccccctct atgtggccaa tgagggaaga     840
ttcctggcca ttgtgccccc ggaagcagaa cagaagaccg tggaaatttt gcaaactttc     900
```

-continued

```
catccccaag ctacggcgat cggtacagta acaggcaaaa gtgcacaaac cttggggtta      960
gtcagtttgg aaagttccat tggtgccccc cggttgctag acatgatcag tggggagcaa     1020
ttaccccgta tttgttag                                                    1038
```

```
<210> SEQ ID NO 14
<211> LENGTH: 345
<212> TYPE: PRT
<213> ORGANISM: Synechocystis PCC6803

<400> SEQUENCE: 14

Met Asn Leu Val Cys Pro Val Pro Leu Asp Arg Tyr Pro Gln Val Leu
1               5                   10                  15

Leu Ala His Gly Gly Gly Lys Leu Ser Gln Gln Leu Leu Lys Gln
            20                  25                  30

Ile Phe Leu Pro Ala Phe Gly Ala Ser Glu Thr Gly Ser His Asp Ala
        35                  40                  45

Ala Val Phe Thr Ala Asn Gln Ser Ser Leu Ala Phe Thr Thr Asp Ser
    50                  55                  60

Tyr Val Ile Asn Pro Leu Phe Phe Pro Gly Gly Asp Ile Gly Ser Leu
65                  70                  75                  80

Ala Val His Gly Thr Val Asn Asp Leu Ala Met Ala Gly Ala Thr Pro
                85                  90                  95

Arg Tyr Ile Ser Val Gly Phe Ile Leu Glu Glu Gly Leu Pro Met Glu
            100                 105                 110

Thr Leu Trp Arg Val Ala Gln Ser Leu Gly Gln Ala Ala Gln Asn Cys
            115                 120                 125

Gly Val Glu Ile Leu Thr Gly Asp Thr Lys Val Val Asp Arg Gly Lys
        130                 135                 140

Gly Asp Gly Ile Phe Ile Asn Thr Ser Gly Ile Gly Ser Leu Asp His
145                 150                 155                 160

Gln Gln Thr Ile His Pro Asn Gln Val Gln Val Gly Asp Arg Leu Ile
                165                 170                 175

Leu Ser Gly Asp Leu Gly Arg His Gly Met Ala Ile Met Ala Val Arg
            180                 185                 190

Gln Gly Leu Glu Phe Glu Thr Thr Ile Glu Ser Asp Ser Ala Pro Val
            195                 200                 205

His Arg Glu Val Gln Ala Leu Leu Ser Ala Gly Ile Pro Ile His Cys
        210                 215                 220

Leu Arg Asp Leu Thr Arg Gly Gly Leu Ala Ser Ala Val Asn Glu Ile
225                 230                 235                 240

Ala Gln Thr Ser Gly Val Thr Met Ala Leu Arg Glu Thr Leu Ile Pro
                245                 250                 255

Val Glu Ala Glu Val Gln Ala Ala Cys Glu Leu Leu Gly Phe Asp Pro
            260                 265                 270

Leu Tyr Val Ala Asn Glu Gly Arg Phe Leu Ala Ile Val Pro Pro Glu
            275                 280                 285

Ala Glu Gln Lys Thr Val Glu Ile Leu Gln Thr Phe His Pro Gln Ala
        290                 295                 300

Thr Ala Ile Gly Thr Val Thr Gly Lys Ser Ala Gln Thr Leu Gly Leu
305                 310                 315                 320

Val Ser Leu Glu Ser Ser Ile Gly Ala Pro Arg Leu Leu Asp Met Ile
                325                 330                 335

Ser Gly Glu Gln Leu Pro Arg Ile Cys
            340                 345
```

-continued

```
<210> SEQ ID NO 15
<211> LENGTH: 2304
<212> TYPE: DNA
<213> ORGANISM: Synechocystis PCC6803

<400> SEQUENCE: 15
atgttaaaaa ccgttgccat acaggtccag ggaagggtgc aaggagtggg ttttcgtccc         60
tttgtttata cccttgccca ggaaatggga ctgaatggtt gggtgaataa ttccactcaa        120
ggagctaccg ttgtcattac cgccgacgaa aaggcgatcg ccgactttac ggagagatta        180
acgaagacat acctcccccc tggtttgatt gaacaattag ccgttgaaca gttaccgctg        240
gaaagtttta ctaactttac tatccgcccc agtagtgatg ccctaaaaac tgcgagtatt        300
ttacccgatt tatccacttg ttccgcctgc ttaacagaac tatttgaccc tagcgatcgc        360
cgttatcttt acccctttat taactgtacc cattgcggtc cccgctacac cattattgaa        420
gccctacctt acgaccgttg tcgtaccacc atggctaggt tcgccaatg taccgactgt         480 gaaagggaat ataagcaacc aggcgataga cgcttccatg cccaacctaa tgcctgtcct        540
cgctgtggcc cccaactggc ttttttggaac cgacaaggcc aagtaattgc agaagcaaat       600
gaagctttaa actttgctgt agataattta aaagtcggca atattatcgc tattaaaggc        660
ttaggtggct ccatttgtg ttgtgatgcc actgattttg aagctgtgga aaaattaaga         720
ttaaggaaac atcgaccgga taaacctttg gcggtaatgt atggtaatct tggtcaaatt        780
gtggagcatt accaacctaa taatctagaa gttgaattgt tacaaagtgc cgccgcccct        840
attgtgttat aaacaaaaa aaacaatta attttggtgg aaaatattgc cccaggcaac         900
ccccgagtcg gcgtaatgtt agcctatact cctttgcatc acttattact aaaaaaatta        960
aagaaaccca tggtagctac cagtggtaac ttagctgggg agcaaatttg cattgataat      1020
attgacgctt taacccggtt acaaaatatt gctgacggtt ttctcgttca tgatcgcccg      1080
attgtttgtc cagtggatga ttccgttgtc caaatagtag ctgggaagcc attatttttg      1140
cgtcgagccc ggggttacgc tcctcaaccc attactttac caaagcctac tcaaaaaaaa      1200
ctattggcga tgggaggtca ttataaaaat acagtggcga tcgccaaaca aaatcaagct      1260
tacgtcagcc aacatttggg cgatttgaat tctgctccca cctaccaaaa ttttgaagaa      1320
gccattgccc atttaagcca gctatacgat ttctctcccc aggaaattgt tgcagattta      1380
caccctgatt atttcagtca tcaatatgct gaaaaccaag ctttgcctgt cacttttgtg      1440
cagcatcact atgctcatat tttagcggtt atggcggaac atggagttat ggaggagtcc      1500
gtgttaggta ttgcttggga tggcactggc tacggcatgg acggtactat ttggggggga      1560 gaattttaa aaatcaccca aggtacttgg cagagaattg ctcatctaca accatttcat        1620
ttattaggta tcaacaagc cattaaatat ccccatcgga ttgctttggc gttgttatgg        1680 cccactttg gtgatgattt ttctgctgat tctttaggaa attggttgaa tttcaataat        1740
gggtttaaaa acaagataaa cagcaggtta aatcaggatc taaacaacaa aaatttacgt      1800
caactttggc aacgagggca agcaccgctc acttcgagta tgggaagatt atttgacggt      1860 attgcgcac tgataggatt gattaacgaa gtaacttttg aaggtcaggc ggccatagct      1920
ctggaagctc agattatgcc aaatttaact gaggagtatt atcctttgac tctaaacaac      1980 aaggaaaaa aattagctgt tgattggcgc cccttaatta aagctataac cacagaagat      2040
agaagcaaaa ctaacctaat agccactaaa ttccacaaca gtttagtaaa tttaattatc      2100
```

-continued

```
actattgccc aacagcaggg aatcgaaaaa gttgctctgg ggggaggttg ctttcaaaat    2160
tgttatttgc ttgccagtac cattactgcc ctcaaaaaag ctggttttc tcctttgtgg    2220 cccagagaac taccgcccaa cgacggtgcc atttgcatgg gtcaactgtt agctaaaatt    2280
caggctcggc aatatatctg ttaa                                          2304
```

<210> SEQ ID NO 16
<211> LENGTH: 767
<212> TYPE: PRT
<213> ORGANISM: Synechocystis PCC6803

<400> SEQUENCE: 16

```
Met Leu Lys Thr Val Ala Ile Gln Val Gln Gly Arg Val Gln Gly Val
1               5                   10                  15

Gly Phe Arg Pro Phe Val Tyr Thr Leu Ala Gln Glu Met Gly Leu Asn
            20                  25                  30

Gly Trp Val Asn Asn Ser Thr Gln Gly Ala Thr Val Val Ile Thr Ala
        35                  40                  45

Asp Glu Lys Ala Ile Ala Asp Phe Thr Glu Arg Leu Thr Lys Thr Leu
    50                  55                  60

Pro Pro Pro Gly Leu Ile Glu Gln Leu Ala Val Glu Gln Leu Pro Leu
65                  70                  75                  80

Glu Ser Phe Thr Asn Phe Thr Ile Arg Pro Ser Ser Asp Gly Pro Lys
                85                  90                  95

Thr Ala Ser Ile Leu Pro Asp Leu Ser Thr Cys Ser Ala Cys Leu Thr
            100                 105                 110

Glu Leu Phe Asp Pro Ser Asp Arg Arg Tyr Leu Tyr Pro Phe Ile Asn
            115                 120                 125

Cys Thr His Cys Gly Pro Arg Tyr Thr Ile Ile Glu Ala Leu Pro Tyr
        130                 135                 140

Asp Arg Cys Arg Thr Thr Met Ala Arg Phe Arg Gln Cys Thr Asp Cys
145                 150                 155                 160

Glu Arg Glu Tyr Lys Gln Pro Gly Asp Arg Arg Phe His Ala Gln Pro
                165                 170                 175

Asn Ala Cys Pro Arg Cys Gly Pro Gln Leu Ala Phe Trp Asn Arg Gln
            180                 185                 190

Gly Gln Val Ile Ala Glu Ala Asn Glu Ala Leu Asn Phe Ala Val Asp
        195                 200                 205

Asn Leu Lys Val Gly Asn Ile Ile Ala Ile Lys Gly Leu Gly Gly Phe
    210                 215                 220

His Leu Cys Cys Asp Ala Thr Asp Phe Glu Ala Val Glu Lys Leu Arg
225                 230                 235                 240

Leu Arg Lys His Arg Pro Asp Lys Pro Leu Ala Val Met Tyr Gly Asn
                245                 250                 255

Leu Gly Gln Ile Val Glu His Tyr Gln Pro Asn Asn Leu Glu Val Glu
            260                 265                 270

Leu Leu Gln Ser Ala Ala Ala Pro Ile Val Leu Leu Asn Lys Lys Lys
        275                 280                 285

Gln Leu Ile Leu Val Glu Asn Ile Ala Pro Gly Asn Pro Arg Val Gly
    290                 295                 300

Val Met Leu Ala Tyr Thr Pro Leu His His Leu Leu Leu Lys Lys Leu
305                 310                 315                 320

Lys Lys Pro Met Val Ala Thr Ser Gly Asn Leu Ala Gly Glu Gln Ile
                325                 330                 335
```

-continued

```
Cys Ile Asp Asn Ile Asp Ala Leu Thr Arg Leu Gln Asn Ile Ala Asp
            340                 345                 350

Gly Phe Leu Val His Asp Arg Pro Ile Val Cys Pro Val Asp Asp Ser
        355                 360                 365

Val Val Gln Ile Val Ala Gly Lys Pro Leu Phe Leu Arg Arg Ala Arg
    370                 375                 380

Gly Tyr Ala Pro Gln Pro Ile Thr Leu Pro Lys Pro Thr Gln Lys Lys
385                 390                 395                 400

Leu Leu Ala Met Gly Gly His Tyr Lys Asn Thr Val Ala Ile Ala Lys
                405                 410                 415

Gln Asn Gln Ala Tyr Val Ser Gln His Leu Gly Asp Leu Asn Ser Ala
            420                 425                 430

Pro Thr Tyr Gln Asn Phe Glu Glu Ala Ile Ala His Leu Ser Gln Leu
        435                 440                 445

Tyr Asp Phe Ser Pro Gln Glu Ile Val Ala Asp Leu His Pro Asp Tyr
    450                 455                 460

Phe Ser His Gln Tyr Ala Glu Asn Gln Ala Leu Pro Val Thr Phe Val
465                 470                 475                 480

Gln His His Tyr Ala His Ile Leu Ala Val Met Ala Glu His Gly Val
                485                 490                 495

Met Glu Glu Ser Val Leu Gly Ile Ala Trp Asp Gly Thr Gly Tyr Gly
            500                 505                 510

Met Asp Gly Thr Ile Trp Gly Gly Glu Phe Leu Lys Ile Thr Gln Gly
        515                 520                 525

Thr Trp Gln Arg Ile Ala His Leu Gln Pro Phe His Leu Leu Gly Asn
    530                 535                 540

Gln Gln Ala Ile Lys Tyr Pro His Arg Ile Ala Leu Ala Leu Leu Trp
545                 550                 555                 560

Pro Thr Phe Gly Asp Asp Phe Ser Ala Asp Ser Leu Gly Asn Trp Leu
                565                 570                 575

Asn Phe Asn Asn Gly Phe Lys Asn Lys Ile Asn Ser Arg Leu Asn Gln
            580                 585                 590

Asp Leu Asn Asn Lys Asn Leu Arg Gln Leu Trp Gln Arg Gly Gln Ala
        595                 600                 605

Pro Leu Thr Ser Ser Met Gly Arg Leu Phe Asp Gly Ile Ala Thr Leu
    610                 615                 620

Ile Gly Leu Ile Asn Glu Val Thr Phe Glu Gly Gln Ala Ala Ile Ala
625                 630                 635                 640

Leu Glu Ala Gln Ile Met Pro Asn Leu Thr Glu Glu Tyr Tyr Pro Leu
                645                 650                 655

Thr Leu Asn Asn Lys Glu Lys Lys Leu Ala Val Asp Trp Arg Pro Leu
            660                 665                 670

Ile Lys Ala Ile Thr Thr Glu Asp Arg Ser Lys Thr Asn Leu Ile Ala
        675                 680                 685

Thr Lys Phe His Asn Ser Leu Val Asn Leu Ile Ile Thr Ile Ala Gln
        690                 695                 700

Gln Gln Gly Ile Glu Lys Val Ala Leu Gly Gly Gly Cys Phe Gln Asn
705                 710                 715                 720

Cys Tyr Leu Leu Ala Ser Thr Ile Thr Ala Leu Lys Lys Ala Gly Phe
                725                 730                 735

Ser Pro Leu Trp Pro Arg Glu Leu Pro Pro Asn Asp Gly Ala Ile Cys
            740                 745                 750

Met Gly Gln Leu Leu Ala Lys Ile Gln Ala Arg Gln Tyr Ile Cys
```

```
        755              760              765
```

<210> SEQ ID NO 17
<211> LENGTH: 474
<212> TYPE: DNA
<213> ORGANISM: Synechocystis PCC6803

<400> SEQUENCE: 17

```
atgccaggcc aatccaccaa gtccacttta atcatcggtt acggcaatac cctgcggggg      60
gacgacggcg tggggcgtta cctagcggaa gaaattgctc agcaaaactg gccccattgt     120
ggagttattt ccacccatca actcacccca gaattggccg aggcgatcgc cgctgtggac     180
cgggtaattt tcattgatgc ccaactgcag gaatcagcaa acgaaccatc ggtggaagtt     240
gtggccttaa aaaccctgga acccaacgaa ctgtcagggg atttggggca ccggggtaat     300
cccagggaac tcttgaccct ggctaaaatt ctctacggcg ttgaggtaaa ggcttggtgg     360
gtgttgattc cggccttcac ctttgattat ggagagaaat gtctcccct gaccgcccgg      420 gcccaagccg aagccttagc ccagatccgc cccttggtat tgggggagag ataa           474
```

<210> SEQ ID NO 18
<211> LENGTH: 157
<212> TYPE: PRT
<213> ORGANISM: Synechocystis PCC6803

<400> SEQUENCE: 18

```
Met Pro Gly Gln Ser Thr Lys Ser Thr Leu Ile Ile Gly Tyr Gly Asn
1               5                   10                  15

Thr Leu Arg Gly Asp Asp Gly Val Gly Arg Tyr Leu Ala Glu Glu Ile
            20                  25                  30

Ala Gln Gln Asn Trp Pro His Cys Gly Val Ile Ser Thr His Gln Leu
        35                  40                  45

Thr Pro Glu Leu Ala Glu Ala Ile Ala Ala Val Asp Arg Val Ile Phe
    50                  55                  60

Ile Asp Ala Gln Leu Gln Glu Ser Ala Asn Glu Pro Ser Val Glu Val
65                  70                  75                  80

Val Ala Leu Lys Thr Leu Glu Pro Asn Glu Leu Ser Gly Asp Leu Gly
                85                  90                  95

His Arg Gly Asn Pro Arg Glu Leu Leu Thr Leu Ala Lys Ile Leu Tyr
            100                 105                 110

Gly Val Glu Val Lys Ala Trp Trp Val Leu Ile Pro Ala Phe Thr Phe
        115                 120                 125

Asp Tyr Gly Glu Lys Leu Ser Pro Leu Thr Ala Arg Ala Gln Ala Glu
    130                 135                 140

Ala Leu Ala Gln Ile Arg Pro Leu Val Leu Gly Glu Arg
145                 150                 155
```

<210> SEQ ID NO 19
<211> LENGTH: 6515
<212> TYPE: DNA
<213> ORGANISM: Artificial Sequence
<220> FEATURE:
<223> OTHER INFORMATION: Optimized expression sequence
<220> FEATURE:
<221> NAME/KEY: misc_feature
<222> LOCATION: (1)..(6)
<223> OTHER INFORMATION: NcoI restriction site
<220> FEATURE:
<221> NAME/KEY: misc_feature
<222> LOCATION: (6510)..(6515)
<223> OTHER INFORMATION: AvrII restriction site

<400> SEQUENCE: 19

```
ccatggccca cgaagttagc ctgatggaac agacgctggc cattgccatt gcgcaggcgg          60
aagaccacgg ggcgagccaa attcaccgtt taacgctgcg cgttgggcag cagtcgggtg         120
ttgttgcaga tgcattacgc tttgcatttg aagttgttcg ccagaacaca atggctgcag         180
aagcacgtct ggaaatcgag gaaattccgg ttacctgtcg ttgtcagcat tgtcatgaaa         240
attttcagcc ggaggattgg atatatagat gtccccattg tgaccagatt agtcaaaccg         300
ttatggacgg caaacagctg gagttagcaa gcctggaact gagctaagca tggaaaggag         360
gtcgttatta tgtgccagaa ctgtgggtgt agcgcggttg ggaccgttgc gcatagccac         420
catcaccacg gggatggcaa ctttgcgcat agccatgacg accacgacca gcaggagcac         480
caccaccacc acggtaacta ttcaaaatca ccatcacagc agaccgtaac catagaacca         540
gacagacaaa gcatagcaat tggccaagga attctgagca aaaacgatcg tctggcagaa         600
cgcaaccgcg gctacttcca ggccaaaggt ctgttagtaa tgaatttcct gagcagcccg         660
ggagcaggca aaaccgcact gatcgaaaaa atggttggtg atcgtcagaa agatcatccg         720
accgcagtta ttgttggtga tctggcaacc gataatgatg cacagcgtct gcgtagcgca         780
ggtgcaattg caattcaggt taccaccggt aatatttgtc atctggaagc agaaatggtt         840
gcaaaagcag cacagaaact ggatctggat aatattgatc agctgattat tgaaaatgtt         900
ggtaatctgg tttgtccgac cacctatgat ctgggtgaag atctgcgtgt tgttctgttt         960
agcgttaccg aaggtgaaga taaaccgctg aaatatccgg caacctttaa aagcgcacag        1020
gttattctgg ttaccaaaca ggatattgca gcagcagttg attttgatgc agaactggca        1080
tggcagaatc tgcgtcaggt tgcaccgcag gcacagattt ttgcagttag cgcacgtacc        1140
ggtaaaggtc tgcagagctg gtatgaatat ctggatcagt ggcagctgca gcattatagc        1200
ccgctggttg atccggcact ggcataagag ttgaaaggag gtttcctcca tgtgcctggc        1260
gttaccgggg caggttgttt cgttaatgcc gaactcggat ccgctgttat taaccgggaa        1320
agttagcttt ggtggtatta ttaaaaccat tagcctggcg tatgttccgg aagttaaagt        1380
tggcgattat gttattgttc atgttggttt tgctatcagt attgttgatg aagaagcagc        1440
acaggagaca ctgattgatc tggccgagat gggcgtttaa ttcctaaaag gaggttttag        1500
ccatgaagta cgttgacgaa taccgcgacg cgcaggcagt tgcccactac cgccaggcca        1560
ttgcccgtga aattaccaaa ccgtggacgc tgatggaaat ttgtggggggc cagacccata        1620 gcatcgttaa atatggtctg gatgcattat taccgaaaaa cttaacctta atccacggtc        1680
cgggttgtcc ggtttgtgtt acgccgatgg aactgattga tcaggcatta tggctggcaa        1740
aacagccgga gattattttt tgtagctttg gtgatatgct gcgcgtgccg ggtagtggtg        1800
cagatctgct gagcattaaa gcacaggggg gagacgttcg tatagtttat tctccgttag        1860
attgtctggc gattgcgcgt gaaaatccga atcgtgaagt tgtttttttt ggtgtgggtt        1920
ttgaaactac cgcccggca accgcaatga cactgcatca ggcacgggcc cagggtatta        1980
gcaattttag cttattatgt gcacacgtgt agttccgcc ggcgatggaa gctctgctgg        2040
gtaacccgaa tagcctggtt caagggtttt tagcagcagg tcatgtttgt acggttaccg        2100
gtgagcgggc gtatcagcat attgcagaga aatatcaggt tccgatagtt attaccggtt        2160
ttgaaccggt tgatattatg caggggtattt ttgcatgtgt tcgtcagctg gagagcgggc        2220
agtttacatg taataatcag taccggcggt cggttcagcc gcagggtaac gcacatgccc        2280
```

-continued

```
agaaaattat tgaccaggtt tttgaaccgg tggatcgtca ttggcgtgga ttaggtctta      2340
ttccggcctc aggtttaggt ttacgtccgg catttgcacc gtgggacgca gcagttaaat      2400
tcgcaaatct gttacagaca atggctccga caatgggtga aaccgtttgt atttctggcg      2460
aaattttaca gggtcagcgc aaacctagtg attgtcctgc atttggtacc atctgcaccc      2520
cggaacaacc gctgggcgcc cctatggtta gcagtgaagg cgcttgtgcc gcctattatc      2580
gttatcgtca gcaattaccg gaaccggttg gtgccgcacg tgtttaattt tgcaaaggag      2640
gtcctgccaa tgaacctggt gtgtccggtg ccgctggacc gctacccgca ggttttactg      2700
gcacacgggg gggggggggaa gctgagtcag cagctgttaa aacagatttt tctgccggcg      2760
tttggtgcat cagaaaccgg tagccatgat gcagcagttt ttaccgcaaa tcagagcagc      2820
ttagcattta caacagattc ctatgttatc aatccgctgt tttttcctgg tggtgatatt      2880
ggtagtcttg cagttcatgg aaccgttaat gatttagcaa tggcaggtgc aacaccgcgt      2940
tatattagcg ttgggtttat tctggaggag ggttttaccga tggagacact ttggcgtgtt      3000
gcacaaagcc tgggtcaggc agcacagaat tgtggagttg aaatattaac aggtgatacc      3060
aaagttgttg atcgtgggaa gggagatggt attttttatta atacatcggg tatcggtagt      3120
ttagatcacc agcaaaccat tcatccgaat caggttcagg ttggtgatcg tctgattctg      3180 agtgggggatt taggacggca tggtatggca attatggcag ttcgtcaggg cctggaattt      3240
gaaacaacca ttgaaagcga tagcgcaccg gttcatcgtg aggttcaggc tctgctgagc      3300
gcagggattc cgattcactg tctgcgtgac ttaacacgtg gtggtctggc aagcgccgtg      3360
aacgaaattg cacaaacctc aggtgttaca atggctctgc gtgaaacctt aattccggtt      3420
gaggcggaag ttcaagccgc ctgtgaactg ctgggtttttg atcctttata tgttgcgaac      3480
gaaggccgtt tcctggccat tgttccgccg gaagccgaac agaaaaccgt tgaaattctg      3540
cagacctttc acccgcaggc gaccgcaatt ggtaccgtta ccggcaagag tgcacagacc      3600
ttaggtctgg ttagcctgga gagtagcata ggtgccccac gtctgttaga tatggattagc      3660 ggagaacaac tgccacgtat ttgttaagac tccaaaggag gctagattaa tgctgaaaac      3720
cgttgccatt caggttcagg ggcgcgttca gggggttggt tttcggccgt ttgtttacac      3780
cttagcccag gaaatgggtc tgaatggctg ggttaataac tctacgcagg gtgcaaccgt      3840
tgttattacc gcagatgaga aagcaattgc agattttacc gaacgtctga ccaaaacact      3900
gccgccaccg ggactgatcg aacaactggc agtggaacag ctgccgctgg aaagctttac      3960
caactttacc attagaccga gtagcgatgg tccgaaaacc gcaagcatcc tgccagatct      4020
gagcacatgt agcgcctgtc tgaccgaatt atttgatccc agtgatcgtc gttatctgta      4080
cccttttatt aattgtaccc actgtggtcc tcgctatacc attattgaag cactgcctta      4140
tgaccgttgt cgtaccacaa tggctcgttt tcgtcagtgt acggattgtg aacgtgaata      4200
taagcagccg ggggaccgcc gttttcatgc acagccaaac gcgtgtccgc gttgtggtcc      4260
gcagctggca ttctggaacc gtcagggtca agttattgca gaagccaatg aagcactgaa      4320
tttcgcagta gataaatttaa aggtcggtaa tattatcgca atcaaaggtc tgggtggttt      4380
tcatttatgt gtgatgcaa ccgatttttga agccgttgaa aaactgcgtt tacgtaaaca      4440
tcgcccggat aagccgctgg ccgttatgta cggtaatctg ggtcagattg ttgagcatta      4500
tcagccgaat aatttagaag ttgagctgct gcagagcgca gcagcaccta ttgttcttct      4560
gaataaaaag aaacagctga ttctggttga aaatattgca ccgggcaatc cgcgtgtggg      4620
tgttatgctg gcatataccc cgttacatca cctgttactt aaaaagttaa agaagccgat      4680
```

-continued

```
ggttgcaacc tccggtaact tagcaggcga acagatttgt attgacaata ttgacgcact    4740
gacccgttta caaaatattg ccgacggctt tctggttcac gatcgtccga ttgtttgtcc    4800
ggttgacgat agtgttgttc agattgtggc aggtaaaccg ttattttaa gaagagcccg     4860 cggttatgca ccgcagccga ttaccttcc taaacccacc cagaaaaagt tattagcaat     4920
gggaggccat tataaaaata ccgttgcaat tgcaaagcag aatcaggcat atgtaagcca    4980
gcatttaggt gatttaaaca gcgcaccaac ctaccaaaat ttcgaagagg cgatagccca    5040
tttatcacag ctgtatgact ttagtcccca ggaaattgtc gcagatctgc atccggatta    5100
ctttagccat cagtacgcag aaaaccaagc cctgccggtg acgtttgtac agcatcatta    5160
tgcacatatt ctggcagtta tggcagaaca tggtgttatg gaagaaagcg ttttaggcat    5220
tgcatgggat ggcaccggtt atggtatgga tggtaccatt tggggtggtg aatttctgaa    5280
aattacgcag gggacctggc aaagaattgc acatctgcag ccgtttcatc tgttagggaa    5340
tcagcaggca attaaatatc cgcaccggat tgcacttgct ctgctgtggc cgacattcgg    5400
ggacgatttt agcgccgata gtctgggtaa ttggttaaat tttaacaacg gtttcaagaa    5460
caagatcaac agccgtttaa accaagactt aaataataag aacctgagac aactgtggca    5520
gcgtgggcag gcaccgctga cctcgagcat gggcagatta tttgatggta tcgcaacact    5580
gattggtctg atcaatgaag taacctttga aggccaggca gcaattgcat tagaggcaca    5640
aattatgccg aatctgaccg aagaatacta tccgcttacc ctgaataaca aagaaaaaaa    5700
actggcagtt gattggcgtc cgctgattaa agcaattacc accgaagatc gtagcaaaac    5760
caatctgatt gcaaccaaat ttcataatag cctggttaat ctgattatta ccattgcaca    5820
gcagcagggt attgaaaaag ttgcactggg tggtggttgt tttcagaatt gttatctgct    5880
ggcaagcacc attaccgcac tgaaaaaagc aggttttagc ccgctgtggc cgcgtgaact    5940
gccgccgaat gatggtgcaa tttgtatggg tcagctgctg gcaaaaattc aggcacgtca    6000
gtatatttgt taactcaaca aaggaggagc tggttatgcc gggtcagagc accaaaagca    6060
ccctgattat cgggtacggg aacaccttac gtggggacga tggggtgggg cgctacctgg    6120
cagaagaaat agcacagcag aactggccgc actgtggtgt tattagcaca catcagctga    6180
ccccggaact ggccgaagca attgcagcag tggatagagt gatttttatt gacgcccaac    6240
tgcaggaaag tgcaaatgaa ccgtcagttg aagttgttgc cctgaaaacc ttagaaccca    6300
atgaattaag tggagatctg ggtcatcgtg gtaatccgcg tgagctgctg accttagcca    6360
aaatattata tggtgttgaa gtcaaagcgt ggtgggttct gattccggcc tttacctttg    6420
attatggtga gaaattatcg cccttaacag cacgtgctca ggccgaagca ctggcacaga    6480
ttcgtccgct ggttctgggg gaacgttaac ctagg                               6515
```